(12) United States Patent
Croce et al.

(10) Patent No.: US 8,859,202 B2
(45) Date of Patent: Oct. 14, 2014

(54) BREAST CANCER BIOMARKER SIGNATURES FOR INVASIVENESS AND PROGNOSIS

(71) Applicant: The Ohio State University, Columbus, OH (US)

(72) Inventors: Carlo M. Croce, Columbus, OH (US); Stefano Volinia, Ferrara (IT)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 13/746,589

(22) Filed: Jan. 22, 2013

(65) Prior Publication Data

US 2013/0190386 A1 Jul. 25, 2013

Related U.S. Application Data

(60) Provisional application No. 61/588,790, filed on Jan. 20, 2012.

(51) Int. Cl.
*C12Q 1/68* (2006.01)
*G06F 17/30* (2006.01)

(52) U.S. Cl.
CPC ........ *C12Q 1/6886* (2013.01); *C12Q 2600/178* (2013.01); *G06F 17/30542* (2013.01); *C12Q 2600/118* (2013.01); *C12Q 2600/158* (2013.01)
USPC .......................................................... 435/6.1

(58) Field of Classification Search
None
See application file for complete search history.

(56) References Cited

U.S. PATENT DOCUMENTS

| | | | |
|---|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,455,995 B2 | 11/2008 | Tanner et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,811,759 B2 | 10/2010 | Han |
| 7,888,010 B2 | 2/2011 | Brown et al. |
| 7,919,245 B2 | 4/2011 | Brown et al. |

(Continued)

FOREIGN PATENT DOCUMENTS

| AU | 2007243475 B2 | 5/2013 |
|---|---|---|
| CA | 2533701 A1 | 2/2005 |

(Continued)

OTHER PUBLICATIONS

EP Search Report, Application No. 12165638.3 dated Jun. 12, 2012.
EP Search Report, Application No. 12165636.7 dated Jun. 8, 2012.
Australian Exam Rpt. No. 3, 2007205257, dated Jan. 9, 2013.
Australian Examination Report No. 2, 2007227423, dated Mar. 1, 2013.
Australian Office Action, Application No. 2007346101 dated Jun. 21, 2012.
Australian Office Action, Application No. 2007205163 dated Mar. 28, 2013.

(Continued)

*Primary Examiner* — Kimberly Chong
(74) *Attorney, Agent, or Firm* — MacMillan, Sobanski & Todd, LLC

(57) ABSTRACT

MicroRNA profiles transition from normal breast to ductal carcinoma in situ and transition to invasive ductal carcinoma (IDC) and methods of use thereof are described. Methods of diagnosis and prognosis using microRNA signatures to differentiate invasive from in situ carcinoma are described. Also described is the use of microRNA expression for predicting overall survival and time to metastasis.

16 Claims, 43 Drawing Sheets
(34 of 43 Drawing Sheet(s) Filed in Color)

(56) References Cited

U.S. PATENT DOCUMENTS

| | | |
|---|---|---|
| 8,084,199 B2 | 12/2011 | Croce et al. |
| 8,361,710 B2 | 1/2013 | Croce et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2003/0143646 A1 | 7/2003 | Laskey et al. |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0013247 A1 | 1/2005 | Sipola et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0116321 A1 | 6/2006 | Robbins et al. |
| 2006/0127895 A1 | 6/2006 | Sabapathy |
| 2006/0134639 A1 | 6/2006 | Huffel et al. |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0199233 A1 | 9/2006 | Dahlberg et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0092882 A1 | 4/2007 | Wang et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023149 A1 | 1/2009 | Knudsen et al. |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0220589 A1 | 9/2009 | Trieu et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0239818 A1 | 9/2009 | Cheng |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004320 A1 | 1/2010 | Elmen et al. |
| 2010/0004322 A1 | 1/2010 | Croce |
| 2010/0021734 A1 | 1/2010 | Uemoto et al. |
| 2010/0048681 A1 | 2/2010 | Croce |
| 2010/0099200 A1 | 4/2010 | Nazabal et al. |
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0151480 A1 | 6/2010 | Taylor et al. |
| 2010/0173319 A1 | 7/2010 | Croce et al. |
| 2010/0179213 A1 | 7/2010 | Patrawala et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0285471 A1 | 11/2010 | Croce et al. |
| 2010/0298410 A1 | 11/2010 | Obad et al. |
| 2010/0305188 A1 | 12/2010 | Nakanoe et al. |
| 2010/0317610 A1 | 12/2010 | Croce |
| 2011/0003704 A1 | 1/2011 | Skog et al. |
| 2011/0021601 A1 | 1/2011 | Park et al. |
| 2011/0054006 A1 | 3/2011 | Slack et al. |
| 2011/0054009 A1 | 3/2011 | Croce et al. |
| 2011/0107440 A1 | 5/2011 | Pivaresi et al. |
| 2011/0136124 A1 | 6/2011 | Roa et al. |
| 2011/0166200 A1 | 7/2011 | Zhang |
| 2011/0251150 A2 | 10/2011 | Bennett et al. |
| 2011/0275534 A1 | 11/2011 | Cohn et al. |

FOREIGN PATENT DOCUMENTS

| | | |
|---|---|---|
| CA | 2587189 A1 | 12/2006 |
| CN | 1282422 A | 1/2011 |
| EP | 1676914 A1 | 7/2006 |
| EP | 235446 A1 | 8/2011 |
| FR | 2877350 A1 | 5/2006 |
| JP | 2005-503827 A | 2/2005 |
| JP | 2005-517452 A | 6/2005 |

(56) References Cited

FOREIGN PATENT DOCUMENTS

| | | |
|---|---|---|
| JP | 2005-192484 A | 7/2005 |
| JP | 2005-521952 A | 7/2005 |
| JP | 2005-296014 A | 10/2005 |
| JP | 2008/086201 A | 4/2008 |
| WO | 9015156 A1 | 12/1990 |
| WO | 9100364 A1 | 1/1991 |
| WO | 9107424 A1 | 5/1991 |
| WO | 9312136 A1 | 6/1993 |
| WO | 9410343 A1 | 5/1994 |
| WO | 9424308 A1 | 10/1994 |
| WO | 9426930 A1 | 11/1994 |
| WO | 9613514 A1 | 5/1996 |
| WO | 9635124 A1 | 11/1996 |
| WO | 9729119 A1 | 8/1997 |
| WO | 9809510 A1 | 3/1998 |
| WO | 0003685 A2 | 1/2000 |
| WO | 0050565 A2 | 8/2000 |
| WO | 0055169 A1 | 9/2000 |
| WO | 0076524 A1 | 12/2000 |
| WO | 0144466 A1 | 6/2001 |
| WO | 0168666 A1 | 9/2001 |
| WO | 0177343 A1 | 10/2001 |
| WO | 0187958 A2 | 11/2001 |
| WO | 02064171 A2 | 8/2002 |
| WO | 02064172 A2 | 8/2002 |
| WO | 03029459 A2 | 4/2003 |
| WO | 03078662 A1 | 9/2003 |
| WO | 03092370 A1 | 11/2003 |
| WO | 2004033659 A2 | 4/2004 |
| WO | 2004043387 A2 | 5/2004 |
| WO | 2004079013 A1 | 9/2004 |
| WO | 2004098377 A2 | 11/2004 |
| WO | 2005/013901 A3 | 2/2005 |
| WO | 2005/017711 A2 | 2/2005 |
| WO | 2005017711 A2 | 2/2005 |
| WO | 2005020795 A2 | 3/2005 |
| WO | 2005060661 A2 | 7/2005 |
| WO | 2005078139 A2 | 8/2005 |
| WO | 2005/079397 A2 | 9/2005 |
| WO | 2005080601 A2 | 9/2005 |
| WO | 2005/094263 A2 | 10/2005 |
| WO | 2005/103298 A2 | 11/2005 |
| WO | 2005/111211 A2 | 11/2005 |
| WO | 2005118806 A2 | 12/2005 |
| WO | 2006105486 A2 | 10/2006 |
| WO | 2006108718 A1 | 10/2006 |
| WO | 2006119266 A2 | 11/2006 |
| WO | 2006133022 A2 | 12/2006 |
| WO | 2006137941 A2 | 12/2006 |
| WO | 2007/016548 A2 | 2/2007 |
| WO | 2007033023 A2 | 3/2007 |
| WO | 2007044413 A2 | 4/2007 |
| WO | 2007081680 A2 | 7/2007 |
| WO | 2007081720 A2 | 7/2007 |
| WO | 2007081740 A2 | 7/2007 |
| WO | 2007084486 A2 | 7/2007 |
| WO | 2007109236 A2 | 9/2007 |
| WO | 2007/112754 A2 | 10/2007 |
| WO | 2007112097 A2 | 10/2007 |
| WO | 2007/127190 A2 | 11/2007 |
| WO | 2008008430 A2 | 1/2008 |
| WO | 2008/016548 A2 | 2/2008 |
| WO | 2008/029295 A2 | 3/2008 |
| WO | 2008/036168 A2 | 3/2008 |
| WO | 2008036776 A2 | 3/2008 |
| WO | 2008054828 A2 | 5/2008 |
| WO | 2008/064519 A1 | 6/2008 |
| WO | 2008070082 A2 | 6/2008 |
| WO | 2008073915 A2 | 6/2008 |
| WO | 2008073920 A2 | 6/2008 |
| WO | 2008094545 A2 | 8/2008 |
| WO | 2008097277 A2 | 8/2008 |
| WO | 2008136971 A1 | 11/2008 |
| WO | 2008153987 A2 | 12/2008 |
| WO | 2008157319 A1 | 12/2008 |
| WO | 2009018303 A2 | 2/2009 |
| WO | 2009020905 A2 | 2/2009 |
| WO | 2009026487 A1 | 2/2009 |
| WO | 2009033140 A1 | 3/2009 |
| WO | 2009049129 A1 | 4/2009 |
| WO | 2009055773 A2 | 4/2009 |
| WO | 2009064590 A2 | 5/2009 |
| WO | 2009070653 A1 | 6/2009 |
| WO | 2009100029 A1 | 8/2009 |
| WO | 2009108853 A1 | 9/2009 |
| WO | 2009108856 A2 | 9/2009 |
| WO | 2009108860 A2 | 9/2009 |
| WO | 2009108866 A2 | 9/2009 |
| WO | 2009152300 A1 | 12/2009 |
| WO | 2010019694 A1 | 2/2010 |
| WO | 2010059779 A1 | 5/2010 |
| WO | 2010065156 A1 | 6/2010 |
| WO | 2010099161 A1 | 9/2010 |
| WO | 2011/057304 A2 | 5/2011 |
| WO | 2011/063382 A1 | 5/2011 |
| WO | 2011/119553 A1 | 9/2011 |
| WO | 2011/163116 A3 | 12/2011 |
| WO | 2012/019053 A2 | 2/2012 |
| WO | 2012/065049 A2 | 5/2012 |
| WO | 2012/097047 A1 | 7/2012 |
| WO | 2012/122239 A1 | 9/2012 |

OTHER PUBLICATIONS

Australian Office Action, Application No. 2008248319 dated Jul. 12, 2012.
Australian Office Action, Application No. 2006291165 dated Jan. 7, 2013.
Australian Office Action, Report No. 2, Application No. 2008248319 dated Apr. 9, 2013.
Australian Office Action, Application No. 2007272947 dated May 21, 2012.
Australian Office Action, Application No. 2007314212 dated Apr. 29, 2013.
Australian Office Action Application No. 2008282318 dated Feb. 7, 2013.
Australian Office Action, Application No. 2008266014 dated Jul. 6, 2012.
Australian Office Action, Application No. 2007205257 dated Jul. 16, 2012.
Australian Office Action, Application No. 2006291165 dated Sep. 12, 2012.
Australian Office Action, Application No. 2007314212 dated Aug. 28, 2012.
Australian Office Action, Application No. 2007227423 dated Apr. 13, 2012.
Australian Office Action Application No. 2007205257 dated Feb. 26, 2013.
Australian Office Action, Application No. 2007205163 dated Nov. 15, 2012.
Australian Office Action, Application No. 2007205234 dated Sep. 20, 2011.
Australian Office Action, Application No. 2007205257 dated Dec. 22, 2011.
Australian Office Action, Application No. 2006291165 dated Aug. 23, 2011.
Australian Office Action, Application No. 2008262252 dated Feb. 15, 2013.
Australian Office Action, Application No. 2006291165 dated Feb. 13, 2012.
Australian Patent Examination Report No. 1, Appln. No. 2009219197, Dated Sep. 19, 2013.
Australian Patent Examination Report No. 1, Appln. No. 2008310704, Dated Jun. 24, 2013.
Australian Patent Examination Report No. 2, Appln. No. 2007346101, Dated May 24, 2013.
Australian Patent Examination Rpt., No. 1., 2008316577 dated Feb. 11, 2013.
Australian Patent Examination Report No. 1, Appln. No. 2008283997 Dated Aug. 20, 2007.

(56) References Cited

OTHER PUBLICATIONS

Canadian Intellectual Property Office, Requisition by the Examiner, Application 2,621,441 dated Apr. 8, 2013.
Canadian Intellectual Property Office, Requisition by the Examiner, Application No. 2,635,616, Dated Feb. 21, 2011.
Canadian Intellectual Property Office, Requisition by the Examiner, Application No. 2,646,051, dated Feb. 25, 2011.
Canadian Office Action, Application No. 2,617,581, dated Feb. 1, 2011.
Canadian Office Action, Application No. 2,621,441, dated Feb. 1, 2011.
Canadian Office Action, Application No. 2,635,616, dated Feb. 27, 2012.
Canadian Office Action, Application No. 2,617,581, dated Apr. 2, 2012.
Chinese 1st Office Action Appln. No. 201080059339.9 dated Aug. 26, 2013.
Chinese 1st Office Action, Appln. No. 200780005791.5, dated Mar. 24, 2011.
Chinese 1st Office Action, Appln. No. 200980135456.6, dated Nov. 13, 2012.
Chinese 1st Office Action, Appln. No. 200880108689.2, dated Feb. 13, 2012.
Chinese 1st Office Action, Appln. No. 200880025276.8, dated Nov. 23, 2011.
Chinese 1st Office Action, Appln. No. 200980112966.1, dated Sep. 1, 2012.
Chinese 1st Office Action, Appln. No. 200880112581.0, Aug. 13, 2012.
Chinese 1st Office Action, Appln. No. 201210312507.1, dated Jul. 29, 2013.
Chinese 1st Office Action, Appln. No. 200980113258, dated Mar. 13, 2013.
Chinese 1st Office Action, Appln. No. 201110319534.7, dated Jun. 8, 2013.
Chinese 1st Office Action, Application No. 200780018496.3 dated Mar. 22, 2011.
Chinese 1st Office Action, Application No. 200780023093.8 dated Dec. 27, 2010.
Chinese 1st Office Action, Appln. No. 200980126520.4, dated Dec. 4, 2012.
Chinese 1st Office Action, Appln. No. 200980155340.9 dated Jan. 21, 2013.
Chinese 2nd OA—EnglishTrans, Appln. No. 200880112581.0, datedMay 10, 2013.
Chinese 2nd Office Action Appln. No. 200880025276.8 dated Aug. 1, 2012.
Chinese 2nd Office Action, Appln. No. 200980112966.1, dated May 9, 2013.
Chinese 2nd Office Action, Application No. 200780040146.7 dated Dec. 31, 2011.
Chinese 2nd Office Action, Application No. 200780005821.2 dated Apr. 1, 2012.
Chinese 2nd Office Action, Application No. 200780023093.8 dated Dec. 9, 2011.
Chinese 2nd Office Action Appln. No. 200980126520.4 dated Aug. 14, 2013.
Chinese 2nd Office Action, Application No. 200780018496.3 dated Mar. 1, 2012.
Chinese 2nd Office Action, Appln. No. 200980155340.9, dated Aug. 26, 2013.
Chinese 2nd Office Action Application No. 200980111708.1 dated May 20, 2013.
Chinese 2nd Office Action, Appln. No. 200980135456.6 dated Aug. 1, 2013.
Chinese 2nd Office Action, Appln. No. 200880119206.9, dated Feb. 1, 2013.
Chinese 2nd Office Action, Appln. No. 200880003736.7 dated Nov. 5, 2012.
Chinese 2nd Office Action, Appln. No. 200780005791.5, dated May 3, 2012.
Chinese 2nd Office Action, Appln. No. 200880103023.8 dated Jun. 20, 2013.
Chinese 3rd Office Action, Appln. No. 200880108689.2, dated Apr. 1, 2013.
Chinese 3rd Office Action, Application No. 200780023093.8 dated Jul. 2, 2012.
Chinese 3rd Office Action, Application No. 200880003736.7 dated Apr. 12, 2013.
Chinese 3rd Office Action, Application No. 200780040146.7 dated Apr. 25, 2012.
Chinese 3rd Office Action, Appln. No. 200880119206.9 dated Aug. 12, 2013.
Chinese 3rd Office Action, Application No. 200880116343.7 dated Apr. 8, 2013.
Chinese 3rd Office Action, Application No. 200780005821.2 dated Nov. 5, 2012.
Chinese 3rd OfficeAction, Appln. No. 200780005791.5, dated Dec. 5, 2012.
Chinese 4th Office Action, Application No. 200780023093.8 dated Jan. 14, 2013.
Chinese 4th Office Action Appln. No. 200880116343.7 dated Jul. 10, 2013.
Chinese 4th Office Action, Application No. 200780040146.7 dated Nov. 23, 2012.
Chinese 4th Office Action Application No. 200780005821.2 dated May 13, 2013.
Chinese 5th Office Action, Application No. 200780040146.7 dated Apr. 16, 2013.
Chinese Office Action Application No. 200880022612.3 dated May 17, 2013.
Chinese Office Action, Application No. 200780040146.7 dated May 25, 2011.
Chinese Office Action, Application No. 200880116343.7 dated Oct. 22, 2012.
Chinese Office Action, Application No. 200880022612.3 dated Oct. 29, 2012.
Chinese Office Action, 1st Application No. 200880022612.3 dated Apr. 24, 2012.
Chinese Office Action, Application No. 200880116343.7 dated Jan. 31, 2012.
Chinese Office Action, Application No. 200780033066.9 dated Jun. 26, 2012.
Chinese Office Action, Application No. 200980111708.1 dated Aug. 27, 2012.
Chinese Office Action, Application No. 200880108625.2 dated Jan. 5, 2013.
Chinese Office Action, Application No. 200880112585.9 dated Jan. 21, 2013.
Chinese Office Action, Application No. 200680036598.3 dated Feb. 24, 2011.
Chinese Office Action, Application No. 200780018496.3 dated Sep. 5, 2012.
Chinese Office Action, Application No. 200880108625.2 dated Aug. 21, 2012.
Chinese Office Action, Application No. 200780005821.2 dated Jan. 26, 2011.
Chinese Office Action Application No. 200880108625.2 dated Feb. 13, 2012.
Chinese Office Action 1st Application No. 200780033066.9 dated Sep. 18, 2011.
Chinese Office Action 3rd Application No. 200780033066.9 dated Dec. 17, 2012.
Chinese Office Action, Application No. 200880112585.9 dated May 24, 2012.
Chinese Office Action, Application No. 200880119206 dated May 3, 2012.
Chinese Office Action, Application No. 200880108689.2 dated Sep. 12, 2012.
Chinese Office Action, Application No. 200680039776.8 dated Jun. 30, 2011.

(56) References Cited

OTHER PUBLICATIONS

Chinese Office Action, Application No. 200980112966.1 dated Sep. 20, 2012.
Chinese Office Action, Application No. 200880103023.8 dated Oct. 9, 2012.
Chinese Rejection Decision Appln. No. 200780033066.9 dated Jun. 13, 2013.
Communication Concerning Office Action Received from Japanese Patent Office dated Dec. 12, 2012, Japanese Patent Application No. 2008-549555.
Communication Concerning Office Action Received from Japanese Patent Office dated Jan. 30, 2012, Japanese Patent Application No. 2008-531200.
EP Communication Appln. No. 11170608.1 dated May 3, 2012.
EP Communication Appn. No. 08782609.5 dated May 24, 2012.
EP Communication Appln, No. 12154343.3 dated Jul. 10, 2012.
EP Communication Appln. No. 08796821.0 dated Jul. 19, 2013.
EP Communication Appln. No. 09715356.3 dated Jul. 10, 2013.
EP Communication Appln. No. 12154350.8 dated Jan. 25, 2013.
EP Communication Appln. No. 08782609.5 dated Jun. 24, 2011.
EP Communication Pursuant to Article 94-3, Appln. No. 12185438.4 dated Sep. 18, 2013.
EP Communication Pursuant to Article 94-3, Appln. No. 11151771.0, dated Jan. 3, 2013.
EP Communication Pursuant to Article 94-3, Appln. No. 12154307.8 dated Feb. 20, 2013.
EP Communication Pursuant to Article 94-3, Appln. No. 11151769.4, dated Jan. 3, 2013.
EP Communication Pursuant to Article 94-3, Appln. No. 12154350.8 dated Aug. 21, 2013.
EP Communication Pursuant to Article 94-3, Appln. No. 12165748.0, dated Sep. 17, 2013.
EP Communication Pursuant to Article 94-3, Appln. No. 12165734.0 datedAug. 14, 2013.
EP Communication, 09713926.5 dated Jul. 30, 2012.
EP Communication, Appln. No. 08768266.2 dated Jul. 29, 2010.
EP Communication, Appln. No. 12154304.5, dated Feb. 25, 2013.
EP Communication, Appln. No. 07867402.5 dated Dec. 11, 2009.
EP Examination Report, Application No. 12154346.6 dated Jun. 27, 2013.
EP Examination Report 08770974.7 dated Feb. 25, 2013.
EP Examination Report, Application No. 09715064.3 dated Nov. 5, 2012.
EP Extended Srch Rpt., 12185446.7 dated Mar. 28, 2013.
EP Search Report Appln, No. 12154307.8, dated Jun. 26, 2012.
EP Search Report, 12154300.3, dated Jan. 7, 2013.
EP Search Report, Application No. 11196253.6 dated Apr. 24, 2012.
EP Search Report, Application No. 12154337.5 dated Oct. 2012.
EP Search Report, Application No. 12154339.1 dated Oct. 9, 2012.
EP Search Report, Application No. 12154345.8 dated Sep. 19, 2012.
EP Search Report, Application No. 12154346.6 dated Oct. 23, 2012.
EP Search Report, Application No. 12154349.0 dated Sep. 27, 2012.
EP Search Report, Application No. 12154352.4 dated Oct. 12, 2012.
EP Search Report, Application No. 12154351.6 dated Oct. 15, 2012.
EP Search Report, Application No. 09830750.7 dated Aug. 27, 2012.
EP Search Report, Application No. 12154344.1 dated Sep. 19, 2012.
EP Search Report, Application No. 11196256.9 dated Feb. 28, 2012.
EP Search Report, Application No. 12154304.5 dated Jun. 26, 2012.
EP Search Report, Application No. 12154342.5 dated Jul. 6, 2012.
EP Search Report, Application No. 11196250.2 dated Apr. 24, 2012.
EP Search Report, Application No. 09715356.3 dated Jul. 12, 2012.
EP Search Report, Application No. 11196190.0 dated Apr. 24, 2012.
EP Search Report, Application No. 12154353.2 dated Oct. 15, 2012.
EP Search Report, Application No. 12154321.9 dated Jul. 20, 2012.
EP Search Report, Application No. 12154298.9 dated Jun. 4, 2012.
EP Search Report, Application No. 12154334.2 dated Sep. 21, 2012.
EP Search Report, Application No. 12154332.6 dated Sep. 21, 2012.
EP Search Report, Application No. 08782609.5 dated Oct. 28, 2010.
EP Search Report, Application No. 12154329.2 dated Sep. 19, 2012.
EP Search Report, Application No. 12154354.0 dated Oct. 12, 2012.
EP Search Report, Application No. 11196254.4 dated Feb. 2012.
EP Search Report, Application No. 12165748.0 dated Aug. 23, 2012.
EP Search Report, Application No. 12165734.0 dated Aug. 27, 2012.
EP Search Report, Application No. 12154300.3 dated Aug. 20, 2012.
EP Search Report, Application No. 12165740.7 dated Aug. 27, 2012.
EP Search Report, Application No. 12154301.1 dated Aug. 22, 2012.
EP Search Report, Application No. 11196261.9 dated Feb. 28, 2012.
EP Search Report, Application No. 11196264-3 dated Feb. 28, 2012.
EP Search Report, Application No. 12165636.7 dated Sep. 25, 2012.
EP Search Report, Application No. 12154326.8 dated Sep. 6, 2012.
EP Search Report, Application No. 12154341.7 dated Aug. 9, 2013.
EP Search Report, Application No. 11196262.7 dated Feb. 28, 2012.
EP Search Report, Application No. 09807241.6 dated Dec. 6, 2012.
EP Search Report, Application No. 12154348.2 dated Oct. 9, 2012.
EP Search Report, Application No. 12154322.7 dated Aug. 29, 2012.
EP Search Report, Application No. 12154327.6 dated Sep. 19, 2012.
EP Search Report, Application No. 12154350.8 dated Sep. 27, 2012.
EP Search Report, Application No. 12154347.4 dated Sep. 27, 2012.
EP Search Report, Application No. 11196265.0 dated Mar. 5, 2012.
European Communication Pursuant to Article 94(3) EPC, Application No. 06800599.0 dated Nov. 25, 2011.
European Communication Pursuant to Article 94(3) EPC, Application No. 07717903.4 dated Jan. 29, 2010.
European Communication Pursuant to Article 94-3 Appln. No. 08799295.4 dated Dec. 10, 2012.
European Communication Pursuant to Article 94(3) EPC, Application No. 07716208.9, dated Sep. 13, 2011.
European Communication Pursuant to Article 94(3) EPC, Application No. 07716208.9 dated Apr. 20, 2010.
European Communication Pursuant to Article 94(3) EPC, Application No. 07716208.9 dated Sep. 27, 2010.
European Communication Pursuant to Article 94(3) EPC, Application No. 07716208.9 dated Sep. 13, 2012.
European Communication Pursuant to Article 94(3) EPC, Application No. 08767439.6, dated Feb. 12, 2011.
European Communication Pursuant to Article 94(3) EPC, Application No. 07867402.5, dated Apr. 10, 2012.
European Communication Pursuant to Article 94(3) EPC, Application No. 08796821.0, dated Jan. 7, 2013.
European Communication Pursuant to Article 94(3) EPC, Application No. 08767439.9, dated Mar. 15, 2011.
European Communication Pursuant to Article 94(3) EPC, Application No. 08799295.4, dated Nov. 18, 2011.
European Communication Pursuant to Article 94(3) EPC, Application No. 08768266.2, dated Apr. 18, 2011.
European Communication Pursuant to Article 94(3)EPC, Application No. 06814375.9 dated Oct. 14, 2011.
European Communication Pursuant to Article 94(3) EPC, Application No. 07717903.4 datedAug. 16, 2011.
European Communication Pursuant to Article 94(3) EPC, Application No. 07867402.5, dated Jan. 5, 2011.
European Communication Pursuant to Article 94(3) EPC, Application No. 09830750.7, dated Apr. 18, 2013.
European Communication Pursuant to Article 94(3) EPC, Application No. 08841700.1, dated Jun. 1, 2012.
European Communication Pursuant to Article 94(3) EPC, Application No. 07810382.7, dated Dec. 8, 2010.
European Communication Pursuant to Article 94(3) EPC, Application No. 07717903.4, dated Apr. 25, 2012.
European Communication, Application No. 07776079.1, dated Sep. 6, 2011.
European Examination Rpt., 11196265.0, dated Feb. 22, 2013.
European Patent Application, EP 1795203 A2, Croce et al., Application No. 06010581.4, filed Feb. 7, 1997, published Jun. 13, 2007.
European Seach Report, Application No. 09714868.8 dated Aug. 1, 2011.
European Seach Report, Application No. 11151749.6, dated Feb. 8, 2011.
European Search Reoprt, Application No. 08841700.1, dated Jan. 4, 2011.
European Search Report, Application No. 07753450.1 dated Jan. 12, 2009.

(56) References Cited

OTHER PUBLICATIONS

European Search Report, Application No. 07867402.5 dated Mar. 16, 2010.
European Search Report, Application No. 07810382.7 dated Sep. 14, 2009.
European Search Report, Application No. 06825457.2 dated Sep. 16, 2009.
European Search Report, Application No. 08770974.4, dated Oct. 21, 2011.
European Search Report, Application No. 08841700.1 dated Jun. 2, 2010.
European Search Report, Application No. 11151769-4, dated Feb. 8, 2011
European Search Report, Application No. 08713330.2, dated Jul. 22, 2011.
European Search Report, Application No. 08796821.0 dated Aug. 4, 2010.
European Search Report, Application No. 09713926.5 dated Jul. 21, 2011.
European Search Report, Application No. 11151771-0, dated Feb. 8, 2011.
European Search Report, Application No. 11151772-8, dated Feb. 8, 2011.
European Search Report, Application No. 06814375.9 dated Oct. 8, 2009.
European Search Report, Application No. 08799295.4-2402, PCT/US2008/075565, dated Nov. 9, 2010.
European Search Report, Application No. 12185440.0 dated Apr. 12, 2013.
European Search Report, Application No. 07717734.3 dated Nov. 9, 2009.
European Search Report, Application No. 07717903.4 dated Oct. 23, 2009.
European Search Report, Application No. 08798444.9-2402, PCT/US2008/073964, dated Dec. 16, 2010.
European Search Report, Application No. 07716208.9 dated Nov. 10, 2009.
European Search Report, Application No. 07872618.9 dated Jul. 5, 2010.
European Search Report, Application No. 08767439.6 dated May 12, 2010.
European Search Report, Application No. 08768266.2 dated Jul. 1, 2010.
European Search Report, Application No. 06800599.0 dated Oct. 19, 2009.
European Srch Rpt. 08838376.5 dated Mar. 4, 2011.
European Srch Rpt., 09763590.8 dated Aug. 29, 2011.
European Supplementary Search Report, Application No. 09715064.3 dated May 24, 2011.
Ext. Srch Rpt., Appln. No. 12154246.8 dated Jun. 4, 2012.
Extended EP Search Rpt., Appln. No. 12154353.2 dated Jan. 31, 2013.
Extended EP Search Report Appl. No. 12179595.9 dated Jan. 23, 2013.
Extended EP Search Report Appl. No. 12185438.4 dated Mar. 28, 2013.
Extended EP Search Report 12179592.6 dated Jan. 21, 2013.
Extended EP Srch Rpt., Appln. No. 12165748.0.
Extended EP Srch Rpt., Appln. No. 12154351.6 dated Jan. 31, 2013.
Extended EP Srch Rpt., Appln. No. 12154301.1, dated Jan. 11, 2013.
Extended EP Srch Rpt., Appln. No. 12154354.0 dated Jan. 28, 2013.
Extended EP Srch Rpt., Appln. No. 12165734.0 dated Jan. 11, 2013.
Extended EP Srch Rpt., Appln. No. 12165740.7 dated Jan. 11, 2013.
Extended EP Srch Rpt., Appln. No. 12154352.4, dated Jan. 28, 2013.
Extended European Search Report, Appln. No. 12154300.3.
Extented EP Search Rpt., Appln. No. 12154349.0 dated Jan. 25, 2013.
Japanese Notification of Reasons for Rejection 2009-519525 dated Nov. 1, 2012.
Japanese Notification Reason for Rejection—EnglishTrans, 2010-512377 dated Jun. 4, 2013.
Japanese Notification of Reasons for Rejection, 2010548907 dated Sep. 2, 2013.
Japanese Notification of Reasons for Rejection, 2010548904, dated Sep. 2, 2013.
Japanese Notification of Reasons for Rejection 2010522058 dated Aug. 13, 2013.
Japanese Notification of Reasons for Rejection 2010529072 dated Jul. 30, 2013.
Japanese Notification Reasons for Rejection 2009-529212 dated Jul. 19, 2013.
Japanese Notification Reasons for Rejection 2010-519269 dated Jul. 12, 2013.
Japanese Notification of Reasons for Rejection, 2009-519525 dated Jul. 9, 2012.
Japanese Notification of Reasons for Rejection, Appln. No. 2010-548899, dated Oct. 8, 2013.
Japanese Notification of ReasonsFor Rejection 2010-524221 dated Jun. 19, 2013.
Japanese Notification of Reasons for Rejection 2009548281 dated Sep. 3, 2013.
Japanese Office Action dated Feb. 22, 2012, Japanese Patent Application No. 2008-549549.
Japanese Office Action, Application No. 2010-511218 dated Jun. 3, 2013.
Japanese Office Action dated Feb. 24, 2012, Japanese Patent Application No. 2008-549532.
Japanese Office Action dated Feb. 24, 2012, Japanese Patent Application No. 2008-549555.
Japanese Office Action dated Jan. 4, 2012, Japanese Patent Application No. 2008-5251070.
Japanese Office Action, Application No. 2010-506300 dated Apr. 16, 2013.
Japanese Office Action 2008-525107 dated Jan. 4, 2011.
Japanese Office Action, Application No. 2008-525107 dated Oct. 19, 2012.
Japanese Office Action, Application No. 2009-529212 dated Oct. 17, 2012.
Japanese Office Action, Application No. 2009-535366 Dec. 21, 2012.
Japanese Office Action, Application No. 2009-501495 dated Jul. 27, 2012.
Notice of Allowance and Fees Due in U.S. Appl. No. 12/160,064, filed Jul. 3, 2008, mailing date Nov. 20, 2009.
Notice of Allowance and Fees Due in U.S. Appl. No. 12/298,221, filed Nov. 10, 2008, mailing date Nov. 30, 2009.
Office Action issued in U.S. Appl. No. 12/160,064, filed Jul. 3, 2008, mailing date Aug. 10, 2009.
Office Action issued in U.S. Appl. No. 12/293,471, filed Oct. 9, 2008, mailing date Jun. 8, 2010.
Office Action issued in U.S. Appl. No. 12/373,358, filed Feb. 11, 2009, mailing date Aug. 20, 2010.
Office Action issued in U.S. Appl. No. 12/442,018, filed Mar. 27, 2009, mailing date Apr. 15, 2010.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Oct. 30, 2009.
Office Action issued in U.S. Appl. No. 12/083,067, filed Jun. 20, 2008, mailing date Jul. 8, 2010.
Office Action issued in U.S. Appl. No. 12/160,034, filed Jul. 8, 2008, mailing date Jun. 7, 2010.
Office Action issued in U.S. Appl. No. 12/160,061, filed Jul. 3, 2008, mailing date Apr. 24, 2009.
PCT International Preliminary Report on Patentability, PCT/US2008/079482 filed Oct. 10, 2008, dated Apr. 13, 2010.
PCT International Preliminary Report on Patentability, PCT/US2010/025173 filed Feb. 24, 2010, dated Sep. 9, 2011.
PCT International Preliminary Report on Patentability, PCT/US2009/035463 filed Feb. 27, 2009, dated Aug. 31, 2010.
PCT International Preliminary Report on Patentability, PCT/US2011/034451 filed Apr. 29, 2011, dated Nov. 15, 2012.

(56) References Cited

OTHER PUBLICATIONS

PCT International Preliminary Report on Patentability, PCT/US2009/035482 filed Feb. 27, 2009, dated Aug. 31, 2010.
PCT International Preliminary Report on Patentability, PCT/US2006/038824 filed Oct. 4, 2006, dated Apr. 9, 2008.
PCT International Preliminary Report on Patentability, PCT/US2006/029889 filed Jul. 31, 2006, Feb. 5, 2008.
PCT International Preliminary Report on Patentability, PCT/US2007/006824 filed Mar. 19, 2007, dated Sep. 23, 2008.
PCT International Preliminary Report on Patentability, PCT/US2007/020215 filed Sep. 17, 2007, dated Mar. 24, 2009.
PCT International Preliminary Report on Patentability, PCT/US2009/038214 filed Mar. 25, 2009, dated Jun. 16, 2011.
PCT International Preliminary Report on Patentability, PCT/US2009/065072 filed Nov. 19, 2009, dated Jun. 3, 2011.
PCT International Preliminary Report on Patentability, PCT/US2008/075565 filed Sep. 8, 2008, dated Mar. 9, 2010.
PCT International Preliminary Report on Patentability, PCT/US2008/073964 filed Aug. 22, 2008, dated Feb. 24, 2010.
PCT International Preliminary Report on Patentability, PCT/US2007/009910 filed Apr. 24, 2007, dated Oct. 28, 2008.
PCT International Preliminary Report on Patentability, PCT/US2007/000024 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2006/035100 filed Sep. 11, 2006, dated Mar. 18, 2008.
PCT International Preliminary Report on Patentability, PCT/US2007/000103 filed Jan. 3, 2007, dated Jul. 8, 2008.
PCT International Preliminary Report on Patentability, PCT/US2008/001157 filed Jan. 29, 2008, dated Aug. 4, 2009.
PCT International Preliminary Report on Patentability, PCT/US2007/023660 filed Nov. 1, 2007, dated May 5, 2009.
PCT International Preliminary Report on Patentability, PCT/US2008/072081 filed Aug. 4, 2008, dated Feb. 9, 2010.
PCT International Preliminary Report on Patentability, PCT/US2008/005503 filed Apr. 29, 2008, dated Nov. 3, 2009.
PCT International Preliminary Report on Patentability, PCT/US2010/057758 filed Nov. 23, 2010, dated Jun. 7, 2012.
PCT International Preliminary Report on Patentability, PCT/US2008/071532 filed Jul. 30, 2008, dated Feb. 2, 2010.
PCT International Preliminary Report on Patentability, PCT/US2009/035458 filed Feb. 27, 2009, dated Aug. 31, 2010.
PCT International Preliminary Report on Patentability, PCT/US2007/015892 filed Jul. 12, 2007, dated Jan. 13, 2009.
PCT International Preliminary Report on Patentability, PCT/US2008/081294 filed Oct. 27, 2008, Apr. 27, 2010.
PCT International Preliminary Report on Patentability, PCT/US2009/035470 filed Feb. 27, 2009, dated Aug. 31, 2010.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.
PCT International Search Report and the Written Opinion, PCT/US2008/71532 filed Jul. 30, 2008, dated Apr. 17, 2009.
PCT International Search Report and the Written Opinion, PCT/US2009/46999 filed Jun. 11, 2009, dated Nov. 23, 2009.
PCT International Search Report and the Written Opinion, PCT/US2008/73964 filed Aug. 22, 2008, dated Dec. 24, 2008.
PCT International Search Report and the Written Opinion, PCT/US2009/65072 filed Nov. 19, 2009, dated Mar. 3 2010.
PCT International Search Report and the Written Opinion, PCT/US2007/00159 filed Jan. 3, 2007, dated Apr. 11, 2008.
PCT International Search Report and the Written Opinion, PCT/US2009/53586 filed Aug. 12, 2009, dated Oct. 28, 2009.
PCT International Search Report and the Written Opinion, PCT/US2007/006824 filed Mar. 19, 2007, dated May 14, 2008.
PCT International Search Report and the Written Opinion, PCT/US2006/29889 filed Jul. 31, 2006, dated Jul. 10, 2007.
PCT International Search Report and the Written Opinion, PCT/US2007/15892 filed Jul. 12, 2007, dated Sep. 30, 2008.
PCT International Search Report and the Written Opinion, PCT/US2007/00103 filed Jan. 3, 2007, dated Dec. 3, 2007.
PCT International Search Report and the Written Opinion, PCT/US2010/025173 filed Feb. 24, 2010, dated Jul. 6, 2010.
PCT International Search Report and the Written Opinion, PCT/US2008/66870 filed Jun. 13, 2008, dated Nov. 10, 2008.
PCT International Search Report and the Written Opinion, PCT/US2012/28016 filed Mar. 7, 2012, dated Aug. 3, 2012.
PCT International Search Report and the Written Opinion, PCT/US2012/020911 filed Jan. 11, 2012, dated Apr. 25, 2012.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2006/38824 filed Oct. 4, 2006, dated Aug. 9, 2007.
PCT International Search Report and the Written Opinion, PCT/US2012/060225 filed Oct. 15, 2012, dated Jan. 7, 2013.
PCT International Search Report and the Written Opinion, PCT/US2008/07196 filed Jun. 9, 2008, dated Nov. 19, 2008.
PCT International Search Report and the Written Opinion, PCT/US2008/72081 filed Aug. 4, 2008, dated Jan. 14, 2009.
PCT International Search Report and the Written Opinion, PCT/US2007/006824 filed Mar. 19, 2007, dated Mar. 3, 2008.
PCT International Search Report and the Written Opinion, PCT/US2008/01157 filed Jan. 29, 2008, dated Aug. 7, 2008.
PCT International Search Report and the Written Opinion, PCT/US2007/20215 filed Sep. 17, 2007, dated Jul. 25, 2008.
PCT International Search Report and the Written Opinion, PCT/US2009/38214 filed Mar. 25, 2009, dated Aug. 14, 2009.
PCT International Search Report and the Written Opinion, PCT/US2008/05503 filed Apr. 29, 2008, dated Sep. 25, 2008.
PCT International Search Report and the Written Opinion, PCT/US2007/09910 filed Apr. 24, 2007, dated Feb. 13, 2008.
PCT International Search Report and the Written Opinion, PCT/US2007/23660 filed Nov. 1, 2007, dated Sep. 16, 2008.
PCT International Search Report and the Written Opinion, PCT/US2007/00024 filed Jan. 3, 2007, dated Nov. 2007.
PCT International Search Report and the Written Opinion, PCT/US2006/35100 filed Sep. 11, 2006, dated Sep. 5, 2007.
PCT International Search Report and the Written Opinion, PCT/US2008/84821 filed Nov. 26, 2008, dated Feb. 17, 2009.
PCT Intr Srch Rpt., Written Opinion, PCT/US12/62853, dated Mar. 14, 2013.
PCT Invitation to Pay Additional Fees, PCT/US2012/028016 filed Mar. 7, 2012, dated May 29, 2012.
PCT Search Report and Written Opinion PCT/US2012/67651, dated May 13, 2013.
PCT Search Report and Written Opinion, PCT/US13/22492, dated May 20, 2013.
PCT Search Report and Written Opinion PCT/US2012/68736, dated Apr. 8, 2013.
PCT Srch Rpt. Wrtn. Opin, PCT-US12-69484, dated Apr. 29, 2013.
PCT Srch Rpt., Written Opinion, PCT/US11/29348, dated Jun. 3, 2011.
PCT Srch Rpt., Wrtn Opin PCT/US12/62853 dated Mar. 14, 2013.
PCT Srch Rpt., Wrtn Opin PCT/US13/538930 dated Feb. 10, 2012.
PCT Srch Rpt., Wrtn Opin, PCT/US11/41046, dated Mar. 15, 2012.
PCT Written Opinion PCT/US13/538930 dated May 23, 2013.

(56) References Cited

OTHER PUBLICATIONS

Ahmad, A. et al., "Distant Metastases of Nasopharyngeal Carcinoma: A Study of 256 Male Patients," Journal of Surgical Oncology, 1986, pp. 194-197, vol. 33.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Akahoshi, M. et al., "Myeloproliferative Disorders Terminating in Acute Megakaryoblastic Leukemia with Chromosome 3q26 Abnormality," Cancer, 1987, pp. 2654-2661, vol. 60.
Akao, Y. et al., "let-7 MicroRNA Functions as a Potential Growth Suppressor in Human Colon Cancer Cells," Biol. Pharm. Bull., May 2006, pp. 903-906, vol. 29, No. 5.
Alberts, B. et al., Molecular Biology of the Cell, 3rd Edition, 1994, p. 465.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Ambros, MicroRNA Pathways in Flies and Worms: Growth, Death, Fat, Stress, and Timing, Nature, 2004, vol. 431, pp. 350-355.
Ambros, V. et al., "A Uniform System for MicroRNA Annotation," RNA, 2003, pp. 277-279, vol. 9.
Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.
Andriani, Increased Sensitivity to Cisplatin-Neoplasia, vol. 8, No. 1, pp. 9-17.
Aqeilan, R. I. et al., "Targeted Deletion of WWOX Reveals a Tumor Suppressor Function," PNAS, Mar. 2007, pp. 3949-3954, vol. 104, No. 10.
Arata, et al., Cdk2-dependent and -independent Pathways in E2F-mediated S Phase Induction, J. Biol. Chem, 2000.
Asangani, IA et al., MicroRNA-21 (miR-21) post-transcriptionally downregulates tumor suppressor Pdcd4 and stimulates invasion, intravasation and metastasis in colorectal cancer, Oncogene, 2008, vol. 27, pp. 2128-2136.
Attwooll, et al., The E2F family: specific functions and overlapping interests, EMBO, 2004.
Baira, E. et al., "Ultraconserved Elements: Genomics, Function and Disease," RNA Biology, Jul. 2008, pp. 132-134, vol. 5, No. 3.
Bakkus, M. et al., "MicroRNA Expression Analysis in Multiple Myeloma Plasma Cells and Cell Lines by a Quantitative Real-Time PCR Approach," Blood, 2007, p. 729A, vol. 110, No. 11, Abstract.
Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.
Bao, B. et al. Anti-Tumor Activity of a Novel Compound, PLOS One, 2011, vol. 6, Issue 3, pp. 1-12.
Barad, O. et al., "MicroRNA Exrpession Detected by Oligonucleotide Microarrays: System Establishment and Expression Profiling in Human Tissues," Genome Research, 2004, pp. 2846-2494, vol. 14.
Bartel, D. P., "MicroRNAs: Target Recognition and Regulatory Functions," Cell, Jan. 2009, pp. 215-233, vol. 136.
Bartel, MicroRNAs: Genomics, Biogenesis, Mechanism, and Function, Cell, vol. 116, 2004, pp. 281-297.
Basu, et al., MicroRNA-375 and MicroRNA-221:Potential Noncoding RNAs Associated with Antiproliferative Activity of Benzyl Isothiocyanate in Pancreatic Cancer, Croce, Genes & Cancer, 2011, pp. 108-119.
Bednarek, A. K. et al., "WWOX, the FRA16D Gene, Behaves as a Suppressor of Tumor Growth," Cancer Research, Nov. 2001, pp. 8068-8073, vol. 61.
Bejenaro, etal., "Ultraconserved Elements in the Human Genome," Electronic Suppl. Data, Science, 2004.
Bejerano, Computational Screening of Conserved Genomic DNA-Nature Methods, 2005, vol. 2, No. 7, pp. 535-545.
Bejerano, G. et al., "Ultraconserved Elements in the Human Genome," Science, May 2004, pp. 1321-1325, vol. 304.
Belinsky, et al., Inhibition of DNA Methylation and Histone Deacetylation Prevents Murine Lung Cancer, Cancer Research 63, 2004, pp. 7089-7093.
Bell, D. A., "Origins and Molecular Pathology of Ovarian Cancer," Modern Pathology, 2005, pp. S19-S32, vol. 18.
Bendoraite., et al, Regulation of miR-200 family microRNAs and ZEB transcription factors in ovarian cancer: evidence supporting a mesothelial-toepithelial transition, Gyneol Oncol, 2010, vol. 116, pp. 117-125.
Bichi, R. et al., "Human Chronic Lymphocytic Leukemia Modeled in Mouse by Targeted TCL1 Expression," PNAS, May 2002, pp. 6955-6960, vol. 99, No. 10.
Bloomston, et al., Identification of Molecular Markers Specific for Pancreatic Neuroendocrine Tumors by Genetic Profiling of Core Biopsies, Ann. Surg. Oncol. 2004, vol. 11, 4, pp. 413-419.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blow, Replication licensing—defining the proliferative state, Cell Biol, 2002.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Boominathan, L., The Tumor Suppressors p53-p63 and p72, PLOS ONE, May 2010, vol. 5, Issue 5, pp. 113.
Braun et al., "p53-Responsive MicroRNAs 192 and 215 are Capable of Inducing Cell Cycle Arrest," Cancer Research, 2008, pp. 10094-10104, vol. 68.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, A. et al., "Identification of Metastasis-Related MicroRNAs in Hepatocellular Carcinoma," Hepatology, Mar. 2008, pp. 897-907, vol. 47, No. 3.
Budhu, et al., Prediction of venous metastases, recurrence, and prognosis in hepatocellular carcinoma based on a unique immune response signature of the liver microenvironment, Cancer Cell, 2006, vol. 10, 2, pp. 99-111.
Butz, H. et al., "Down-Regulation of Wee1 Kinase by a Specific Subset of MicroRNA Sporadic Pituitary Adenomas," Journal of Clinical Endocrinol Metab, Oct. 2010, pp. E181-E191, vol. 95, No. 10.
Caldas, C. et al., "Sizing Up miRNAs as Cancer Genes," Nature Medicine, Jul. 2005, pp. 712-714, vol. 11, No. 7.
Calin, G. A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "MicroRNA Signatures in Human Cancers," Nature Reviews Cancer, Nov. 2006, pp. 857-866, vol. 6.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.

(56) References Cited

OTHER PUBLICATIONS

Calin, G. A. et al., "Ultraconserved Regions Encoding ncRNAs are Altered in Human Leukemias and Carcinomas," Cancer Cell, Sep. 2007, pp. 215-229, vol. 12.

Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.

Cannistra, S.A., "Cancer of the Ovary," The New England Journal of Medicine, 2004 pp. 2519-2529, vol. 351, No. 25.

Castoldi, M. et al., "A Sensitive Array for MicroRNA Expression Profiling (miChip) Based on Locked Nucleic Acids (LNA)," RNA, 2006, pp. 913-920, vol. 12.

Chambers, et al., Dissemination and Growth of Cancer Cells in Metastatic Sites, Nat. Rev. Cancer, 2002, vol. 2, pp. 563-572.

Chan, J. A. et al., "MicroRNA-21 is an Antiapoptotic Factor in Human Glioblastoma Cells," Cancer Research, Jul. 2005, pp. 6029-6033, vol. 65, No. 14.

Chang, N.-S. et al., "Molecular Mechanisms Underlying WOX1 Activation During Apoptotic and Stress Responses," Biochemical Pharmacology, 2003, pp. 1347-1354, vol. 66.

Chang, T. C., et al., Transactivation of miR-34a by p53, Molecular Cell 26, pp. 745-752, 2007.

Chang, T.-C. et al., "Widespread MicroRNA Repression by Myc Contributes to Tumorigenesis," Nat Genet., Jan. 2008, pp. 43-50, vol. 40, No. 1.

Chen, C.-Z. et al., "MicroRNAs as Regulators of Mammalian Hematopoiesis," Seminars in Immunology, 2005, pp. 155-165, vol. 17.

Chen, et al., Expanded Polyglutamine-Binding Peptoid as a Novel Therapeutic Agent for Treatment of Huntington's Disease, Chemistry Biology, 2011, vol. 18, pp. 1113-1125.

Chen, et al., Real-time quantification of microRNAs by stem-loop RT-PCR, Nucleic Acids, 33, 2005, e179.

Chen,et al., Downregulation of miR-221/222 sensitizes glioma cells to tempzolomide by regulating apoptosis independently of p53 status, Onocolgy Reports, 2012, vol. 27, pp. 854-860.

Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.

Chim, S.S.C. et al., "Detection and Characterization of Placental MicroRNAs in Maternal Plasma," Clinical Chemistry, 2008, pp. 482-490, vol. 54, No. 3.

Chun-zhi, et al., MicroRNA-221 and microRNA-222 regulate gastric carcinoma cell proliferation and radioresistance by targeting PTEN, BMC Cancer, 2010, gastric, vol. 10, pp. 1-10.

Ciafre, S. A. et al., "Extensive Modulation of a Set of MicroRNAs in Primary Glioblastoma," Biochemical and Biophysical Research Communications, 2005, pp. 1351-1358, vol. 334.

Cillo, et al., The critical issue of hepatocellular carcinoma prognostic classification: which is the best tool available, J. Hepatol., 2004, vol. 40, 1, pp. 124-131.

Cimmino, A. et al., "miR-15 and miR-16 Induce Apoptosis by Targeting BCL2," PNAS, Sep. 2005, pp. 13944-13949, vol. 102, No. 39.

Cimmino, A. et al., Corrections to "miR-15 and miR-16 Induce Apoptosis by Targeting BCL2," PNAS, Feb. 2006, pp. 2464-2465, vol. 103, No. 7.

Costinean, S. et al., "Pre-B Cell Proliferation and Lymphoblastic Leukemia/ High-Grade Lymphoma in Eμ-miR155 Transgenic Mice," PNAS, May 2006, pp. 7024-7029, vol. 103, No. 18.

Cowgill, The genetics of pancreatic cancer Am. J. Surg, 2003, vol. 186, 3, pp. 279-286.

Croce, C. M. et al., "miRNAs, Cancer, and Stem Cell Division," Cell, 2005, pp. 6-7, vol. 36.

Croce, C. M. et al., "Role of FHIT in Human Cancer," Journal of Clinical Oncology, May 1999, pp. 1618-1624, vol. 17, No. 5.

Croce, C. M., "Causes and Consequences of MicroRNA Dysregulation in Cancer," Nature Reviews Genetics, Oct. 2009, pp. 704-714, vol. 10.

Croce, C. M., "Oncogenes and Cancer," The New England Journal of Medicine, Jan. 2008, pp. 502-511, vol. 358, No. 5.

Cui, S. et al., "MicroRNAs that Underlie Ovarian Cancer Development and Response to Chemotherapy," 98th AACR Annual Meeting, Apr. 14-18, 2007, Los Angeles, CA.

Dahiya, N. et al., "MicroRNA Expression and Identification of Putative miRNA Targets in Ovarian Cancer," Plos One, Jan. 2008, pp. 1-11, vol. 3, No. 6.

Dalmay, T. et al., "MicroRNAs and the Hallmarks of Cancer," Oncogene, 2006, pp. 6170-6175, vol. 25.

Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.

Davies, F. E. et al., "Insights into the Multistep Transformation of MGUS to Myeloma Using Microarray Expression Analysis," Blood, Dec. 2003, pp. 4504-4511, vol. 102, No. 13.

Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.

DeLott, et al., CDX2 Is a Useful Marker of Intestinal-Type Differentiation Arch. Pathol. Lab, Med, 2005 vol. 129, 9, pp. 1100-1105.

Dignam, et al., Accurate transcription initiation by RNA polymerase D in a soluble extract from isolated mammalian nuclei, Nucleic Acids Res., 11, 1983, pp. 1475-1489.

Dohner, H. et al., "Genomic Aberrations and Survival in Chronic Lymphocytic Leukemia," The New England Journal of Medicine, Dec. 2000, pp. 1910-1916, vol. 343, No. 26.

Druck, etal., "FHIT," Atlas of Genetics and Cytogenetics in Oncology and Haematology, 2007, pp. 171-178, vol. 2.

Ehrich, et al., Quantitative High-Throughput Analysis of DNA Methylation Patterns by Base-Specific Cleavage and Mass Spectrometry, vol. 102, 2005, pp. 15785-15790.

Eiriksdottir, G. et al., "Mapping Loss of Heterozygosity at Chromosome 13q: Loss at 13q12-q13 is Associated with Breast Tumour Progression and Poor Prognosis," European Journal of Cancer, 1998, pp. 2076-2081, vol. 34, No. 13.

Eis, P. S. et al., "Accumulation of miR-155 and Bic RNA in Human B Cell Lymphomas," PNAS, Mar. 2005, pp. 3627-3632, vol. 102, No. 10.

Esquela-Kerscher, A. et al., "Oncomirs—MicroRNAs with a Role in Cancer," Nature Reviews:Cancer, Apr. 2006, pp. 259-269, vol. 6.

Eychene, A. et al., "A New MAFia in Cancer," Nature Reviews Cancer, Sep. 2008, pp. 683-693, vol. 8.

Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.

Fabbri, M. et al., "WWOX Gene Restoration Prevents Lung Cancer Growth in Vitro and in Vivo," PNAS, Oct. 2005, pp. 15611-15616, vol. 102, No. 43.

Fabbri, M. et al., "MicroRNAs," The Cancer Journal, Jan./Feb. 2008, pp. 1-6, vol. 14, No. 1.

Farazi, et al., MicroRNA Sequence and Expression Analysis in Breast Tumors by Deep Sequencing, AACR, 71(13), Jul. 1, 2011, pp. 4443-4453.

Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.

Feng, G. et al., "Elevated Serum-Circulating RNA in Patients with Conventional Renal Cell Cancer," Anticancer Research, 2008, pp. 321-326, vol. 28.

Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.

Fong, Y. et al., "Muir-Torre-Like Syndrome in FHIT-Deficient Mice," PNAS, Apr. 2000, pp. 4742-4747, vol. 97, No. 9.

Ford, L.P., "A MicroRNA Expression Signature of Human Solid Tumors Defines Cancer Gene Targets," Leukemia Research, 2006, pp. 511-513, vol. 30.

(56) References Cited

OTHER PUBLICATIONS

Fornari, et al., MiR-221 controls CDKNIC/p57 and Cdknib/p27 expression in human hepatocellular carcinoma, Oncogene 2008, vol. 27, pp. 5651-5661.
Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gailiun, M., "Single MicroRNA Causes Cancer in Transgenic Mice," Research Communications, The Ohio State University, Apr. 2006, pp. 1-3.
Gang, M. et al., "Expression of Programmed Cell Death 4 and Its Clinicopathological Significance in Human Pancreatic Cancer," Abstract, 2005, pp. 597-600, vol. 27.
Garcea, et al., Molecular prognostic markers in pancreatic cancer, A systematic review, Eur. J. Cancer, 2005, vol. 4, 15, pp. 2213-2236.
Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.
Garofalo, M. et al., "MicroRNA Signatures of TRAIL Resistance in Human Non-Small Cell Lung Cancer," Oncogene, 2008, pp. 3854-3855, vol. 27.
Garzon et al., MicroRNA expression and function in cancer, Trend Mol Med, vol. 12, 2006, pp. 580-587.
Garzon et al., MicroRNA signatures associated with cytogenetics and prognosis in acute myeloid leukemia; Blood, Mar. 15, 2008, vol. 111, No. 6.
Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.
Garzon, et al., "MicroRNA Signatures Associated with Cytogenetics and Outcome in Acute Myeloid Leukemia", Blood (ASH Annual Meeting Abstracts), 2006, vol. 108, Abstract Only.
Garzon, R. et al., "MicroRNA Expression and Function in Cancer," TRENDS in Molecular Medicine, Oct. 2006, pp. 580-587, vol. 12, No. 12.
Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Garzon, R. et al., "MicroRNA Fingerprints During Human Megakaryocytopoiesis," PNAS, Mar. 2006, pp. 5078-5083, vol. 103, No. 13.
Ghaneh, et al., Molecular prognostic markers in pancreatic cancer, J. Hepatobiliary, Pancreat. Surg., 2002, vol. 9, pp. 1-11.
Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.
Goel, A., et al., A Novel Mechanism for Aspirin Mediated Growth Inhibition, Clin Cancer Res, 2003, vol. 9, pp. 383-390.
Gourley, C. et al., "WWOX Gene Expression Abolishes Ovarian Cancer Tumorigenicity in Vivo and Decreases Attachment to Fibronectin via Integrin α3," Cancer Research, Jun. 2009, pp. 4835-4842, vol. 69, No. 11.
Greenbaum, D. et al., "Comparing Protein Abundance and mRNA Expression Levels on a Genomic Scale," Genome Biology, 2003, pp. 117.1-117.8, vol. 4, Issue 9.
Gregory, et al., MicroRNA Biogenesis and Cancer, Cancer Res, 2005, vol. 65, 9, pp. 3509-3512.
Gregory, et al., The Microprocessor complex mediates the genesis of microRNAs, Nature, 432, 2004, pp. 235-240.
Grier, D.G. et al., "The Pathophysiology of HIX Genes and Their Role in Cancer," Journal of Pathology, 2005, pp. 154-171, vol. 205.

Griffiths-Jones, S. et al., "miRBase: MicroRNA Sequences, Targets and Gene Nomenclature," Nucleic Acids Research, 2006, pp. D140-D144, vol. 34.
Griffiths-Jones, S. et al., "miRBase: Tools for MicroRNA Genomics," Nucleic Acids Research, 2008, pp. D154-D157, vol. 36.
Griffiths-Jones, S., "The MicroRNA Registry," Nucleic Acids Research, 2004, pp. D109-D111, vol. 32.
Gu, et al., The t(4;11) Chromosome Translocation of Human Acute Leukemias Fuses the ALL-7 Gene, Related to *Drosophila trithorax*, to the AF-4 Gene, Cell 71, 1992, pp. 701-709.
Guenther, et al., Global and Hox-specific roles for the MLL1 methyltransferase, Proc. Natl. Acad. Sci., 102, 2005, pp. 8603-8608.
Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Habbe, et al., MicroRNA miR-155 is a biomarker of early pancreatic neoplasia, Cancer Biol Therapy, 2009, pp. 340-346.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.
He, H. et al., "The Role of MicroRNA Genes in Papillary Thyroid Carcinoma," PNAS, Dec. 2005, pp. 19075-19080, vol. 102, No. 52.
He, L. et al., "A MicroRNA Polycistron as a Potential Human Oncogene," Nature, Jun. 2005, pp. 828-833, vol. 435.
He, X. et al., "MicroRNA and Esophageal Carcinoma," Journal of Nanjing Medical University, 2007, pp. 201-206, vol. 21, No. 4.
Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.
Hezel, et al., Genetics and biology of pancreatic ductal adenocarcinoma, Genes Dev., 2006, vol. 20, pp. 1218-1249.
Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.
Hu, et al., A miR-200 microRNA cluster as prognostic marker in advanced ovarian cancer, Gynecol Oncol, 2009, vol. 114, pp. 457-464.
Huang, et al., Evaluation of predictive value of Clip, Okuda, TNM and JIS staging systems for hepatocellular carcinoma patients undergoing surgery, J. Gastroenterol Hepatol, 2005, vol. 20, 5, pp. 765-771.
Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.
Hudlebusch, H. et al., "Expression of HOXA Genes in Patients with Multiple Myeloma," Leukemia & Lymphoma, Jun. 2004, pp. 1215-1217, vol. 45, No. 6.
Hutvagner, et al., A MicroRNA in a Multiple Turnover RNAi Enzyme Complex, Science, 2002, vol. 297, 5589, pp. 2056-2060.
Iizuka, et al., Oligonucleotide microarray for prediction of early intrahepatic, Lancet, 2003, vol. 361, 9361, pp. 923-929.
Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.
Iliopoulos, D. et al., "Inhibition of Breast Cancer Growth InVitro and in Vivo: Effect of Restoration of WWOX Expression," Clin. Cancer Research, Jan. 2007, pp. 268-274, vol. 13, No. 1.
Iorio, et al., Causes and consequences of microRNA Dysregulation, Cancer Journal, 2012, vol. 18, pp. 215-222.
Iorio, M. V. et al., "MicroRNA Gene Expression Deregulation in Human Breast Cancer," Cancer Research, Aug. 2005, pp. 7065-7070, vol. 65, No. 16.
Iorio, M. V. et al., "MicroRNA Signatures in Human Ovarian Cancer," Cancer Research, Sep. 2007, pp. 8699-8707, vol. 67, No. 18.

(56) References Cited

OTHER PUBLICATIONS

Ishii, H. et al., "Effect of Adenoviral Transduction of the Fragile Histidine Triad Gene into Esophageal Cancer Cells," Cancer Research, Feb. 2001, pp. 1578-1584, vol. 61.
Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.
Izzotti, A. et al., Relationships of MicroRNA Expression in Mouse, FASEB Journal, vol. 23, Sep. 2009, pp. 3243-3250.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jacobs, I.J. et al., "Progress and Challenges in Screening for Early Detection of Ovarian Cancer," Molecular & Cellular Proteomics, 2004, pp. 355-366, vol. 3.
Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.
Jazbutyte, V. et al., "MicroNRA-21: From Cancer to Cardiovascular Disease," Current Drug Targets, Abstract, 2010, pp. 926-935, vol. 11.
Jemal, A. et al., "Cancer Statistics, 2008," CA Cancer J. Clin., 2008, pp. 71-96, vol. 58, No. 2.
Jemal, et al., Cancer Statistics, 2007, Cancer Stats vol. 57, 2007, pp. 43-66.
Ji, J. et al., "MicroRNA Expression, Survival, and Response to Interferon in Liver Cancer," The New England Journal of Medicine, Oct. 2009, pp. 1437-1447, vol. 361, No. 15.
Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.
Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.
Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.
Jiang, J. et al., "Real-Time Expression Profiling of MicroRNA Precursors in Human Cancer Cell Lines," Nucleic Acids Research, 2005, pp. 5394-5403, vol. 33, No. 17.
Johansson, et al., Hematologic malignancies with t(4;11)(q21;q23) a cytogenetic, morphologic, immunophenotypic and clinical study of 183 cases, Leukemia, 12, 1998, pp. 779-787.
John, B. et al., "Human MicroRNA Targets," PLOS Biology, Nov. 2004, pp. 1863-1879, vol. 2, Issue 11.
Johnson, S. M. et al., "RAS is Regulated by the let-7 MicroRNA Family," Cell, Mar. 2005, pp. 635-647, vol. 120.
Joost, et al., BIC and miR-155 are highly expressed in Hodgkin, primary mediastinal and diffuse large B cell lymphomas , J. Pathol., 2005, 207, pp. 243-249.
Kan, et al., Elevated Levels of Circulating MicroRNA, BMC, Cancer, 2012, vol. 12, pp. 2-9.
Kawasaki, H. et al., "MicroRNA-196 Inhibits HOXB8 Expression in Myeloid Differentiation of HL60 Cells," Nucleic Acids Symposium Series, 2004, pp. 211-212, No. 48.
Kelly, L.M. et al., "CT53518, A Novel Selective FLT3 Antagonist for the Treatment of Acute Myelogenous Leukemia (AML)," Cancer Cell, Jun. 2002,pp. 421-432, vol. 1.
Kim, et al., FHIT Protein Enhances Paclitaxel-Induced Apoptosis, Int. J. Cancer, vol. 118, pp. 1692-1698, Apr. 1, 2006.
Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.
Kim, MicroRNA Biogenesis: Coordinated Cropping and Dicing , Nature Rev. Mol. Cell Bio, vol. 6, 2005, pp. 376-385.
Kim, Processing of intronic microRNAs, EMBO, 2007, vol. 26, 3, pp. 775-783.
Kluiver, et al., BIC and miR-155 are highly expressed in Hodgkin, primary mediastinal and diffuse large B cell lymphomas, J. Pathol., 2005, 207, 2, pp. 243-249.
Kluiver, et al., Lack of BIC and MicroRNA miR-155 Expression in Primary Cases of Burkitt Lymphoma, Cancer, 2006, vol. 45, 2, pp. 147-153.
Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.
Koturbash, I. et al., "Role of Epigenetic Effectors in Maintenance of the Long-Term Persistent Bystander Effect in Spleen in Vivo," Carcinogenesis, 2007, pp. 1831-1838, vol. 28, No. 8.
Kozomara, A. et al., "miRBase: Integrating MicroRNA Annotation and Deep-Sequencing Data," Nucleic Acids Research, 2011, pp. D152-D157, vol. 39.
Krek, A. et al., "Combinatorial MicroRNA Target Predictions," Nature Genetics, May 2005, pp. 495-500, vol. 37, No. 5.
Kudo, et al., Prognostic staging system for hepatocellular carcinoma (CLIP score): its value and limitations, and a proposal for a new staging system, the Japan Integrated Staging Score (JIS score), J. Gastroenterol, 2003, vol. 38, 3, pp. 207-215.
Kulshreshtha, et al., A MicroRNA Signature of Hypoxia, Mol. Cell Biol., 2006, pp. 1395-1306.
Kulshreshtha, R. et al., "A MicroRNA Signature of Hypoxia," Molecular and Cellular Biology, Mar. 2007, pp. 1859-1867, vol. 27, No. 5.
Kuroki, et al., "Genetic Alterations of the Tumor Suppressor Gene WWOX in Esophageal Squamous Cell Carcinoma," Cancer Research, Apr. 2002, pp. 2258-2260, vol. 62.
Kutay, H. et al., "Downregulation of miR-122 in the Rodent and Human Hepatocellular Carcinomas," Journal of Cellular Biochemistry, 2006, pp. 671-678, vol. 99.
Lagos-Quintana, et al., Identification of Novel Genes Coding for Small Expressed RNA's, Science, 2001, vol. 294, 5543, pp. 853-858.
Lagos-Quintana, M. et al., "New MicroRNAs From Mouse to Human," RNA, 2003, pp. 175-179, vol. 9, No. 2.
Lagos-Quintana, M. et al., "Identification of Tissue-Specific MicroRNAs from Mouse," Current Biology, Apr. 2002, pp. 735-739, vol. 12.
Lall, et al., A Genome-Wide Map of Conserved MicroRNA Targets in *C. elegans*, Curr Biol 16, 2006, pp. 460-471.
Landgraf, P. et al., "A Mammalian MicroRNA Expression Atlas Based on Small RNA Library Sequencing," Cell, Jun. 2007, pp. 1401-1414, vol. 129.
Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.
Landthaler, et al., The Human DiGeorge Syndrome Critical Region Gene 8 and Its *D. melanogaster* Homolog are Required for miRNA Biogenesis, CB, 14, 2004, pp. 2162-2167.
Lanza, G. et al., "mRNA/microRNA Gene Expression Profile in Microsatellite Unstable Colorectal Cancer," Molecular Cancer, 2007, pp. 1-11, vol. 6, No. 54.
Lau, et al., An Abundant Class of Tiny RNA's With Probable Regulatory Roles in *Caenorhabditis elegans*, Science 2001, vol. 294, 5543, pp. 858-862.
Lawrie, C. H. "MicroRNAs and Haematology: Small Molecules, Big Function," British Journal of Haematology, Jun. 2007, pp. 503-512, vol. 137, No. 6.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Lawrie, C.H., "MicroRNA, Expression in Lymphoma," Expert Opinoin on Biological Therapy, Sep. 2007, pp. 1363-1374, vol. 7, No. 9.
Lecellier, et al., A Cellular MicroRNA mediates Antiviral, Science, 2005, vol. 308, pp. 557-560.
Lee, E. J. et al., "Expression Profiling Identifies MicroRNA Signature in Pancreatic Cancer," Int. J. Cancer, 2006, pp. 1046-1054, vol. 120.

(56) References Cited

OTHER PUBLICATIONS

Lee, et al., An Extensive Class of Small RNA's in *Caenorhabditis Elegans*, Science, 2001, vol. 294, 5543, pp. 862-864.
Lee, et al., MicroRNA maturation: stepwise processing and subcellular localization, EMBO, J., 2004, vol. 40, 3, pp. 667-676.
Lee, et al., MicroRNA maturation: stepwise processing and subcellular localization, EMBO, J. 2002, vol. 21, 17, pp. 4663-4670.
Lee, Y.S. et al., "MicroRNAs: Small but Potent Onogenes or Tumor Suppressors," Current Opinion in Investigational Drugs, Jun. 2006, pp. 560-564, vol. 7, No. 6.
Levy, et al., Staging of hepatocellular carcinoma: assessment of the Clip, Okuda, and Child-Pugh staging systems in a cohort of 257 patients in Toronto, Gut, 2002, vol. 50, 6, pp. 881-885.
Lewis, B. P. et al., "Prediction of Mammalian MicroRNA Targets," Cell, Dec. 2003, pp. 787-798, vol. 115.
Lewis, et al., Conserved Seed Pairing, Often Flanked by Adenosines, Indicates that Thousands of Human Genes are MicroRNA Targets, Cell, 2005, vol. 120, 1, pp. 15-20.
Li et al., miR-181a Is an Intrinsic Modulator of T Cell Sensitivity and Selection, Cell 2007, pp. 147-161.
Li, et al., DNA mismatch repair (MMR)-dependent 5-fluorouracil cytotoxicity and the potential for new therapeutic targets, British Journal of Pharmacology, 2008, vol. 158, pp. 679-692.
Li, et al., Expression of serum miR-221 in human heptocellular carcinoma and its prognostic significance, Biochemical Biophys Res Commun, 2011, Vol, 406, pp. 70-73.
Li, S.-C. et al., "Bioinformatic Discovery of MicroRNA Precursors from Human ESTs and Introns," BMC Genomics, 2006, vol. 7.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Lin, et al., Alteration of DNA methyltransferases contributes to 5 CpG methylation and poor prognosis in lung cancer, LungCancer, vol. 55, 2007, pp. 205-213.
Lin, R.-K. et al., "Alteration of DNA Methyltransferases Contributes to 5'CpG Methylation and Poor Prognosis in Lung Cancer," Lung Cancer, 2007, pp. 205-213, vol. 55.
Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.
Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.
Liu, et al., Characterization of in vitro and in vivo hypomethylating effects of decitabine in acute myeloid leukemia by a rapid, specific and sensitive LC-MS/MS method, Nucleic Acids, vol. 35, 2007, e31.
Liu, et al., Increased Expression of MicroRNA-221 in Gastric Cancer and Its Clinical Significance, Journal of International Medical Research, 2012, vol. 40, pp. 467-474.
Loffler, D. et al., "Interleukin-6-Dependent Survival of Multiple Myeloma Cells Involves the Stat3-Mediated Induction of MicroRNA-21 Through a Highly Conserved Enhancer," Blood, 2007, pp. 1330-1333, vol. 110, No. 4.
Lu, J. et al., "MicroRNA Expression Profiles Classify Human Cancers," Nature, Jun. 2005, pp. 834-838, vol. 435.
Lujambio, A. et al., "A MicroRNA DNA Methylation Signature for Human Cancer Metastasis," PNAS, Sep. 2008, pp. 13556-13561, vol. 105, No. 36.
Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.
Ma, X., et al., MicroRNAs in NF-kB signaling, Journal of Molecular Cell Biology, 2011, vol. 3, pp. 159-166.
Mack, G. S., "MicroRNA Gets Down to Business," Nature Biotechnology, Jun. 2007, pp. 631-638, vol. 25, No. 6.
Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.
Marcucci, et al., "MicroRNA Expression in Cytogenetically Normal Acute Myeloid Leukemia," NEJM, May 2008, pp. 1919-1928, vol. 358, No. 18.
Marsit, et al., MicroRNA Responses to Cellular Stress, Cancer Research, 2006, vol. 66, pp. 10843-10848.
Martin, M. et al., "MicroRNA-155 Regulates Human Angiotensin II Type 1 Receptor Expression in Fibroblasts," The Journal of Biological Chemistry, Jul. 2006, pp. 18277-18284, vol. 281, No. 27.
Mascellani, N. et al., "Using miRNA Expression Data for the Study of Human Cancer," Minerva Biotec, 2008, pp. 23-30, vol. 20.
Masri, A. et al., "MicroRNA Expression Analysis in Multiple Myeloma," Blood, Nov. 2005, p. 446A, vol. 106, No. 11, Abstract.
Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.
Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, Jul. 2007, pp. 21337-21348, vol. 282, No. 29.
McManus, M. T., "MicroRNAs and Cancer," Seminars in Cancer Biology, 2003, pp. 253-258, vol. 13.
Medina, et al., MicroRNA's 221 and 222 Bypass Quiescence and Compromise Cell Survival Cancer Research, 2008, vol. 68, pp. 2773-2780.
Medina, P.P. et al., "OncomiR Addiction in an in Vivo Model of MicroRNA-21-Induced Pre-B-Cell Lymphoma," Nature Letters, Sep. 2010, pp. 86-91, vol. 467.
Medina, P.P., "OncomiR Addicton in an in vivo Model of MicroRNA-21-Induced Pre-B-Cell Lymphoma," Supplementary Information, Sep. 2010, p. 1-22.
Megraw, M. et al., "miRGen: A Database for the Study of Animal MicroRNA Genomic Organization and Function," Nucleic Acids Research, 2007, pp. D149-D155, vol. 35.
Mendell, J.T., "miRiad Roles for the miR-17-92 Cluster in Development and Disease," Cell, 2008, pp. 217-.
Meng, F. et al., "MicroRNA-21 Regulates Expression of the PTEN Tumor Suppressor Gene in Human Hepatocellular Cancer," Gastroenterology, 2007, pp. 647-658, vol. 133.
Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mercatelli, et al., The Inhibition of the Highly Expressed Mir-221 and Mir-222 Impairs the Growth of Prostate Carcinoma Xenografts in Mice, Plos One, 2008, vol. 3, No. 12, pp. 21337-21348.
Metzler, et al., High Expression of Precursor MicroRNA-155/BIC RNA in Children with Burkitt Lymphoma, Genes, Chromosomes, Cancer, 2004, vol. 39, 2, pp. 167-169.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.
Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mizusawa, et al., Differentiation phenotypes of pancreatic islet h- and a-cells are closely related with homeotic genes and a group of differentially expressed genes, Gene 2004, vol. 331, pp. 53, 63.

(56) References Cited

OTHER PUBLICATIONS

Mountzios, G. et al., "Mechanisms of Disease: Signal Transduction in Lung Carcinogenesis-A Comparison of Smokers and Never-Smokers," Nature Clinical Practice Oncology, Oct. 2008, pp. 610-618, vol. 5, No. 10.

Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.

Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.

Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.

Nakamura, et al., ALL-1 Is a Histone Methyltransferase that Assembles a Supercomplex of Proteins Involved in Transcriptional Regulation, Mol. Cell, 10, 2002, pp. 1119-1128.

Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.

Nam, E.J. et al., "MicroRNA Expression Profiles in Serous Ovarian Carcinoma," Clinical Cancer Research, 2008, pp. 2690-2695, vol. 14, No. 9.

Nana-Sinkam, et al., Clinical applications for microRNA's in cancer, Nature, 2013, vol. 93.

Negrini, M. et al., "MicroRNAs in Human Cancer: From Research to Therapy," Journal of Cell Science, Apr. 2007, pp. 1833-1840, vol. 120.

Nicoloso, M.S. et al., "MicroRNAs- The Micro Steering Wheel of Tumour Metastases," Nature Reviews: Cancer, Apr. 2009, pp. 293-302, vol. 9.

Nippon-Journal of the Japanese Society, 1993, vol. 82, pp. 1053-1057.

Nurden, A.T., "Qualitative Disorders of Platelets and Megakaryocytes," Journal of Thrombosis and Haemostasis, 2005, vol. 3, pp. 1773-1782.

O'Connell, R. et al., "Inositol Phosphatase SHIP1 is a Primary Target of miR-155," PNAS, Apr. 2009, pp. 7113-7118, vol. 106, No. 17.

O'Donnell, c-Myc-regulated microRNAs modulate E2F1 expression, Nature, 2005, pp. 839-843.

Okada, H. et al., "MicroRNAs in Immune Regulation—Opportunities for Cancer Immunotherapy," The International Journal of Biochemistry & Cell Biology, 2010, pp. 1256-1261, vol. 42.

Okuda, et al., Natural History of Hepatocellular Carcinoma and Prognosis in Relation to Treatment, Cancer, 1985, vol. 56, 4, pp. 918-928.

Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.

Palamarchuk, A. et al., "AKT Phosphorylates Tc11 Oncoprotein and Inhibits Its Repressor Activity," Cancer Research, Jun. 2005, pp. 4515-4519, vol. 65, No. 11.

Pallante, et al., MicroRNA deregulation in human thyroid papillary carcinomas, Endocr. Relat. Cancer, 2006, vol. 13, 2, pp. 497-508.

Pan, M. R. et al. Non-Steroidal Anti-Inflammatory Drugs Suppress the ERK, Cellular Signaling, 20, 2008, pp. 1134-1141.

Panarelli, et al., MicroRNA Expression Aids the Preoperative Diagnosis of Pancreatic Ductal Adenocarcinoma, Pancreas, 2012, vol. 41, pp. 685-690.

Papageorgiou, et al., Interferon-a Induces TRAIL Expression and Cell Death Via an IRF-1-Dependent Mechanism in Human Bladder Cancer Cells, Cancer Biol Ther, 2007, vol. 6, No. 6, pp. 872-879.

Park, et al., Antisense inhibition of microRNA-21 or-221 arrests cell cycle, induces apoptosis, and sensitizes the effects of gemcitabine in pancreatic adenocarcinoma, Pancreas, 2009, Abstract.

Park, J.-K. et al., "miR-221 Silencing Blocks Hepatocellular Carcinoma and Promotes Survival," Cancer Research, Dec. 2011, pp. 7608-7616, vol. 71, No. 24.

Parkin, et al., Global Cancer Statistics, 2002, CA, Cancer, J. Clin., 2005, vol. 55, 2, pp. 74-108.

Partha, D. et al., "Early Detection of Ovarian Cancer," NIH Public Access Author Manuscript, Jun. 2008, pp. 117, Retrieved from the Internet.

Pasquinelli, et al., MicroRNAs: a developing story, Current Opinion in Genetics and Development, vol. 15, 2005, pp. 200-205.

Pathi, S. S., et al., GT-094, a No-NSAID, Inhibits Colon, Molecular Cancer Research, 2011, vol. 9, pp. 195-202.

Pawelczyk, T. et al., "Expression in *Escherichia Coli* and Simple Purification of Human Fhit Protein," Protein Expr. Purlf., Apr. 2000, pp. 320-326, vol. 18, No. 3.

Pedersen, I. M. et al., "Interferon Modulation of Cellular MicroRNAs as an Antiviral Mechanism," Nature, Oct. 2007, pp. 919-922, vol. 449.

Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.

Pekarsky, Y. et al., "Animal Models for Chronic Lymphocytic Leumekia," Journal of Cellular Biochemistry, 2007, pp. 1109-1118, vol. 100.

Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.

Pekarsky, Y. et al., "Tcl1 Enhances Akt Kinase Activity and Mediates Its Nuclear Translocation," PNAS, Mar. 2000, pp. 3028-3033, vol. 97, No. 7.

Petrocca, F. et al., "MicroRNAs Deregulation in Gastric Cancer," PNAS, Apr. 2006, p. 1338, vol. 47, Abstract # 5690.

Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.

Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.

Pichiorri, F. et al., "MicroRNAs Regulate Critical Genes Associated with Multiple Myeloma Pathogenesis," PNAS, Sep. 2008, pp. 12885-12890, vol. 105, No. 35.

Pichiorri, F. et al., "MicroRNA Signatures in Multiple Myeloma," 99th AACR Annual Meeting, Apr. 12-16, 2008, pp. 1203, vol. 49, Abstract.

Pineau, P. et al., "miR-221 Overexpression Contributes to Liver Tumorigenesis," PNAS, Jan. 2010, pp. 264-269, vol. 107, No. 1.

Poliseno, et al., MicroRNAs modulate the angiogenic properties of HUVECs, Blood, 2006.

Porkka, K.P. et al., "MicroRNA Expression Profiling in Prostate Cancer," Cancer Research, 2007, pp. 6130-6135, vol. 67, No. 13.

Pouponnot, C. et al., "Cell Context Reveals a Dual Role for Maf in Oncogenesis," Oncogene, 2006, pp. 1299-1310, vol. 25.

Poy, et al., A pancreatic islet-specific microRNA regulates insulin secretion, Nature, 2004, vol. 432, pp. 226-230.

Prueitt, R. L. et al., "Expression of MicroRNAs and Protein-Coding Genes Associated with Perineural Invasion in Prostate Cancer," The Prostate, 2008, pp. 1152-1164, vol. 68.

Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.

Pu, et al., Circulating miR-221 directly amplified from plasma is a potential diagnostic and prognostic marker of colorectal cancer and is correlated with p53 expression, J. Gastroenterol Hepatol, 2010, vol. 25, pp. 1674-1680.

Qin, H. R. et al., "A Role for the WWOX Gene in Prostate Cancer," Cancer Research, Jul. 2006, pp. 6477-6481, vol. 66, No. 13.

Ramkissoon, S. H, et al., "Hematopoietic-Specific MicroRNA Expression in Human Cells," Leukemia Research, 2006, pp. 643-647, vol. 30.

Ren, et al., Co-delivery of as-miR-21 and 5-FU by Poly (amidoamine) Dendrimer Attenuates Human Glioma Cell Growth in Vitro, Journal of Biomedical Science, 2010, vol. 21, pp. 303-314.

(56) References Cited

OTHER PUBLICATIONS

Resnick, et al., The detection of differentially expressed microRNAs from the serum of ovarian cancer patients using a novel real-time PCR platform, Science Direct, 2009, vol. 112, pp. 55-59.
Ribas, J. et al., "The Transcriptional Regulation of miR-21, Its Multiple Transcripts, and Their Implication in Prostate Cancer," Cell Cycle, 2010, pp. 923-929, vol. 9.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.
Ryu, J.K. et al., "Aberrant MicroRNA-155 Expression is an Early Event in the Multistep Progression of Pancreatic Adenocarcinoma," Pancreatology, 2010, pp. 66-73, vol. 10.
Sah., et al, Translation Inhibitors Sensitize Prostate Cancer Cells to Apoptosis Induced by Tumor Necrosis Factor-related Apoptosis-inducing Ligand (Trail) by Activating c-Jun N-terminal Kinase, J. Biol Chem 2003, vol. 278, pp. 20593-20602.
Saini, H. K. et al., "Annotation of Mammalian Primary MicroRNAs," BMC Genomics, 2008, vol. 9.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Santanam, U. et al., "Chronic Lymphocytic Leukemia Modeled in Mouse by Targeted miR-29 Expression," PNAS, Jul. 2010, pp. 12210-12215, vol. 107, No. 27.
Sasaki, Y.T.F. et al., "Coordinated Expression of ncRNAs and HOX mRNAs in the Human HOXA Locus," Biochemical and Biophysical Communications, 2007, pp. 724-730, vol. 357.
Schagen, F. et al., "Genetic Targeting of Adenovirus Vectors Using a Reovirus Sigma1-Based Attachment Protein," Molecular Therapy, May 2006, pp. 997-1005, vol. 13, No. 5.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.
Schetter, et al., MicroRNA Expression Profiles Associated With Prognosis and Therapeutic Outcome in Colon Adenocarcinoma, Journal of America Medical Association, 2008, vol. 299, pp. 426-436.
Schmittgen, T. D. et al., "A High-Throughput Method to Monitor the Expression of MicroRNA Precursors," Nucleic Acids Research, Feb. 2004, vol. 32, No. 4.
Schrump, et al.,Targeting the Epigenome for the Treatment and Prevention of Lung Cancer Semin Oncol, 32, 2005, pp. 488-502.
Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.
Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.
Selvendiran, K. et al. NCX-4016 a Nitro-derivative of Aspirin, Cell Cycle, 2008, 7:1, pp. 81-88.
Seth, P., "Vector-Mediated Cancer Gene Therapy," Cancer Biology & Therapy, May 2005, pp. 512-517, vol. 4, Issue 5.
Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.
Sharma, S. et al., "Development of Inhalational Agents for Oncologic Use," Journal of Clinical Oncology, Mar. 2001, Abstract, vol. 19, Issue 6.
Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.
Shih, K.K. et al., "Exosomal MicroRNAs Step into the Biomarker Arena," Gynecologic Oncology, Jul. 2008, pp. 1-2, vol. 110, No. 1.
Slaby, et al., AlteredExpressionofmiR21-miR31, Oncology, 2007, vol. 72, pp. 1-6.
Slack, F.J., "Big Roles for Small RNAs," Nature, Feb. 2010, p. 616, vol. 463.
Sonoki, T. et al., "Insertion of MicroRNA-125b-1, A Human Homologue of lin-4, into a Rearranged Immunoglobulin Heavy Chain Gene Locus in a Patient with Precursor B-Cell Acute Lymphoblastic Leukemia," Leukemia, 2005, pp. 1-2, vol. 19.
Stamatopoulos, B. et al., "MicroRNA-29c and MicroRNA-233 Down-Regulation has in Vivo Significance in Chronic Lymphocytic Leukemia and Improves Disease Risk Stratification," Blood, May 2009, pp. 5237-5245, vol. 113, No. 21.
Stenvang, et al., The utility of LNA in microRNA-based cancer diagnostics and therapeutics, Cancer Biology, 2008, pp. 89-102.
Suarez-Saiz, F.J. et al., "MicroRNA Expression Profiling in Acute Myelogenous Leukemia," Canada Blood, Nov. 2004, Abstract #1131, p. 320A.
Sugito, et al., Rnasen regulates Cell Proliferation and Affects Survival in Esophageal Cancer Patients, Clin Canc Res, 2006[1], vol. 12, pp. 7322-7328.
Suh, et al., Human embryonic stem cells express a unique set of microRNAs, Dev. Biol., 270, 2004, pp. 488-498.
Sun Kai, Analysis of microRNA expression patterns, Chinese Journal of Experimental Surgery, 2006, vol. 23, No. 8, pp. 945-947.
Sun, et al., MicroRNA-221 inhibits CDKN1C/p57 expression in human colorectal carcinoma, Acta Pharmacologica Sinica, 2011, vol. 32, pp. 375-384.
Suzuki, et al., RNA Interference-Mediated Knockdown of DNA Methyltransferase 1 Leads to Promoter Demethylation and Gene Re-Expression in Human Lung and Breast Cancer CellsCancer, Research, 64, 2004, pp. 3137-3143.
Taccioli, C. et al., "Ucbase & miRfunc: A Database of Ultraconserved Sequences and MicroRNA Function," Nucleic Acids Research, 2009, pp. D41-D48, vol. 37.
Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.
Tam, The Emergent Role of MicroRNA's in Molecular Diagnostics of Cancer, Journal of Molecular Diagnostics, 2008, vol. 10, pp. 411-414.
Tang, X. et al., "A Simple Array Platform for MicroRNA Analysis and Its Application in Mouse Tissues," RNA, Aug. 2007, pp. 1-20, vol. 13.
Tenzer, Molecular Evolution of a MicroRNA Cluster, J. Mol. Biol, 2004, vol. 339, 2, pp. 327-335.
Tatsuya, et al., Oncogenic All1 fusion proteins target Drosha-mediated microRNA processing, PNAS, 2007, vol. 104, pp. 10980-10985.
Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Teachey, et al., Mammalian target of rapamycin inhibitors and their potential role in therapy in leukemia and other haematogical malignancies, BJH, 2009[1], vol. 145, pp. 569-580.
Thomson, et al., Extensive post-transcriptional regulation of microRNAs and its implications for cancer Genes, Dev. 20, 2006, pp. 2202-2207.
Thomson, J. M. et al., "A Custom Microarray Platform for Analysis of MicroRNA Gene Expression," Nature Methods, Oct. 2004, pp. 1-7, vol. 1, No. 1.
Thomson, M., Supplementary data for "A Custon Microarray Platform for Analysis of MicroRNA Gene Expression," Nature Methods, Oct. 2004, pp. 47-53, vol. 1, No. 1.
Thorgeirsson, et al., Molecular pathogenesis of human hepatocellular carcinoma, Nat, Genet. 2002, vol. 31, 4, pp. 339-346.

(56) References Cited

OTHER PUBLICATIONS

Thorgeirsson, S. S. et al., "Functional Genomics of Hepatocellular Carcinoma," Hepatology, Feb. 2006, pp. S145-S150, vol. 43, No. 2, Suppl. 1.

Tibshirani, et al., Diagnosis of multiple cancer types by shrunken centroids of gene expression, Proc. Natl. Acad. Sci., 2002, vol. 99, 10, pp. 6567-6572.

Tili, E. et al., "Expression and Function of Micro RNAs in Immune Cells During Normal or Disease State," International Journal of Medicine Sciences, 2008, pp. 73-79, vol. 5, No. 2.

Tkachuk, et al., Involvement of a Homolog of *Drosophila trithorax* by 11 q23 Chromosomal Translocations in Acute Leukemias Cell, vol. 71, 1992, pp. 691-700.

Tockman, M. S. et al., "Considerations in Bringing a Cancer Biomarker to Clinical Application," Cancer Research, May 1992, pp. 2711s-2718s, vol. 52.

Tokarz, et al., The Role of microRNA in metastatic colorectal cancer and its significance in cancer prognosis and treatment, ACTA, 2012, vol. 59, pp. 467-474.

Trapasso, F. et al., "FHIT Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.

Tricoli, J. V. et al., "MicroRNA: Potential for Cancer Detection, Diagnosis, and Prognosis," Cancer Research, May 2007, pp. 4553-4555, vol. 67, No. 10.

Tsunoda, et al., Oncogenic KRAS regulates miR-200c and miR-221, 222 in a 3D-specific manner in colorectal cancer cells, Anticancer Research, 2011, Abstract.

Tusher, et al., Significance analysis of microarrays applied to the ionizing radiation response, Proc. Natl. Acad. Sci., 2001, vol. 98, 9, pp. 5116-5121.

Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.

Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.

Ulivi, et al., p16INK4A and CDH13 Hypermethylation in Tumor and Serum of Non-Small Cell Lung Cancer Patients Journal of Cell, Physiol, 206, 2006, pp. 611-615.

Valeri, et al., MicroRNA-21 induces resistance to 5-fluorouracil by down-regulating human DNA MutS homolog 2 hMSH2 ,PNAS, 2010, vol. 107, pp. 21098-21103.

Valeri, N. et al., "Epigenetics, miRNAs, and Human Cancer: A New Chapter in Human Gene Regulation," Mamm Genome, Aug. 2009, pp. 573-580, vol. 20.

Valeri, N. et al., "Modulation of Mismatch Repair and Genomic Stability by miR-155," PNAS, Apr. 2010, pp. 6982-6987, vol. 107, No. 15.

VanDenEynde, et al., Is Tailored Adjuvant Treatment for Colon Cancer Possible, Clinical Colorectal Cancer, 2010, vol. 9, pp. 15-21.

Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.

Varotti, et al., Comparison between the fifth and sixth editions of the AJCC/UICC TNM staging systems for hepatocellular carcinoma: multicentric study on 393 cirrhotic resected patients, Eur. J. Surg. Oncol, 2005, vol. 31, 7, pp. 760-767.

Vassilev et al., "In Vivo Activation of the p53 Pathway by Small-Molecule Antagonists of MDM2," Science, 2004, pp. 844-848, vol. 303.

Vatolin, et al., A Novel Method to Detect Functional MicroRNA Targets, J. Mol. Biol., 358, 2006, pp. 983-996.

Verschuur, A.C., "Acute Megakaryoblastic Leukemia," May 2004, pp. 1-5, Retrieved from the Internet: URL: http://www.orpga.net/data/patho/GB/uk-AMLM7.pdf.

Virgilio, L. et al., "Identification of the TCL1 Gene Involved in T-Call Malignancies," Proc. Natl. Acad. Sci., Dec. 1994, pp. 12530-12534, vol. 91.

Visone, R. et al., "MiRNAs and Cancer," The American Journal of Pathology, Apr. 2009, pp. 1131-1138, vol. 174, No. 4.

Volinia, et al., "Reprogramming of MirRNA Networks in Cancer and Leukemia," Genome Research, 2010, pp. 589-599, vol. 20.

Volinia, et al., Breast cancer signatures for invasiveness and prognosis defined by deep sequencing of microRNA, PNAS, Feb. 21, 2012, vol. 109, No., pp. 3024-3029.

Volinia, Prognostic microRNA/mRNA signature from the integrated analysis of patients with invasive breast cancer, PNAS, pp. 1-5, 2013.

Volinia, S. et al., "A MicroRNA Expression Signature of Human Solid Tumors Defines Cancer Gene Targets," PNAS, Feb. 2006, pp. 2257-2261, vol. 103, No. 7.

Wang, E. et al., "Ontogeny and Oncogenesis Balance the Transcriptional Profile of Renal Cell Cancer," Cancer Research, Oct. 2004, pp. 7279-7287, vol. 64.

Wang, X. et al., "Association Between CpG Island Methylation of the WWOX Gene and Its Expression in Breast Cancers," Tumor Biology, Feb. 2009, pp. 8-14, vol. 30.

Watson, D.I. et al., "MicroRNA Expression Profiles in Barrett's Oesophagus," RACS Annual Scientific Congress, 2007, pp. A45, vol. 77.

Weidhaas, J., "Using MicroRNAs to Understand Cancer Biology," Published Online Dec. 21, 2009, DOI:10.1016/S1470-2045(09)70386-9.

Wiemer et al., "The Role of MicroRNAs in Cancer: No Small Matter," European Journal of Cancer, Jun. 12, 2007, vol. 43, No. 10, pp. 1529-1544.

Wijermans, P.W., "Low Dose Azanucleosidesfor High Risk (s) MDS and AML," Haematologica Reports,Nov. 2006, pp. 74-76. vol. 2, Issue, 15.

Wildi, et al., Critical evaluation of the different staging systems for hepatocellular carcinoma, Br. J. Surg., 2004, vol. 91, 4, pp. 400-408.

Williams, C.S., "OncomiRs: The Discovery and Progress of MicroRNAs in Cancers," Molecular Cancer, Sep. 2007, pp. 259-269, vol. 6, No. 4.

Wu, D. et al., "Micro-RNA: A New Kind of Gene Regulators," Agricultural Sciences in China, Jan. 2006, pp. 77-80, vol. 5, No. 1.

Xi, Y. et al., "Prognostic Values of MicroRNAs in Colorectal Cancer," Biomarker Insights, Jan. 2006, pp. 113-121, vol. 1.

Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.

Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.

Yanaihara, N. et al., "Unique MicroRNA Molecular Profiles in Lung Cancer Diagnosis and Prognosis," Cancer Cell, Mar. 2006, pp. 189-198, vol. 9.

Yang, J. et al., "Analysis of Sequence Variations in 59 MicroRNAs in Hepatocellular Carcinomas," Mutation Research, Aug. 2008, pp. 205-209, vol. 638.

Ye, et al., Predicting hepatitis B virus-positive metastatic hepatocellular carcinomas using gene expression profiling and supervised machine learning, Nat. Med., 2003, vol. 9, 4, pp. 416-423.

Yekta, et al., MicroRNA-Directed Cleavage of HOXB8 MRNA, Science, 2004, vol. 304, pp. 594-596.

Yendamuri, S. et al., "WW Domain Containing Oxidoreductase Gene Expression is Altered in Non-Small Cell Lung Cancer," Cancer Research, Feb. 2003, pp. 878-881, vol. 63.

Yi, et al., Exportin-5 mediates the nuclear export of pre-microRNAs and short hairpin RNAs, Genes Dev, 2003, vol. 17, 24, pp. 3011-3016.

Yoo, et al., Epigenetic therapy of cancer: past, present and future, Nature Reviews Drug Discov 5, 2006, pp. 37-50.

Yoon, S. et al., "Prediction of Regulatory Modules Comprising MicroRNAs and Target Genes," Bioinformatics Genes and Genomes, 2005. Pages ii93-ii100, vol. 21, Suppl. 2.

Yu, et al., Human microRNA clusters: Genomic organization and expression profile in leukemia cell lines, Biomed Biophys Res Comm, 2006, pp. 59-68.

(56) References Cited

OTHER PUBLICATIONS

Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.

Yuki, et al., Growth and Spread of Hepatocellular Carcinoma, Cancer, 1990, vol. 66, 10, pp. 2174-2179.

Zaman, et al., Current status and implications of microRNAs in ovarian cancer diagnosis and therapy, J Ovarian Res, 2012[1].

Zawacka-Pankau, J. et al., "Expression and Simple, One-Step Purification of Fragile Histidine Triad (Fhit) Tumor Suppressor Mutant Forms in *Escherichia Coli* and their Interaction with Protoporphyrin IX," Biotechnology Letters, Jun. 2007, pp. 877-883, vol. 29, No. 6.

Zeng, Y. et al., "Recognition and Cleavage of Primary MicroRNA Precursors by the Nuclear Processing Enzyme Drosha," The EMBO Journal, 2005, pp. 138-148, vol. 24.

Zhang, L. et al., "Genomic and Epigenetic Alterations Deregulate MicroRNA Expression in Human Epithelial Ovarian Cancer," PNAS, May 2008, pp. 7004-7009, vol. 105, No. 19.

Zhang, L. et al., "MicroRNAs Exhibit High Frequency Genomic Alterations in Human Cancer," PNAS, Jun. 2006, pp. 9136-9141, vol. 103, No. 24.

Zhang, L. et al., Supporting Information, PNAS 2008, pp. 1-11.

Zhang, Z. et al., "Three Biomarkers Identified from Serum Proteomic Analysis for the Detection of Early Stage Ovarian Cancer," Cancer Research, Aug. 2004, pp. 5882-5890, vol. 64.

Zhao et al., "p53 Mediates the Negative Regulation of MDM2 by Orphan Receptor TR3," The EMBO Journal, 2006, pp. 5703-5715, vol. 25.

Zhou, et al., Binding of NF-kappaB p65 subunit to the promoter elements is involved in LPS-induced transactivation of miRNA genes in human biliary epithelial cells, Nucleic Acids Research, 2010, vol. 38, No. 10, pp. 3222-3232.

Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

Table 1. The expression levels of 66 differentially expressed miRNAs in the comparison of ductal carcinoma *in-situ* (DCIS) to normal breast (false detection rate <0.05).

| Parametric p-value | DCIS | Normal breast | Fold-change | miRNA |
|---|---|---|---|---|
| 7.00E-07 | 796.9 | 212.3 | 3.75 | miR-361-5p |
| 1.00E-06 | 6058.5 | 44926.0 | 0.13 | let-7b |
| 2.20E-06 | 374988.8 | 17951.4 | 20.89 | miR-21 |
| 8.90E-06 | 395.6 | 3139.2 | 0.13 | miR-127-3p |
| 1.13E-05 | 1298.6 | 215.5 | 6.03 | miR-374a |
| 1.33E-05 | 2491.0 | 9702.5 | 0.26 | let-7c |
| 1.33E-05 | 2551.2 | 25270.4 | 0.1 | miR-320-RNASEN |
| 2.30E-05 | 1078.4 | 213.0 | 5.06 | miR-96 |
| 2.36E-05 | 262.9 | 929.4 | 0.28 | miR-652 |
| 4.55E-05 | 1853.6 | 17393.9 | 0.11 | miR-378 |
| 4.93E-05 | 711.4 | 7091.5 | 0.1 | miR-143* |
| 5.41E-05 | 1069.3 | 210.7 | 5.08 | miR-183 |
| 5.80E-05 | 1062.5 | 256.5 | 4.14 | miR-374b |
| 7.97E-05 | 8462.9 | 47032.5 | 0.18 | miR-99a |
| 2.13E-04 | 4066.5 | 496.3 | 8.19 | miR-16(2) |
| 2.79E-04 | 2464.4 | 10262.0 | 0.24 | miR-497 |
| 3.18E-04 | 5167.7 | 778.2 | 6.64 | miR-142-5p |
| 3.19E-04 | 275.0 | 1976.8 | 0.14 | miR-376a-3p(2) |
| 3.46E-04 | 9103.5 | 44155.3 | 0.21 | miR-145 |
| 3.71E-04 | 263.9 | 915.7 | 0.29 | miR-574-3p |
| 4.08E-04 | 740.5 | 217.9 | 3.4 | miR-429 |
| 4.41E-04 | 534.7 | 3395.5 | 0.16 | miR-193b |
| 4.96E-04 | 1526.2 | 4690.4 | 0.33 | miR-221 |
| 5.08E-04 | 2212.1 | 4853.6 | 0.46 | miR-140-3p |
| 6.21E-04 | 1899.4 | 402.6 | 4.72 | miR-182 |
| 9.05E-04 | 803.1 | 282.6 | 2.84 | miR-15b |
| 9.07E-04 | 3162.6 | 10838.6 | 0.29 | miR-100 |
| 9.87E-04 | 19346.0 | 95703.7 | 0.2 | miR-22 |
| 1.03E-03 | 5433.8 | 1083.2 | 5.02 | miR-106b |
| 1.04E-03 | 238.1 | 376.9 | 0.63 | miR-324 |
| 1.07E-03 | 7999.4 | 953.2 | 8.39 | miR-200c |
| 1.18E-03 | 951.8 | 347.0 | 2.74 | miR-107 |
| 1.29E-03 | 1154.7 | 3821.3 | 0.3 | miR-423-3p |
| 1.38E-03 | 1822.6 | 3873.3 | 0.47 | let-7d |
| 1.42E-03 | 359.5 | 923.5 | 0.39 | miR-145* |
| 0.002 | 200.0 | 277.3 | 0.72 | miR-106b* |

Figure 9

| | | | | |
|---|---|---|---|---|
| 0.002 | 436.6 | 200.0 | 2.18 | miR-32 |
| 0.002 | 350.4 | 2022.6 | 0.17 | miR-193a-5p |
| 0.002 | 443.9 | 2069.9 | 0.21 | miR-423-5p |
| 0.002 | 8220.0 | 1480.0 | 5.55 | miR-26b |
| 0.003 | 700.9 | 262.7 | 2.67 | miR-223 |
| 0.003 | 6672.7 | 3303.4 | 2.02 | miR-30d |
| 0.004 | 386.5 | 200.0 | 1.93 | miR-128(2) |
| 0.004 | 544.8 | 1004.9 | 0.54 | miR-28-3p |
| 0.004 | 4730.0 | 1026.4 | 4.61 | miR-200b |
| 0.004 | 14046.7 | 64371.0 | 0.22 | miR-125b(2) |
| 0.005 | 1174.7 | 482.7 | 2.43 | miR-342 |
| 0.005 | 524.7 | 200.0 | 2.62 | miR-340 |
| 0.005 | 616.4 | 3779.8 | 0.16 | miR-376c |
| 0.005 | 404.0 | 200.0 | 2.02 | miR-155 |
| 0.005 | 3332.1 | 900.0 | 3.7 | miR-142-3p |
| 0.005 | 437.1 | 1482.1 | 0.29 | miR-185 |
| 0.005 | 335.6 | 1086.0 | 0.31 | miR-452 |
| 0.006 | 3183.7 | 9552.2 | 0.33 | miR-125a |
| 0.006 | 4242.1 | 1227.3 | 3.46 | miR-29c |
| 0.007 | 1009.5 | 317.6 | 3.18 | miR-20a |
| 0.007 | 8180.2 | 1595.1 | 5.13 | miR-29b(2) |
| 0.008 | 1812.3 | 535.8 | 3.38 | miR-19a |
| 0.009 | 249.4 | 662.4 | 0.38 | miR-210 |
| 0.010 | 5224.3 | 15967.8 | 0.33 | miR-451-DICER1 |
| 0.011 | 1483.4 | 700.5 | 2.12 | miR-92a(2) |
| 0.012 | 1651.6 | 834.4 | 1.98 | miR-425 |
| 0.013 | 1271.6 | 480.1 | 2.65 | miR-15a |
| 0.013 | 23718.5 | 9885.1 | 2.4 | miR-26a(2) |
| 0.015 | 234.6 | 439.8 | 0.53 | miR-17* |
| 0.015 | 7149.8 | 15222.5 | 0.47 | miR-19b(2) |

Figure 9 Cont.

| Table 2. The 6 miRNAs differentially expressed in IDC vs. DCIS. Only HER2+/ER- samples were considered in this comparison (false detection rate <0.05). | | | | |
|---|---|---|---|---|
| Parametric p-value | IDC (HER2+/ER-) | DCIS (HER2+/ER-) | Fold-change | miRNA |
| 1e-07 | 1627.8 | 4307.6 | 0.38 | miR-10b |
| 3.3e-06 | 248.3 | 639.3 | 0.39 | miR-335-5p |
| 3.8e-06 | 4900.6 | 1822.5 | 2.69 | let-7d |
| 0.0001 | 18038.8 | 41554.8 | 0.43 | miR-143 |
| 0.0006 | 1041.1 | 249.3 | 4.18 | miR-210 |
| 0.0009 | 3024.0 | 1526.1 | 1.98 | miR-221 |

Figure 10

| Table 3. The 9 miRNAs differentially expressed in invasive ductal carcinoma (IDC), when compared to ductal carcinoma in-situ (DCIS). All available IDC samples were included in the analysis, regardless of the subtype (false detection rate <0.05). | | | | |
|---|---|---|---|---|
| Parametric p-value | IDC (all) | DCIS (HER2+/ER-) | Fold-change | miRNA |
| 4e-07 | 1782.9 | 4307.6 | 0.41 | miR-10b |
| 5e-07 | 16213.2 | 41554.8 | 0.39 | miR-143 |
| 5.2e-06 | 4601.1 | 1822.5 | 2.52 | let-7d |
| 1.59e-05 | 222.9 | 360.3 | 0.62 | miR-218(2) |
| 5.43e-05 | 282.2 | 639.3 | 0.44 | miR-335-5p |
| 7.13e-05 | 5898.2 | 12809.3 | 0.46 | miR-126 |
| 0.0004 | 2978.2 | 1526.1 | 1.95 | miR-221 |
| 0.0004 | 5669.2 | 1954.3 | 2.9 | miR-181a(2) |
| 0.0010 | 838.2 | 249.3 | 3.36 | miR-210 |

Figure 11

| Table 4. The 10 miRNAs differentially expressed in ER+ IDC when compared to ER- IDC (false detection rate <0.05). ||||| 
|---|---|---|---|---|
| Parametric p-value | ER+/HER2- (IDC) | HER2+/ER- or TNBC (IDC) | Fold-change | miRNA |
| 2.10e-06 | 443 | 225.9 | 1.96 | miR-190b |
| 1.41e-05 | 24024.5 | 15080 | 1.59 | miR-103(2) |
| 2.04e-04 | 10216.8 | 19352.2 | 0.53 | miR-24(2) |
| 2.15e-04 | 803.3 | 1952.8 | 0.41 | miR-146a |
| 4.28e-04 | 3339.6 | 1966 | 1.7 | miR-497 |
| 4.61e-04 | 6626 | 10622.8 | 0.62 | let-7i |
| 0.001 | 6362 | 2559.6 | 2.49 | miR-451-DICER1 |
| 0.001 | 239.6 | 752.3 | 0.32 | miR-224 |
| 0.002 | 5326 | 3077.9 | 1.73 | miR-320-RNASEN |
| 0.002 | 208.2 | 303.2 | 0.69 | miR-197 |

Figure 12

| Table 5. miR-342 is the only miRNA differentially expressed in HER2+/ER- IDC when compared to all other IDC (false detection rate <0.05). |||||
|---|---|---|---|---|
| Parametric p-value | HER2+/ER- positive | HER2- negative | Fold-change | miRNA |
| 0.001 | 858.1 | 1467.1 | 0.58 | miR-342 |

Figure 13

| Table 6. The miRNAs differentially expressed in ER+/HER2+ IDC were all down regulated when compared to the other IDC subtypes (false detection rate <0.05). |||||
|---|---|---|---|---|
| Parametric p-value | ER+/HER2+ IDC | All other IDC | Fold-change | miRNA |
| 1.56e-05 | 480.8 | 1102.4 | 0.44 | miR-96 |
| 3.94e-05 | 8970.5 | 17242.2 | 0.52 | miR-148a |
| 2.70e-04 | 818.8 | 1674.1 | 0.49 | miR-182 |
| 2.78e-04 | 680.7 | 1281.0 | 0.53 | miR-183 |
| 0.002 | 2732.1 | 4478.4 | 0.61 | miR-106b |
| 0.002 | 3984.4 | 6738.4 | 0.59 | miR-200c |

Figure 14

| Table 7. The miRNAs differentially expressed in TNBC IDC when compared to the other IDC subtypes (false detection rate <0.05). | | | | |
|---|---|---|---|---|
| Parametric p-value | TNBC (IDC) | All other IDC | Fold-change | miRNA |
| 1.00E-07 | 3703.2 | 1017.4 | 3.64 | miR-92a(2) |
| 3.00E-07 | 538.9 | 267.1 | 2.02 | miR-128(2) |
| 9.00E-07 | 899.1 | 313.1 | 2.87 | miR-18a |
| 1.80E-06 | 3311.6 | 7755.4 | 0.43 | miR-145 |
| 9.20E-06 | 327.0 | 810.4 | 0.4 | miR-143* |
| 4.13E-05 | 484.0 | 1285.9 | 0.38 | miR-199b-5p |
| 4.24E-05 | 319.8 | 639.3 | 0.5 | miR-331 |
| 4.73E-05 | 11912.3 | 5160.9 | 2.31 | miR-200c |
| 9.19E-05 | 1518.3 | 662.1 | 2.29 | miR-15b |
| 9.37E-05 | 583.9 | 303.7 | 1.92 | miR-484-RNASEN |
| 1.24E-04 | 3584.7 | 7383.0 | 0.49 | miR-199b-3p |
| 1.24E-04 | 7198.5 | 14819.4 | 0.49 | miR-199a-3p(2) |
| 1.55E-04 | 4060.3 | 8930.8 | 0.45 | miR-199a-5p(2) |
| 1.60E-04 | 2621.7 | 955.9 | 2.74 | miR-20a |
| 1.64E-04 | 431.6 | 235.5 | 1.83 | miR-455-3p |
| 2.35E-04 | 1577.1 | 3320.4 | 0.47 | miR-424 |
| 2.60E-04 | 1788.1 | 797.1 | 2.24 | miR-151-5p |
| 5.40E-04 | 4993.9 | 2368.4 | 2.11 | miR-17 |
| 8.26E-04 | 495.6 | 257.9 | 1.92 | miR-9(3) |
| 0.002 | 17664.8 | 32167.9 | 0.55 | miR-22 |
| 0.002 | 578.2 | 1366.7 | 0.42 | miR-126* |
| 0.002 | 819.7 | 451.8 | 1.81 | miR-361-5p |
| 0.003 | 7400.1 | 3561.4 | 2.08 | miR-16(2) |
| 0.003 | 1102.1 | 391.4 | 2.82 | miR-224 |
| 0.004 | 2727.0 | 1345.5 | 2.03 | miR-19a |
| 0.004 | 6342.0 | 3604.1 | 1.76 | miR-106b |
| 0.005 | 552.2 | 913.5 | 0.6 | miR-21* |
| 0.005 | 422.1 | 705.5 | 0.6 | miR-708 |
| 0.005 | 1847.7 | 4044.1 | 0.46 | miR-451-DICER1 |

Figure 15

Supplementary Table 8. The miRNAs differentially expressed in the molecular subtypes of IDC (false detection rate <0.05).

| Parametric p-value | <0.1 | Basal | Her2 | LumA | LumB | miRNA |
|---|---|---|---|---|---|---|
| 9e-07 | 337.47 | 785.96 | 291.38 | 232.64 | 405.18 | miR-18a |
| 2.58e-05 | 552.62 | 1328.69 | 355.25 | 267.48 | 213.59 | miR-224 |
| 3.35e-05 | 257.95 | 208.11 | 274.73 | 380.83 | 639.46 | miR-190b |
| 2.25e-04 | 410.49 | 707.64 | 283.71 | 259.73 | 200 | miR-452 |
| 3.16e-04 | 1113.83 | 2501.76 | 998.14 | 875.59 | 1461.08 | miR-92a(2) |
| 0.001 | 1884.34 | 4515.33 | 1915.66 | 2313.42 | 2397.71 | miR-17 |
| 0.001 | 3050.34 | 1739.35 | 3021.88 | 1617.89 | 4820.32 | miR-425 |
| 0.001 | 372 | 905.03 | 570.09 | 325.55 | 478.56 | miR-155 |
| 0.002 | 329.61 | 435.06 | 243.02 | 203.07 | 271.4 | miR-9(3) |

Figure 16

Table 9. miRNAs associated with time to metastasis in IDC.

| Parametric p-value | Permutation p-value | Hazard Ratio | miRNA |
|---|---|---|---|
| 2.03E-04 | 1.000E-04 | 2.26 | let-7b |
| 4.30E-04 | 3.000E-04 | 2.49 | miR-127-3p |
| 7.29E-04 | 0.002 | 1.58 | miR-423-3p |
| 0.001 | 0.002 | 0.46 | miR-21 |
| 0.002 | 0.002 | 2.02 | miR-143* |
| 0.003 | 0.003 | 2.97 | let-7i |
| 0.004 | 0.005 | 2.29 | let-7c |
| 0.011 | 0.011 | 2.01 | miR-574-3p |
| 0.013 | 0.014 | 2.00 | miR-221 |
| 0.015 | 0.020 | 1.39 | miR-423-5p |
| 0.018 | 0.015 | 1.39 | miR-210 |
| 0.018 | 0.020 | 0.70 | miR-142-5p |
| 0.021 | 0.025 | 1.91 | miR-106b* |
| 0.029 | 0.028 | 1.77 | miR-197 |
| 0.030 | 0.029 | 0.70 | miR-374a |
| 0.035 | 0.034 | 0.73 | miR-142-3p |
| 0.038 | 0.036 | 2.02 | miR-376a-3p(2) |
| 0.039 | 0.035 | 2.18 | miR-145* |
| 0.045 | 0.043 | 1.67 | miR-185 |
| 0.045 | 0.044 | 1.62 | miR-320-RNASEN |
| 0.048 | 0.051 | 1.53 | miR-99a |
| 0.049 | 0.046 | 1.60 | miR-24(2) |

Figure 17

| Table 10. miRNAs associated with overall survival in IDC. | | | |
|---|---|---|---|
| Parametric p-value | Permutation p-value | Hazard Ratio | miRNA |
| 0.001 | 0.002 | 1.67 | miR-423-3p |
| 0.002 | 0.004 | 0.50 | miR-21 |
| 0.003 | 0.003 | 2.06 | let-7b |
| 0.005 | 0.005 | 2.32 | miR-652 |
| 0.006 | 0.004 | 1.54 | miR-210 |
| 0.006 | 0.006 | 3.13 | let-7i |
| 0.006 | 0.006 | 2.30 | miR-574-3p |
| 0.007 | 0.009 | 2.65 | miR-376a-3p(2) |
| 0.010 | 0.009 | 1.96 | miR-143* |
| 0.011 | 0.015 | 2.29 | miR-221 |
| 0.013 | 0.012 | 1.98 | miR-320-RNASEN |
| 0.013 | 0.016 | 2.16 | miR-28-3p |
| 0.013 | 0.011 | 2.12 | miR-127-3p |
| 0.017 | 0.021 | 1.44 | miR-423-5p |
| 0.019 | 0.022 | 1.84 | miR-106b* |
| 0.029 | 0.033 | 1.54 | miR-378 |
| 0.032 | 0.035 | 1.63 | miR-181a(2) |
| 0.033 | 0.040 | 1.59 | miR-22 |
| 0.034 | 0.029 | 1.79 | miR-197 |
| 0.049 | 0.050 | 1.81 | let-7c |
| 0.050 | 0.046 | 0.69 | miR-374a |

Figure 18

Table 11. Functional analysis of genes inversely related to miR-210 in the normal/DCIS and DCIS/IDC transitions, performed using the DAVID database. Twenty-five genes from the Genetic association DB are linked to breast cancer (Enrichment p-value = 1.4E-3). Breast cancer was the only disease associated to these genes.

| GENE_SYMBOL | GENE NAME |
| --- | --- |
| MTRR | 5-methyltetrahydrofolate-homocysteine methyltransferase reductase |
| AKAP10 | A kinase (PRKA) anchor protein 10 |
| FANCD2 | Fanconi anemia, complementation group D2 |
| RAD23B | RAD23 homolog B (S. cerevisiae) |
| AR | androgen receptor |
| BRCA1 | breast cancer 1, early onset |
| BUB3 | budding uninhibited by benzimidazoles 3 homolog (yeast) |
| CDH1 | cadherin 1, type 1, E-cadherin (epithelial) |
| CASP8 | caspase 8, apoptosis-related cysteine peptidase |
| CLCA2 | chloride channel accessory 2 |
| DHFR | dihydrofolate reductase |
| EGFR | epidermal growth factor receptor (erythroblastic leukemia viral (v-erb-b) oncogene homolog, avian) |
| EHMT1 | euchromatic histone-lysine N-methyltransferase 1 |
| GMNN | geminin, DNA replication inhibitor |
| GSR | glutathione reductase |
| HFE | Hemochromatosis |
| MMP12 | matrix metallopeptidase 12 (macrophage elastase) |
| NBN | Nibrin |
| PON2 | paraoxonase 2 |
| PARP1 | poly (ADP-ribose) polymerase 1 |
| PGAP3 | post-GPI attachment to proteins 3 |
| RB1 | retinoblastoma 1 |
| RNASEL | ribonuclease L (2',5'-oligoisoadenylate synthetase-dependent) |
| SOD1 | superoxide dismutase 1, soluble |
| ZNF350 | zinc finger protein 350 |

Figure 19

| Covariates | | | n=466 |
|---|---|---|---|
| Disease Stage, no (%) | I | 94 | 20·2 |
| | IIA | 157 | 33·8 |
| | IIB | 97 | 20·9 |
| | IIIA | 65 | 14·0 |
| | IIIB | 12 | 2·6 |
| | IIIC | 17 | 3·7 |
| | IV | 12 | 2·6 |
| Lymph Node Involvement, no (%) | N0 | 197 | 44·4 |
| | N1 | 168 | 37·8 |
| | N2 | 55 | 12·4 |
| | N3 | 24 | 5·4 |
| M stage, no (%) | M0 | 419 | 89·9 |
| | M1 | 12 | 2·6 |
| T stage, no (%) | T1 | 146 | 31·3 |
| | T2 | 267 | 56·2 |
| | T3 | 38 | 8·2 |
| | T4 | 18 | 3·6 |
| ER, no (%) | Negative | 110 | 24·3 |
| | Positive | 342 | 75·7 |
| PR, no (%) | Negative | 151 | 33·4 |
| | Positive | 301 | 66·6 |
| HER2, no (%) | Negative | 255 | 79·7 |
| | Positive | 65 | 20·3 |
| TNBC, no (%) | Non TN | 256 | 80·0 |
| | TN | 64 | 20·0 |
| Age, years, no (%) | <=45 | 102 | 21·9 |
| | 46-55 | 105 | 22·5 |
| | 56-65 | 141 | 30·3 |
| | >65 | 118 | 25·3 |
| *TP53* Mutation, no (%) | Mutated | 165 | 35·4 |
| | Wild-type | 301 | 64·6 |
| *PIK3CA* Mutation, no (%) | Mutated | 142 | 30·5 |
| | Wild-type | 324 | 69·5 |
| Molecular subtype, no (%) | Basal-like | 104 | 22·4 |
| | HER2-enriched | 49 | 10·5 |
| | Luminal A | 110 | 23·7 |
| | Luminal B | 148 | 31·8 |

ER, estrogen receptor; PR, progesterone receptor

Figure 20

| | | | | RNA Signatures (AUC of ROC curves) | | | | | |
|---|---|---|---|---|---|---|---|---|---|
| Cohort | No. of patients | Clinical Endpoint | RNA profile | Integrated 24-mRNA 10-miRNA | 10-miRNA | GGI 97-gene | 76-mRNA | 70-mRNA | 21-mRNA |
| TCGA IDC | 466 | OS | mRNA/ miRNA | 0·71 (p<0·001) | not significant[§] | 0·60 (p=0·053) | not significant[§] | not significant[§] | not significant[§] |
| Hatzis | 508 | DRFS | mRNA | 0·62 (p<0·001) | na[#] | 0·66 (p<0·001) | 0·62 (p=0·001) | 0·62 (p<0·001) | 0·63 (p<0·001) |
| Kao | 327 | OS | mRNA | 0·58 (p=0·050) | na[#] | 0·58 (p=0·051) | 0·58 (p=0·038) | 0·64 (p=0·005) | 0·65 (p<0·001) |
| UK | 207 | DRFS | mRNA/ miRNA | 0·65 (p=0·001) | 0·76 (p<0·001) | 0·66 (p=0·001) | 0·66 (p=0·003) | 0·73 (p<0·001) | 0·68 (p<0·001) |
| Wang | 286 | DRFS | mRNA | 0·61 (p=0·002) | na[#] | 0·59 (p=0·017) | 0·65 (p<0·001) | 0·57 (p=0·051) | 0·62 (p<0·001) |
| TRANSBIG | 198 | OS | mRNA | 0·65 (p=0·008) | na[#] | 0·70 (p=0·002) | 0·64 (p=0·023) | 0·61 (p=0·057) | 0·65 (p<0·001) |
| Bos | 195 | DRFS | mRNA | 0·69 (p=0·012) | na[#] | 0·67 (p=0·031) | not significant[§] | 0·69 (p=0·016) | 0·74 (p=0·003) |
| TNBC | 383 | DRFS | mRNA | 0·67 (p<0·001) | na[#] | 0·65 (p<0·001) | 0·65 (p<0·001) | 0·68 (p<0·001) | 0·66 (p<0·001) |

[§]The AUC for the ROC curves are reported for each significant cohort/signature combination. Not significant, p>>0·05. The permutation p value was computed for testing the null hypothesis (AUC=0·5) using 1000 permutations.
[#]na, no assessment was possible, since the miRNA signature could not be applied to a mRNA only profile.

GEO accession numbers:
UK cohort, GSE22216 and GSE22219; Buffa FM, Camps C, Winchester L, et al. microRNA-associated progression pathways and potential therapeutic targets identified by integrated mRNA and microRNA expression profiling in breast cancer. *Cancer research* 2011; 71(17): 5635-45.
Kao cohort, GSE20685; Kao KJ, Chang KM, Hsu HC, Huang AT. Correlation of microarray-based breast cancer molecular subtypes and clinical outcomes: implications for treatment optimization. *BMC Cancer* 2011; 11: 143.
Wang cohort, GSE2034; Wang Y, Klijn JG, Zhang Y, et al. Gene-expression profiles to predict distant metastasis of lymph-node-negative primary breast cancer. *Lancet* 2005; 365(9460): 671-9.
Hatzis cohort, GSE25066; Hatzis C, Pusztai L, Valero V, et al. A genomic predictor of response and survival following taxane-anthracycline chemotherapy for invasive breast cancer. *JAMA* 2011; 305(18): 1873-81.
Bos cohort, GSE12276; Bos PD, Zhang XH, Nadal C, et al. Genes that mediate breast cancer metastasis to the brain. *Nature* 2009; 459(7249): 1005-9.
TNBC cohort, GSE31519; Rody A, Karn T, Liedtke C, et al. A clinically relevant gene signature in triple negative and basal-like breast cancer. *Breast cancer research : BCR* 2011; 13(5): R97.
TRANSBIG cohort, GSE7390; Desmedt C, Piette F, Loi S, et al. Strong time dependence of the 76-gene prognostic signature for node-negative breast cancer patients in the TRANSBIG multicenter independent validation series. *Clin Cancer Res* 2007; 13(11): 3207-14.
the TCGA IDC was obtained from the TCGA data portal. Koboldt DC, Fulton RS, McLellan MD, et al. Comprehensive molecular portraits of human breast tumours. *Nature* 2012.

Figure 21

| DNA methylated CpG sites associated with Overall Survival in IDC ||||
|---|---|---|---|
| Gene Symbol | Probe | Cox Regression p value | Hazard Ratio |
| PDSS2 | cg01917202 | 0.007 | 0.13 |
| PDSS2 | cg26312839 | 0.009 | 0.15 |
| PDSS2 | cg09699384 | 0.020 | 0.21 |
| PDSS2 | cg21122684 | 0.033 | 0.23 |
| PIGP / TTC3 | cg27382599 | 0.003 | 0.14 |
| PIGP / TTC3 | cg14220272 | 0.034 | 0.42 |
| PIK3CA | cg13435326 | 0.013 | 0.65 |
| PIK3CA | cg22384366 | 0.029 | 0.66 |
| PIK3CA | cg01753796 | 0.037 | 0.75 |
| PIK3CA | cg22806557 | 0.038 | 0.39 |
| RC3H2 | cg14500628 | 0.019 | 1.95 |
| SCYL2 / DEPDC4 | cg18548043 | 0.012 | 20.06 |
| SCYL2 / DEPDC4 | cg02430089 | 0.016 | 0.33 |
| SCYL2 / DEPDC4 | cg11940847 | 0.041 | 5.80 |
| SMG1 | cg01079632 | 0.007 | 0.58 |
| SMG1 | cg27302229 | 0.009 | 4.02 |
| SMG1 | cg03614442 | 0.047 | 0.40 |
| THAP2 / ZFC3H1 | cg19966154 | 0.004 | 2.88 |
| THAP2 / ZFC3H1 | cg21830480 | 0.041 | 0.57 |
| TOPBP1 | cg12655621 | 0.001 | 3.38 |
| TOPBP1 | cg13024018 | 0.004 | 3.72 |
| TRIM23 / C5orf44 | cg08307039 | 0.005 | 0.21 |
| TTC3 | cg00302270 | 0.001 | 0.48 |
| UBR5 | cg12517050 | 1.500E-06 | 0.31 |
| UBR5 | cg14897263 | 0.018 | 0.71 |
| UBR5 | cg15001633 | 0.021 | 1.71 |
| UBXN7 | cg15925179 | 0.031 | 0.44 |
| UBXN7 | cg03191919 | 0.042 | 0.77 |
| WDR20/HSP90AA1 | cg04414295 | 0.009 | 1.73 |
| ZFC3H1 / THAP2 | cg07821172 | 0.008 | 0.37 |
| ZFC3H1 / THAP2 | cg03191116 | 0.028 | 0.35 |
| ZNF292 | cg15511114 | 0.044 | 2.10 |

* Cox regression, p value <0.05.

Figure 27 Cont.

| The negative correlation between mRNA expression and CpG DNA methylation of PIK3CA (FDR <0.001) |||||
|---|---|---|---|---|
| Correlation Coefficient (Spearman) | Parametric P-value | FDR | Unique ID (Illumina 450K) | Genomic Coordinates |
| -0.217 | 3.06E-05 | 0.0004 | cg01792902 | chr3:178864927-178864976 |
| -0.249 | 1.70E-06 | 6.53E-05 | cg22806557 | chr3:178865282-178865331 |
| -0.242 | 8.76E-05 | 0.0009 | cg00658016 | chr3:178865679-178865728 |
| 0.256 | 8.00E-07 | 4.30E-05 | cg19522332 | chr3:178866005-178866054 |
| -0.337 | < 1e-07 | < 1e-07 | cg22384366 | chr3:178867005-178867054 |
| -0.289 | 2.00E-07 | 2.31E-05 | cg01753796 | chr3:178867106-178867155 |

Figure 26

| DNA methylated CpG sites associated with Overall Survival in IDC ||||
|---|---|---|---|
| Gene Symbol | Probe | Cox Regression p value | Hazard Ratio |
| ADAT1 | cg02576610 | 0.033 | 0.60 |
| ANKRD52 | cg10803923 | 4.127E-04 | 0.18 |
| ANKRD52 | cg23759554 | 0.012 | 0.58 |
| APC | cg11057897 | 0.004 | 0.47 |
| APC | cg18315896 | 0.029 | 2.75 |
| APC | cg25922032 | 0.036 | 2.94 |
| ARSK / TTC37 | cg01559436 | 0.009 | 6.02 |
| BIRC6 | cg12233946 | 0.003 | 0.35 |
| BIRC6 | cg20351608 | 0.015 | 3.70 |
| BIRC6 | cg11971852 | 0.020 | 0.45 |
| C10orf18 | cg09262442 | 0.013 | 0.65 |
| C10orf18 | cg08452525 | 0.015 | 0.52 |
| C10orf18 | cg21302771 | 0.032 | 1.85 |
| C2CD2 | cg00054774 | 0.021 | 0.76 |
| C2CD2 | cg04723534 | 0.049 | 0.83 |
| CEP350 | cg21944557 | 0.014 | 2.54 |
| CHD9 | cg04770195 | 0.001 | 0.57 |
| CHD9 | cg05788994 | 0.008 | 2.48 |
| CHD9 | cg08944236 | 0.028 | 0.78 |
| CHM | cg19000468 | 0.049 | 0.53 |
| CPT1A | cg03855388 | 8.100E-06 | 0.63 |
| CPT1A | cg18262591 | 1.250E-04 | 0.57 |
| CPT1A | cg20629021 | 1.751E-04 | 0.49 |
| CPT1A | cg01926073 | 5.880E-04 | 0.41 |
| CPT1A | cg20809737 | 6.307E-04 | 0.58 |
| CPT1A | cg13491471 | 0.002 | 0.58 |
| CPT1A | cg22911054 | 0.004 | 0.69 |
| CPT1A | cg19964581 | 0.005 | 0.55 |
| CPT1A | cg00574958 | 0.008 | 0.68 |
| CPT1A | cg12031060 | 0.008 | 0.55 |
| CPT1A | cg09737197 | 0.009 | 0.78 |
| CPT1A | cg26192826 | 0.011 | 1.53 |
| CPT1A | cg10970946 | 0.013 | 0.56 |
| CPT1A | cg19081843 | 0.014 | 2.36 |
| CPT1A | cg14249520 | 0.017 | 0.70 |
| CPT1A | cg17058475 | 0.029 | 0.77 |
| CPT1A | cg23756264 | 0.030 | 0.58 |
| CPT1A | cg11867574 | 0.032 | 0.58 |
| CPT1A | cg10553894 | 0.043 | 0.75 |
| CPT1A | cg26989316 | 0.044 | 0.70 |
| DAAM1 | cg18819791 | 0.003 | 0.63 |
| DAAM1 | cg17326597 | 0.017 | 0.71 |
| DAAM1 | cg19768143 | 0.020 | 0.65 |
| DAAM1 | cg23315932 | 0.021 | 0.74 |
| DAAM1 | cg05342987 | 0.022 | 1.98 |

Figure 27

| DNA methylated CpG sites associated with Overall Survival in IDC | | | |
|---|---|---|---|
| Gene Symbol | Probe | Cox Regression p value | Hazard Ratio |
| DAAM1 | cg23862792 | 0.027 | 0.34 |
| DIP2B | cg16248432 | 2.832E-04 | 0.60 |
| DIP2B | cg23925540 | 0.009 | 0.52 |
| DIP2B | cg05827208 | 0.013 | 0.16 |
| DIP2B | ch.12.1034102F | 0.038 | 0.51 |
| DIP2B | cg05512157 | 0.047 | 0.72 |
| DPY19L3 | cg09577932 | 0.022 | 0.64 |
| DPY19L3 | cg11416386 | 0.026 | 0.24 |
| DPY19L3 | cg02871028 | 0.033 | 3.71 |
| FAM91A1 | cg00189906 | 6.218E-04 | 0.13 |
| GADD45GIP1 | cg03539717 | 6.240E-05 | 0.41 |
| GADD45GIP1 | cg14393411 | 0.029 | 0.24 |
| GBE1 | cg02980152 | 0.011 | 3.15 |
| GBE1 | cg16472210 | 0.014 | 9.15 |
| GBE1 | cg03785807 | 0.036 | 0.40 |
| GMCL1 | cg04590956 | 0.019 | 0.25 |
| GMCL1 | cg19393587 | 0.021 | 0.65 |
| GMCL1 | cg19598605 | 0.036 | 0.58 |
| GOLGA4 | cg12435059 | 0.001 | 0.39 |
| GOLGA4 | cg09456388 | 0.009 | 7.80 |
| HSP90AA1 | cg11789371 | 0.021 | 0.76 |
| MAN2A1 | cg23500208 | 0.006 | 0.66 |
| MAN2A1 | cg07541465 | 0.015 | 1.59 |
| MAN2A1 | cg04020816 | 0.022 | 1.48 |
| MAN2A1 | cg19117777 | 0.025 | 3.06 |
| MAN2A1 | cg10569493 | 0.041 | 0.75 |
| ME1 | cg16701167 | 0.009 | 0.75 |
| ME1 | cg01354879 | 0.011 | 0.71 |
| MPND | cg12985235 | 0.008 | 0.59 |
| NCOA2 | cg22304838 | 2.726E-04 | 0.41 |
| NCOA2 | cg16282160 | 8.596E-04 | 0.55 |
| NCOA2 | cg13312403 | 0.004 | 0.48 |
| NCOA2 | cg24536624 | 0.005 | 0.40 |
| NCOA2 | cg02492405 | 0.006 | 1.45 |
| NCOA2 | cg24857609 | 0.020 | 0.48 |
| NCOA2 | cg11197908 | 0.030 | 0.50 |
| NCOA2 | cg20679659 | 0.044 | 0.37 |
| NCOA2 | cg20699548 | 0.049 | 0.71 |
| OTUD6B | cg06670766 | 8.910E-04 | 0.22 |
| OTUD6B | cg25987774 | 0.017 | 3.74 |
| OTUD6B | cg06216901 | 0.018 | 0.24 |
| OTUD6B | cg23863900 | 0.020 | 2.32 |
| OTUD6B | cg18888595 | 0.042 | 0.42 |
| PDSS2 | cg26954751 | 8.150E-04 | 0.59 |
| PDSS2 | cg06931193 | 0.004 | 2.19 |
| PDSS2 | cg14957497 | 0.005 | 0.13 |
| PDSS2 | cg01959896 | 0.006 | 2.72 |

Figure 27 Cont.

| Twenty four mRNAs and ten miRNAs were associated with clinical outcome and validated across independent IDC subclasses. | |
|---|---|
| Gene | Validated Subgroups |
| ADAT1 | [StI, StIIA] |
| ANKRD52 | [StI, StIIA, StIIB], [PI3K, TP53 PIK3CA] |
| BIRC6 | [StI, StIIA] |
| C10orf18 | [StI, StIIA] |
| C2CD2 | [LumA, BL] |
| CHD9 | [StI, StIIB] |
| CHM | [StI, StIIA] |
| CPT1A | [LumA, LumB], [LumB Marg Neg, BL Marg Neg], [N+ Horm Rec+ ERBB2- Marg Neg, TNBC Marg Neg], [N0, N+], [StIIB, StIIIA], [PI3K, noMajorMut], [Low MutRate, Med MutRate] |
| DAAM1 | [StI, StIIA] |
| DIP2B | [StIIB, StIIIA], [TP53, PI3K] |
| DPY19L3 | [StI, StIIB, StIIA] |
| FAM91A1 | [N0, N+] |
| GMCL1 | [StIIA, StIIB, StIIIA], [PI3K, noMajorMut] |
| hsa-miR-103 | [ERBB2+, TNBC] |
| hsa-miR-1307 | [TP53, PI3K] |
| hsa-miR-148b | [TP53, MAPK] |
| hsa-miR-324 | [Low MutRate, Med MutRate] |
| hsa-miR-326 | [N0, N+] |
| hsa-miR-328 | [N0, N+], [StI, StIIB, StIIIA], [Low MutRate, Med MutRate] |
| hsa-miR-365 | [LumA, BL] |
| hsa-miR-484 | [N0, N+], [N0 Marg Neg, N+ Marg Neg] |
| hsa-miR-874 | [N0, N+], [N0 Marg Neg, N+ Marg Neg], [StI, StIIIA], [N1, N23] |
| hsa-miR-93 | [N0 Marg Neg, N+ Marg Neg] |
| ME1 | [LumA, LumB] |
| NCOA2 | [LumB Marg Neg, BL Marg Neg] |
| OTUD6B | [N0, N+], [Low MutRate, Med MutRate] |
| PDSS2 | [N0, N+], [Low MutRate, High MutRate] |
| PIK3CA | [LumA, BL], [Low MutRate, High MutRate] |
| SMG1 | [StI, StIIA] |
| TRIM23 | [StIIA, StIIB] |
| TTC3 | [StI, StIIB] |
| UBR5 | [StIIA, StIIB] |
| UBXN7 | [HER2 Marg Neg, BL Marg Neg], [StI, StIIA], [PI3K, noMajorMut], [Low MutRate, High MutRate] |
| ZFC3H1 | [StI, StIIA] |

\* The coding genes were restricted further by DNA methylation/OS analysis and presence of somatic mutations. Square brackets indicate the independent IDC subclasses used for validation. Marg Neg=Margin Negative. Horm Rec+ means ER+ and/or PR+ tumors. Mutation rate: Low <25 mutations in exome, 25<=Medium<=50, High>50. Mutations: PI3K (PIK3CA, AKT1, PTEN, PIK3R1), TP53 PIK3CA are double mutants. noMajorMut= others than PI3K, TP53, MAPK and GATA3.

Figure 28

| The integrated 34-gene RNA linear risk predictor for OS in the TCGA IDC cohort (n=466) | | |
|---|---|---|
| Gene | Weights ($w_i$) | Cox regression p value |
| PIK3CA | 0.039572 | 6.4e-06 |
| DIP2B | 0.102922 | 1.24e-05 |
| hsa-miR-874 | 0.307278 | 1.33e-05 |
| CPT1A | 0.22432 | 1.66e-05 |
| DPY19L3 | 0.056377 | 3.22e-05 |
| hsa-miR-328 | 0.089724 | 3.41e-05 |
| hsa-miR-484 | 0.176961 | 5.28e-05 |
| BIRC6 | 0.065273 | 5.32e-05 |
| GMCL1 | 0.05703 | 6.11e-05 |
| ZFC3H1 | 0.061551 | 0.000118 |
| UBXN7 | 0.045594 | 0.0001477 |
| hsa-miR-148b | 0.106935 | 0.0001767 |
| CHD9 | 0.0643 | 0.0002013 |
| CHM | 0.046437 | 0.0002522 |
| TTC3 | 0.123665 | 0.0002776 |
| PDSS2 | 0.143272 | 0.0003798 |
| ME1 | 0.132666 | 0.0004285 |
| ADAT1 | 0.066575 | 0.0004316 |
| hsa-miR-326 | -0.07944 | 0.0004535 |
| ANKRD52 | 0.046981 | 0.0004932 |
| FAM91A1 | -0.07689 | 0.0006084 |
| NCOA2 | -0.08572 | 0.0006663 |
| DAAM1 | 0.161545 | 0.0007841 |
| UBR5 | -0.081458 | 0.0009532 |
| TRIM23 | 0.046902 | 0.0010073 |
| OTUD6B | -0.16024 | 0.001256 |
| SMG1 | 0.059308 | 0.0012689 |
| C2CD2 | 0.18034 | 0.0014376 |
| hsa-miR-1307 | 0.089849 | 0.0014402 |
| C10orf18 | -0.00228 | 0.0016472 |
| hsa-miR-365-2 | 0.120807 | 0.0023067 |
| hsa-miR-324 | 0.122125 | 0.0030918 |
| hsa-miR-103-1 | 0.064842 | 0.0032281 |
| hsa-miR-93 | 0.037021 | 0.0210513 |

*A new sample was predicted as high risk if its prognostic index was larger than 0.061. The prognostic index was computed by the formula $\sum_i w_i x_i - 11.69$ where $w_i$ and $x_i$ were respectively the weight and $\log_2$ RNA normalized reads for the $i$-th gene. Hazard ratio was the ratio of hazards for a two-fold change in the gene expression level.

BREAST CANCER BIOMARKER SIGNATURES FOR INVASIVENESS AND PROGNOSIS

CROSS-REFERENCE TO RELATED APPLICATIONS

This application claims the benefit of U.S. Provisional Application No. 61/588,790 filed Jan. 20, 2012, the entire disclosure of which is expressly incorporated herein by reference for all purposes.

STATEMENT REGARDING FEDERALLY SPONSORED RESEARCH

This invention was made with government support under Grant Nos. U01-CA152758 and U01-CA154200 awarded by the National Institutes of Health. The government has certain rights in the invention.

TECHNICAL FIELD

This invention relates generally to the field of molecular biology. More particularly, it concerns cancer-related technology. Certain aspects of the invention include application in diagnostics, therapeutics, and prognostics of breast cancers.

BACKGROUND OF THE INVENTION

Breast cancer (BC) is a complex disease, characterized by heterogeneity of genetic alterations and influenced by several environmental factors. Ductal carcinoma in situ (DCIS) is a heterogeneous group of lesions reflecting the proliferation of malignant cells within the breast ducts without invasion through the basement membrane. About 80% of all breast cancers are invasive ductal carcinomas (IDC), the most frequent type of BC. Breast tumors of distinct molecular subtypes (luminal A/B, HER2+, and basal-like) have dramatically different mRNA profiles.

Until 1980, DCIS was diagnosed rarely and represented <1% of BC. With the increased use of mammography, DCIS became the most rapidly increasing subset of BC, accounting for 15%-25% of newly diagnosed BC cases in the US.

MicroRNA (miRNA) is a class of conserved non-coding RNAs with regulatory functions, which exerts important roles in cancer. Microarray analysis of miRNAs has been generating much new knowledge in recent years. There is still a need for information about the function and activity of miRNAs, as well as for methods and compositions that can be used for their characterization and analysis. However, genome-wide mRNA expression studies failed to identify progression stage-specific genes.

SUMMARY OF THE INVENTION

In a first broad aspect, described herein is breast cancer signature that indicates an increased risk for poor prognosis breast cancer. The signature comprising the determination of an alteration in levels of a miRNA/mRNA signature in a test sample of tissue from the human subject. In one embodiment, the miRNA/mRNA signature consisting of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1. An alteration in the levels of the miRNA and mRNA gene products in the test sample, relative to the level of corresponding levels of miRNA and mRNA gene products in a control sample of cancer free tissue, is indicative of the human subject having a poor survival prognosis for BC.

In another aspect, there is provided herein, a method of determining whether a human subject has a poor survival prognosis for breast cancer (BC). The method generally includes measuring the level of a miRNA/mRNA signature in a test sample of tissue from the human subject (where the miRNA/mRNA signature consists of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1. The method also generally includes determining the survival prognosis of the subject; wherein an alteration in the levels of the miRNA and mRNA gene products in the test sample, relative to the level of a corresponding levels of miRNA and mRNA gene products in a control sample of cancer free tissue, is indicative of the human subject having a poor survival prognosis for BC.

In another aspect, there is provided herein, a method of diagnosing whether a human subject has, or is at risk for developing, a BC associated with a poor prognosis, comprising: (1) reverse transcribing RNA from a test sample of tissue obtained from the human subject to provide a set of target oligodeoxynucleotides; (2) hybridizing the target oligodeoxynucleotides to a microarray comprising miRNA-specific probe oligonucleotides to provide a hybridization profile for the test sample wherein the microarray comprises miRNA-specific probe oligonucleotides for a the miRNA/mRNA signature consisting of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1; (3) comparing the test sample hybridization profile to a hybridization profile generated from a control sample of metastasis-free tissue, and, (4) diagnosing whether the human subject has or is at risk of developing a BC associated with a poor prognosis based on an alteration in the miRNA/mRNA gene product signature.

In certain embodiments, the step of determining the survival prognosis of the subject having an invasive ductal carcinoma (IDC) breast cancer (BC).

In certain embodiments, the step of determining the survival prognosis of the subject predicts overall survival (OS).

In certain embodiments, a signature set of miRNAs and mRNA hybridize to probes that are specific for such miRNAs and mRNA, relative to the control sample, is indicative of a prognosis of poor survival in human patients.

In another aspect, there is provided herein a method for determining if a human subject having breast cancer (BC) has a poor survival outcome comprising: assaying a nucleic acid sample obtained from breast cells of the human subject to determine the expression level of a miRNA/mRNA signature in the nucleic acid sample, the miRNA/mRNA signature consisting of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR- 93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1; and, determining that the human subject has a poor survival outcome, if there is an alteration in the expression levels of miRNA/mRNA signature in the nucleic acid sample, as compared to a control nucleic acid sample.

In another aspect, there is provided herein a DNA chip for testing for a colon cancer-related disease, on which a probe has been immobilized to assay a miRNA/mRNA signature consisting of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1.

In another aspect, there is provided herein an article of manufacture comprising: at least one capture reagent that binds to at least one marker for a miRNA/mRNA signature consisting of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1.

In another aspect, there is provided herein a kit for screening for breast cancer, wherein the kit comprises: one or more reagents of at least one marker for: miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1.

In certain embodiments, the presence of the marker is detected using a reagent comprising an antibody or an antibody fragment which specifically binds with at least one marker.

In certain embodiments, the reagent is labeled, radio-labeled, or biotin-labeled, and/or wherein the antibody or antibody fragment is radio-labeled, chromophore-labeled, fluorophore-labeled, or enzyme-labeled.

In certain embodiments, the reagent comprises one or more of: an antibody, a probe to which the reagent is attached or is attachable, and an immobilized metal chelate.

In another aspect, there is provided herein a microarray for predicting the presence of a breast cancer-related disease in a subject comprising an antibody directed a miRNA/mRNA signature consisting of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1.

In certain embodiments, a level of expression of the marker is assessed by detecting the presence of a transcribed polynucleotide or portion thereof, wherein the transcribed polynucleotide comprises a coding region of the marker.

In certain embodiments, the sample is a breast cancer-associated body fluid or tissue.

In certain embodiments, the sample comprises cells obtained from the patient.

In certain embodiments, at least miRNA/mRNA signature includes isolated variants or biologically-active fragments or functional equivalents thereof, or antibodies that bind thereto.

In certain embodiments, the breast cancer-related disease is an invasive ducal carcinoma (IDC).

In certain embodiments, the sample comprises cells obtained from the patient taken over time.

In certain embodiments, the method further comprises designing a treatment plan based on the diagnosis.

In certain embodiments, the method further comprises administration of a treatment based on the diagnosis.

In certain embodiments, the standard miRNA and/or mRNA expression levels are from the representative pool of individuals and is a mean, median or other statistically manipulated or otherwise summarized or aggregated representative miRNA and/or mRNA expression levels for the miRNA and miRNA levels in the control tissues in the subject.

In another aspect, there is provided herein a computer-readable medium comprising a database having a plurality of digitally-encoded reference profiles, wherein at least a first reference profile represents a level of at least a miRNA/mRNA signature in one or more samples from one or more subjects exhibiting an indicia of a breast cancer-related disease response, wherein the miRNA/mRNA signature consisting of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1.

In certain embodiments, the computer readable medium includes at least a second reference profile that represents a level of at least one additional miRNA or mRNA in one or more samples from one or more subjects exhibiting indicia of a breast cancer-related disease response; or subjects having a breast cancer-related disease.

In another aspect, there is provided herein a computer system for determining whether a subject has, is predisposed to having, or has a poor survival prognosis for, a breast cancer-related disease, comprising the database of claim 17, and a server comprising a computer-executable code for causing the computer to receive a profile of a subject, identify from the database a matching reference profile that is diagnostically relevant to the subject profile, and generate an indication of whether the subject has, or is predisposed to having, a breast cancer-related disease.

In another aspect, there is provided herein a computer-assisted method for evaluating the presence, absence, nature or extent of a breast cancer-related disease in a subject, comprising:

(1) providing a computer comprising a model or algorithm for classifying data from a sample obtained from the subject,
wherein the classification includes analyzing the data for the presence, absence or amount of at least one miRNA/mRNA signature, and
wherein the a miRNA/mRNA signature consisting of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsamiR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1;

(2) inputting data from the biological sample obtained from the subject; and, (3) classifying the biological sample to indicate the presence, absence, nature or extent of a breast cancer-related disease.

In another aspect, there is provided herein a method for predicting a prognosis in a breast cancer patient comprising: detecting a test expression level of a set a signature in a biological test sample from a subject having breast cancer; assigning a risk score to the test expression level; and predicting the a poor prognosis when the test expression level is assigned a high risk score; and predicting a good prognosis when the test expression level is assigned a low risk score, wherein the signature comprises a miRNA/mRNA signature consisting of miRNA gene products: hsa-miR-103, hsa-miR-1307, hsa-miR-148b, hsa-miR-324, hsa-miR-326, hsa-miR-328, hsa-miR-365, hsa-miR-484, hsa-miR-874 a, hsa-miR-93; and mRNA gene products: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7 and ZFC3H1.

In certain embodiments, the prognosis is overall cancer survival.

In certain embodiments, the test expression level is determined by microarray.

In certain embodiments, the test expression level is determined by RT-PCR.

In certain embodiments, the miRNA/mRNA signature comprises a statistically significant change in the expression of the miRNAs and mRNAs in a breast cell versus a breast cancer cell.

In another aspect, there is provided herein a marker for detecting breast invasive ductal carcinoma (IDC) in a subject, comprising a miR-210 gene product.

In another aspect, there is provided herein a method for detecting breast invasive ductal carcinoma in a subject, comprising detecting an increase in a miR-210 gene product, as compared to a test sample.

In another aspect, there is provided herein a microRNA signature for differentiating invasive ductal carcinoma (IDC) from ductal carcinoma in situ (DCIS), comprising: i) up-regulation of at least one of: let-7d, miR-181a, miR-210 and miR-221 in IDC; and, ii) down-regulation of at least one of: miR-10b, miR-126, miR-143, miR-218 and miR-335-5p in IDC.

In another aspect, there is provided herein a microRNA signature for overall-survival prognosis and for time-to-metastasis prognosis in a subject having breast cancer, comprising: miR-210, miR-21, miR-106b*, miR-197 and/or let-7i.

In another aspect, there is provided herein a microRNA marker for detecting transition from DCIS to IDC is a subject having breast cancer, comprising a miR-210 gene product.

In another broad aspect, there is provided herein a microRNA signature for differentiating invasive ductal carcinoma (IDC) from ductal carcinoma in situ (DCIS), comprising at least one of: let-7d, miR-210 and miR-221 down-regulated in in situ; and let-7d, miR-210 and miR-221 up-regulated in the invasive transition.

In another aspect, there is provided herein a microRNA signature for overall-survival and time-to-metastasis for breast cancer, comprising: miR-210, miR-21, miR-106b*, miR-197 and let-7i.

In another aspect, there is provided herein a marker for invasive transition, comprising protein coding genes with inversely related profiles to miR-210, where one or more of: BRCA1, FANCD, FANCF, PARP1, E-cadherin, Rb1 are activated in in situ and down-regulated in invasive carcinoma.

In another aspect, there is provided herein a marker for ductal carcinoma in situ, comprising at least one differential splicing isoform, such as a truncated EGFR lacking the kinase domain, wherein such marker is over-expressed only in ductal carcinoma in situ.

In another aspect, there is provided herein a method for identifying a patient as having a marker correlated with breast invasive ductal carcinoma (IDC) based on a increase in miR-210 expression comprising: a) analyzing miR-210 expression in a breast cancer sample from a patient suspected of having IDC; and, b) identifying the patient as i) having a marker correlated with IDC cancer if an increase in miR-210 expression in the sample from the patient compared to a noncancerous breast sample is detected or ii) as not having a marker correlated with IDC cancer if the increase fails to be detected.

In certain embodiments, the method further comprises analyzing the sample for: an increase in one or more of: let-7d, miR-221 and miR-181a; and/or a decrease in one or more of: miR-10b, miR-126, miR-143, miR-218 and miR-335-5p, compared to a noncancerous breast sample.

In another aspect, there is provided herein a method of diagnosing whether a subject has breast ductal invasive carcinoma (IDC), comprising: measuring the level of at least one miR-210 gene product in a test sample from the subject, wherein an increase in at least the level of the miR-210 gene product in the test sample, relative to the level of a corresponding miR gene product in a control sample, is indicative of the subject having a IDC.

In another aspect, there is provided herein a method of testing invasiveness of breast cancer in a subject, comprising: a) determining an expression level of at least one marker in a sample from the subject having breast carcinoma; the at least one marker including at least one miR-210 gene product; b) comparing the expression level determined in step (a) with a control expression level of the marker in a sample from a healthy subject; and c) judging the subject to have a diagnosis of breast invasive ductal carcinoma (IDC) when the result of the comparison in step (b) indicates that the expression level of the at least one marker in the test subject is higher than that in the control.

In certain embodiments, the sample comprises breast tissue.

In certain embodiments, the method steps are performed in vitro.

In another aspect, there is provided herein a method of diagnosing whether a subject has breast invasive ductal carcinoma (IDC), comprising: a) reverse transcribing RNA from a test sample obtained from the subject to provide a set of target oligodeoxynucleotides wherein the subject has breast IDC; b) hybridizing the target oligodeoxynucleotides to a microarray comprising miR-210 specific probe oligonucleotides to provide a hybridization profile for the test sample; and c) comparing the test sample hybridization profile to a hybridization profile generated from a control sample, wherein an increase in the signal of the miR-210 is indicative of the subject having IDC.

In certain embodiments, the method further comprises wherein step c) comprises comparing the test sample hybridization profile to a database, statistics, or table of miR levels associated with non-cancerous samples.

In certain embodiments, the method further comprises wherein at least one additional miR is included in the microarray.

In certain embodiments, the method further comprises wherein a level of expression of miR-210 gene product is assessed by detecting the presence of a transcribed polynucleotide or portion thereof, wherein the transcribed polynucleotide comprises a coding region of miR-210 gene product.

In certain embodiments, the method further comprises wherein the sample comprises cells obtained from the patient taken over time.

In certain embodiments, the method further comprises wherein the at least one miR-210 gene product includes isolated variants or biologically-active fragments thereof.

In another broad aspect, there is provided herein a kit comprising the marker/s described herein.

In certain embodiments, the method further comprises the kit further comprises instructions for screening a sample taken from a subject having, or suspected of having breast cancer.

In another aspect, there is provided herein a method of diagnosing breast invasive ductal carcinoma (IDC) in a subject, comprising: a) identifying the relative miR-210 expression compared to a control; and, b) diagnosing: i) IDC in the subject if the subject has increased miR-210 expression compared to the control; or, ii) diagnosing no IDC in the subject if the subject does not have increased miR-210 expression compared to the control.

In certain embodiments, the method further comprises identifying relative expression compared to control of at least one of: let-7d and miR-221.

In certain embodiments, the method further comprises wherein decreased let-7d and/or miR-221 expression compared to control confirms invasive breast cancer diagnosis.

In certain embodiments, the method further comprises designing a treatment plan based on the diagnosis.

In certain embodiments, the method further comprises administration of a treatment based on the diagnosis.

In certain embodiments, the method further comprises administering an anti-angiogenic treatment in the event that IDC is diagnosed.

In certain embodiments, the method further comprises determining prognosis based on the diagnosis.

In another aspect, there is provided herein a method of diagnosing breast invasive ductal carcinoma (IDC) cancer in a subject, comprising: a) identifying the relative miR-210 expression compared to control, identifying the let-7d expression compared to control and identifying the miR-221 expression compared to control; and b) diagnosing: i) IDC in the subject if the subject has increased miR-210 expression compared to control, increased let-7d expression compared to control, and increased miR-221 compared to control, or ii) diagnosing no IDC in the subject if the subject does not have increased miR-210 expression compared to control, increased let-7d expression compared to control, and increased miR-221 expression compared to control.

In another aspect, there is provided herein a method for treating a human subject with breast invasive ductal carcinoma (IDC) comprising: administering an agent that inhibits human ER+ and/or HER2+ expression or activity to a human subject that has IDC, wherein the agent comprises an oligonucleotide that functions via RNA interference, and wherein the oligonucleotide includes at least a miR-210 gene product.

In another aspect, there is provided herein a method for determining the likelihood of breast cancer progression, comprising: a) determining the expression level of hsa-miR-210 in a sample containing breast cancer cells from a subject with breast cancer, and b) comparing the expression level to a standard miRNA expression level in a control tissue, wherein higher expression of hsa-miR-210 in the subject with breast cancer correlates with a higher risk of progression.

In certain embodiments, the method further comprises wherein the control tissue comprises tissue from a representative individual or pool of individuals with breast cancer wherein the breast cancer has not progressed.

In certain embodiments, the method further comprises wherein the control tissue comprises tissue from the subject taken at an earlier point in time, as compared to the time of determining the expression level of step a).

In certain embodiments, the method further comprises wherein the standard miRNA expression level is from the representative pool of individuals and is a mean, median or other statistically manipulated or otherwise summarized or aggregated representative miRNA expression level for the miRNA level in the control tissues in the subject.

In certain embodiments, the method further comprises, wherein the expression level of ore or more of: let-7d and/or miR-221, is also measured relative to the expression level in the control tissue, and wherein an increased expression level of one or more of: let-7d and/or miR-221, correlates with a higher risk of progression.

In certain embodiments, the method further comprises wherein the expression level of one or more of: miR-10b, miR-126, miR-143, miR-218 and miR-335-5p, is also measured relative to the expression level in the control tissue, and wherein a decreased expression level of one or more of: miR-10b, miR-126, miR-143, miR-218 and miR-335-5p correlates with a higher risk of progression.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims

BRIEF DESCRIPTION OF THE FIGURES

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 9. (Table 1). The expression levels of 66 differentially expressed miRNAs in the comparison of ductal carcinoma in-situ (DCIS) to normal breast (false detection rate <0.05).

FIG. 10. (Table 2). The 6 miRNAs differentially expressed in IDC vs. DCIS. Only HER2+/EP− samples were considered in this comparison (false detection rate <0.05).

FIG. 11. (Table 3). The 9 miRNAs differentially expressed in invasive ductal carcinoma (IDS), when compared to ductal carcinoma in-situ (DCIS). All available IDC samples were included in the analysis, regardless of the subtype (false detection rate <0.05).

FIG. 12. (Table 4). The 10 miRNAs differentially expressed in ER+ IDC when compared to ER-IDC (false detection rate <0.05).

FIG. 13. (Table 5). miR-342 is the only miRNA differentially expressed in HER2+/ER-IDC when compared to all other IDC (false detection rate <0.05).

FIG. 14. (Table 6). The miRNAs differentially expressed in HER2+/ER-IDC were all down regulated when compared to the other IDC subtypes (false detection rate <0.05).

FIG. 15. (Table 7). The miRNAs differentially expressed in TNBC IDC when compared to the other IDC subtypes (false detection rate <0.05).

FIG. 16. (Table 8). The miRNAs differentially expressed in the molecular subtypes of IDC (false detection rate <0.05).

FIG. 17. (Table 9). miRNAs associated with time-to-metastasis in IDC.

FIG. 18. (Table 10). miRNAs associate with overall-survival in IDC.

FIG. 19. (Table 11). Functional analysis of genes inversely related to miR-210 in the normal/DCIS and DCIS/IDC transitions, performed using the DAVID database. Twenty-five genes from the Genetic association DB are linked to breast cancer (Enrichment p-value=1.4E-3). Breast cancer was the only disease associated to these genes.

FIG. 20. (Table 12). The TCGA cohort of patients with primary invasive ductal carcinoma.

FIG. 21. (Table 13). The prognostic values of RNA signatures in four BC cohorts.

FIG. 24A. The cross-validated Kaplan-Meier curves for IDC risk groups obtained from the TCGA cohort (n=466), using the prognostic 34-gene set. The permutation p value of the Log-Rank test statistic between risk groups was based on 1000 permutations (p<0.001). FIG. 24B. The ROC curve had an area under the curve (AUC) of 0.71 (p<0.001). The permutation p value was computed for testing the null hypothesis (AUC=0.5) using 1000 permutations.

FIG. 25A.

The cross-validated Kaplan-Meier curves for breast cancer risk groups obtained from the validation cohort (n=207), using the prognostic 34-gene set. The permutation p value of the Log-Rank test statistic between risk groups was based on 1000 permutations (p=0.001). FIG. 25B. The ROC curve had an AUC of 0.69 (p<0.001). The permutation p value was computed for testing the null hypothesis (AUC=0.5) using 1000 permutations.

FIG. 26. Table showing the negative correlation between mRNA expression and CpG DNA methylation of PIK3CA (FDR<0.001).

FIG. 27. Table showing DNA methylated CpG sites associated with Overall Survival in IDC (P-value <0.05).

FIG. 28. Table showing twenty four (24) mRNAs and ten (1) miRNAs were associated with clinical outcome and validated across independent IDC subclasses. The coding genes were restricted further by DNA methylation/OS analysis and presence of somatic mutations. Square brackets indicate the independent IDC subclasses used for validation. Marg Neg=Margin Negative. Horm Rec+ means ER+ and/or PR+ tumors. Mutation rate: Low <25 mutations in exome, 25<=Medium<=50, High>50. Mutations: PI3K (PIK3CA, AKT1, PTEN, PIK3R1), TP53 PIK3CA are double mutants. noMajorMut=others than PI3K, TP53, MAPK and GATA3.

FIG. 29. Table showing the integrated RNA linear risk predictor for outcome in the TCGA cohort (n=466).

DETAILED DESCRIPTION

Figure 1:
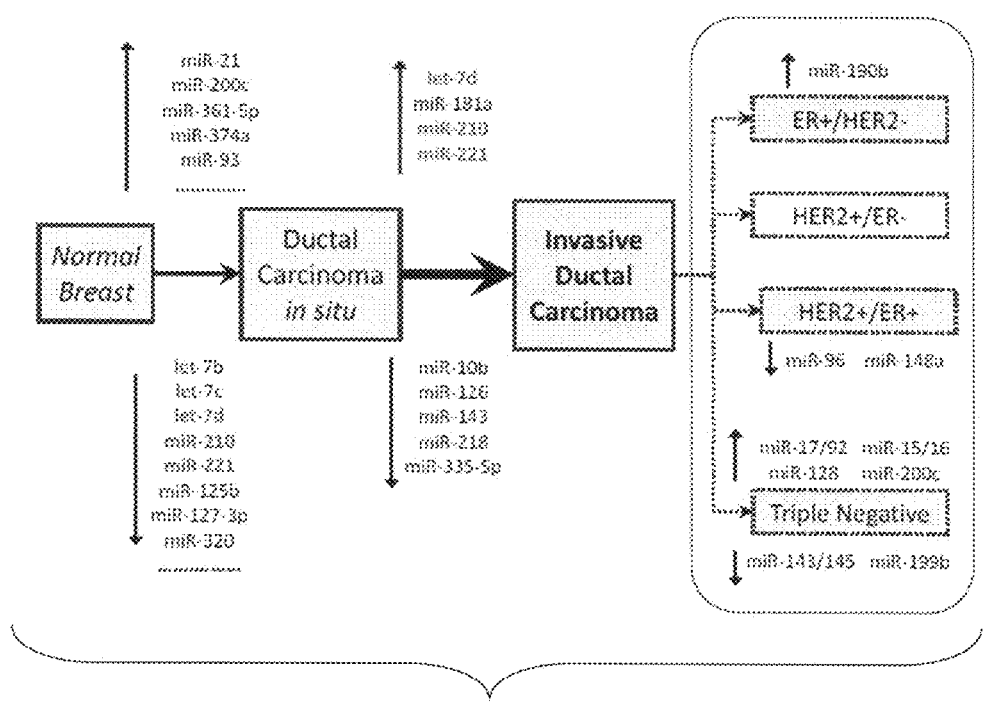
FIG. 1. The miRNAs deregulated in four IDC clinical subgroups (ER+/HER2−, HER2+/ER−, ER+/HER2+ and Triple negative), and in DCIS and normal breast. Breast cancer cell lines were (BT474, HCC38, MCF7, MDA-MB134, ZR-751). Average expression is shown for each miRNA in each class. Expression was mean centered for each miRNA.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions and General Discussion

As used herein interchangeably, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., E. coli RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

DNA Deoxyribonucleic acid
mRNA Messenger RNA
meDNA DNA methylation
miR microRNA
PCR Polymerase chain reaction
pre-miRNA Precursor microRNA
qRT-PCR Quantitative reverse transcriptase polymerase chain reaction
RNA Ribonucleic acid It is to be understood that the descriptions herein are exemplary and explanatory only and are not intended to limit the scope of the current teachings. In this application, the use of the singular includes the plural unless specifically stated otherwise.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient.

Detecting level of expression: For example, "detecting the level of miR or miRNA expression" refers to quantifying the amount of miR or miRNA present in a sample. Detecting expression of the specific miR, or any microRNA, can be achieved using any method known in the art or described herein, such as by qRT-PCR. Detecting expression of miR includes detecting expression of either a mature form of miRNA or a precursor form that is correlated with miRNA expression. Typically, miRNA detection methods involve sequence specific detection, such as by RT-PCR. miR-specific primers and probes can be designed using the precursor and mature miR nucleic acid sequences, which are known in the art.

DNA methylation is a biochemical process that involves the addition of a methyl group to the 5 position of the cytosine pyrimidine ring or the number 6 nitrogen of the adenine purine ring. DNA methylation stably alters the gene expression pattern in cells and is an important regulator of gene transcription. Aberrant DNA methylation patterns have been associated with a large number of human malignancies and found in two distinct forms: hypermethylation and hypomethylation compared to normal tissue. Hypermethylation typically occurs at CpG islands in the promoter region and is associated with gene inactivation. Global hypomethylation has also been implicated in the development and progression of cancer.

Messenger RNA (mRNA) is a large family of RNA molecules that convey genetic information from DNA to the ribosome, where they specify the amino acid sequence of the protein products of gene expression. Following transcription of mRNA by RNA polymerase, the mRNA is translated into a polymer of amino acids, a protein.

MicroRNA (miRNA): Single-stranded RNA molecules that regulate gene expression. MicroRNAs are generally about 22 nucleotides in length. MicroRNAs are processed from primary transcripts known as pri-miRNA to short stem-loop structures called precursor (pre)-miRNA and finally to functional, mature microRNA. Mature microRNA molecules are partially-complementary to one or more messenger RNA molecules, and their primary function is to down-regulate gene expression. MicroRNAs regulate gene expression through the RNAi pathway.

miR expression: As used herein, "low miR expression" and "high miR expression" are relative terms that refer to the level of miRNAs found in a sample. In some embodiments, low and high miR expression is determined by comparison of miRNA levels in a group of control samples and test samples. Low and high expression can then be assigned to each sample based on whether the expression of one or more miRs in a sample is above (high) or below (low) the average or median miR expression level. For individual samples, high or low miR expression can be determined by comparison of the sample to a control or reference sample known to have normal, high, or low expression, or by comparison to a standard value. Low and high miR expression can include expression of either the precursor or mature forms of miRNA, or both.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Poor prognosis: Generally refers to a decrease in survival, or in other words, an increase in risk of death or a decrease in the time until death. Poor prognosis can also refer to an increase in severity of the disease, such as an increase in spread (metastasis) of the cancer to other tissues and/or organs.

Screening: As used herein, "screening" refers to the process used to evaluate and identify candidate agents that affect such disease. Expression of a microRNA can be quantified using any one of a number of techniques known in the art and described herein, such as by microarray analysis or by qRT-PCR.

Small molecule: A molecule, typically with a molecular weight less than about 1000 Daltons, or in some embodiments, less than about 500 Daltons, wherein the molecule is capable of modulating, to some measurable extent, an activity of a target molecule.

Therapeutic: A generic term that includes both diagnosis and treatment.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

As used herein, a "candidate agent" or "test compound" is a compound selected for screening to determine if it can function as a therapeutic agent. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

Therapeutically-effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

In some embodiments of the present methods, use of a control is desirable. In that regard, the control may be a non-cancerous tissue sample obtained from the same patient, or a tissue sample obtained from a healthy subject, such as a healthy tissue donor. In another example, the control is a standard calculated from historical values. In one embodiment the control is a cancerous tissue sample of breast cancer. The control may be derived from tissue of known dysplasia, known cancer type, known mutation status, and/or known tumor stage. In one embodiment the control is a historical average derived from invasive ductal carcinoma. In another embodiment the control is a historical average derived from ductal carcinoma in situ. In one embodiment the control is from a tumor sample of the patient at an earlier point in time; this embodiment may be particularly useful when evaluating progression or remission of breast cancer.

Tumor samples and non-cancerous tissue samples can be obtained according to any method known in the art. For example, tumor and non-cancerous samples can be obtained from cancer patients that have undergone resection, or they can be obtained by extraction using a hypodermic needle, by microdissection, or by laser capture. Control (non-cancerous) samples can be obtained, for example, from a cadaveric donor or from a healthy donor.

An alteration (e.g., an increase or decrease) in the level of a miR gene product in the sample obtained from the subject, relative to the level of a corresponding miR gene product in a control sample, is indicative of the presence of a cancer-related disease in the subject.

In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a cell or tissue sample from a subject is greater than the amount of the same gene product in a control cell or tissue sample.

In another embodiment, the level of the at least one miR gene product in the test sample is less than the level of the corresponding miR gene product in the control sample (i.e., expression of the miR gene product is "down-regulated"). As used herein, expression of a miR gene is "down-regulated" when the amount of miR gene product produced from that gene in a cell or tissue sample from a subject is less than the amount produced from the same gene in a control cell or tissue sample.

The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

In some embodiments, screening comprises contacting the candidate agents/test compounds with cells. The cells can be primary cells obtained from a patient, or the cells can be immortalized or transformed cells.

The candidate agent/test compounds can be any type of agent, such as a protein, peptide, small molecule, antibody or nucleic acid. In some embodiments, the candidate agent is a cytokine. In some embodiments, the candidate agent is a small molecule. Screening includes both high-throughput screening and screening individual or small groups of candidate agents.

MicroRNA Detection

In some methods herein, it is desirable to identify miRNAs present in a sample.

The sequences of precursor microRNAs (pre-miRNAs) and mature miRNAs are publicly available, such as through the miRBase database, available online by the Sanger Institute (see Griffiths-Jones et al., Nucleic Acids Res. 36:D154-D158, 2008; Griffiths-Jones et al., Nucleic Acids Res. 34:D140-D144, 2006; and Griffiths-Jones, Nucleic Acids Res. 32:D109-D111, 2004). The sequences of the precursor and mature forms of the presently disclosed preferred family members are provided herein.

Detection and quantification of RNA expression can be achieved by any one of a number of methods well known in the art. Using the known sequences for RNA family members, specific probes and primers can be designed for use in the detection methods described below as appropriate.

In some cases, the RNA detection method requires isolation of nucleic acid from a sample, such as a cell or tissue sample. Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and small interfering RNAs (siRNAs).

In some embodiments, use of a microarray is desirable. A microarray is a microscopic, ordered array of nucleic acids, proteins, small molecules, cells or other substances that enables parallel analysis of complex biochemical samples. A DNA microarray has different nucleic acid probes, known as capture probes that are chemically attached to a solid substrate, which can be a microchip, a glass slide or a microsphere-sized bead. Microarrays can be used, for example, to measure the expression levels of large numbers of messenger RNAs (mRNAs) and/or miRNAs simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

Microarray analysis of miRNAs, for example (although these procedures can be used in modified form for any RNA analysis) can be accomplished according to any method known in the art. In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing the small RNA fraction (including the miRNA) extracted from a cell or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described above.

There are several types of microarrays than be employed, including spotted oligonucleotide microarrays, pre-fabricated oligonucleotide microarrays and spotted long oligonucleotide arrays. In spotted oligonucleotide microarrays, the capture probes are oligonucleotides complementary to miRNA sequences. This type of array is typically hybridized with amplified PCR products of size-selected small RNAs from two samples to be compared (such as non-cancerous tissue and cancerous or sample tissue) that are labeled with two different fluorophores. Alternatively, total RNA containing the small RNA fraction (including the miRNAs) is extracted from the two samples and used directly without size-selection of small RNAs, and 3' end labeled using T4 RNA ligase and short RNA linkers labeled with two different fluorophores. The samples can be mixed and hybridized to one single microarray that is then scanned, allowing the visualization of up-regulated and down-regulated miRNA genes in one assay.

In pre-fabricated oligonucleotide microarrays or single-channel microarrays, the probes are designed to match the sequences of known or predicted miRNAs. There are commercially available designs that cover complete genomes (for example, from Affymetrix or Agilent). These microarrays give estimations of the absolute value of gene expression and therefore the comparison of two conditions requires the use of two separate microarrays.

Spotted long oligonucleotide arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing.

In some embodiments, use of quantitative RT-PCR is desirable. Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miR, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, three of which are described below.

Methods for quantitative polymerase chain reaction include, but are not limited to, via agarose gel electrophoresis, the use of SYBR Green (a double stranded DNA dye), and the use of a fluorescent reporter probe. The latter two can be analyzed in real-time.

With agarose gel electrophoresis, the unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown.

The use of SYBR Green dye is more accurate than the agarose gel method, and can give results in real time. A DNA binding dye binds all newly synthesized double stranded DNA and an increase in fluorescence intensity is measured, thus allowing initial concentrations to be determined. However, SYBR Green will label all double-stranded DNA, including any unexpected PCR products as well as primer dimers, leading to potential complications and artifacts. The reaction is prepared as usual, with the addition of fluorescent double-stranded DNA dye. The reaction is run, and the levels of fluorescence are monitored (the dye only fluoresces when bound to the double-stranded DNA). With reference to a standard sample or a standard curve, the double-stranded DNA concentration in the PCR can be determined.

The fluorescent reporter probe method uses a sequence-specific nucleic acid based probe so as to only quantify the probe sequence and not all double stranded DNA. It is commonly carried out with DNA based probes with a fluorescent reporter and a quencher held in adjacent positions (so-called dual-labeled probes). The close proximity of the reporter to the quencher prevents its fluorescence; it is only on the breakdown of the probe that the fluorescence is detected. This process depends on the 5' to 3' exonuclease activity of the polymerase involved.

The real-time quantitative PCR reaction is prepared with the addition of the dual-labeled probe. On denaturation of the double-stranded DNA template, the probe is able to bind to its complementary sequence in the region of interest of the template DNA. When the PCR reaction mixture is heated to activate the polymerase, the polymerase starts synthesizing the complementary strand to the primed single stranded template DNA. As the polymerization continues, it reaches the probe bound to its complementary sequence, which is then hydrolyzed due to the 5'-3' exonuclease activity of the polymerase, thereby separating the fluorescent reporter and the quencher molecules. This results in an increase in fluorescence, which is detected. During thermal cycling of the real-time PCR reaction, the increase in fluorescence, as released from the hydrolyzed dual-labeled probe in each PCR cycle is monitored, which allows accurate determination of the final, and so initial, quantities of DNA.

In some embodiments, use of in situ hybridization is desirable. In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is sufficiently small, in the entire tissue (whole mount ISH). RNA ISH can be used to assay expression patterns in a tissue, such as the expression of miRNAs.

Sample cells or tissues are treated to increase their permeability to allow a probe, such as a miRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous or cancerous tissue sample. Since the sequences of particular miRs are known, miR-specific probes can be designed accordingly such that the probes specifically bind particular miR-gene products. Probes specific to mRNA can also be utilized.

For detection of RNA, an intracellular reverse transcription step may be used to generate complementary DNA from RNA templates prior to in situ PCR. This enables detection of low copy RNA sequences.

Detection of intracellular PCR products is generally achieved by techniques, such as indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

General Discussion

Estrogen-receptor (ER)-positive and ER-negative breast cancers are distinct diseases in molecular terms. Two key molecular signatures: PR and human epidermal growth factor receptor type 2 (HER2) are now believed to be fundamental in delineation of classification and treatments. "Triple-negative" breast cancers (TNBC), lacking ER, progesterone receptor (PR), and HER2 expression, are aggressive malignancies not responsive to current targeted therapies. Ductal carcinoma in situ (DCIS) is a heterogeneous group of lesions reflecting the proliferation of malignant cells within the breast ducts without invasion through the basement membrane. About 80% of all breast cancers are invasive ductal carcinomas (IDC), the most frequent type of BC. Breast tumors of distinct molecular subtypes (luminal A/B, HER2+, and basal-like) have dramatically different mRNA profiles. One hypothesis of breast tumorigenesis assumes a gradual transition from epithelial hyperproliferation to DCIS, and then to invasive carcinoma (IDC). This progression model is strongly supported by clinical and epidemiological data and by molecular clonality studies. Until 1980, DCIS was diagnosed rarely and represented <1% of BC. With the increased use of mammography, DCIS became the most rapidly increasing subset of BC, accounting for 15%-25% of newly diagnosed BC cases in the US.

A dramatic change occurs during the normal-to-DCIS transition, but surprisingly, in situ and invasive breast carcinomas of the same histological subtype generally share the same genetic and epigenetic alterations and expression patterns.

In contrast, the mRNA profiles of breast tumors of distinct subtypes (luminal, HER2+, and basal-like) are dramatically different. The expression and mutation status of numerous tumor suppressor and oncogenes have been analyzed in DCIS and IDC, including TP53, PTEN, PIK3CA, ERBB2, MYC, and differences have been found according to the tumor subtype but not histological stage. For example, mutations in TP53 are more frequent in basal-like and HER2+ subtypes compared with luminal tumors; in basal-like cases, PIK3CA is rarely mutated but PTEN is frequently lost, and amplification of ERBB2 is specific for the HER2+ subtype. The expression of several candidate genes selected based on their biological function has also been analyzed in DCIS.

Shown herein is that a microRNA profile established for the normal breast to ductal carcinoma in situ transition is largely maintained in the in situ to invasive ductal carcinoma transition.

In addition, it is shown that a 9-microRNA signature may be used to differentiate invasive from in situ carcinoma. Specifically, let-7d, miR-210 and −221 were shown to be downregulated in in situ and up-regulated in the invasive transition, thus featuring an expression reversal along the cancer progression path.

Also described is a microRNA signature for overall-survival and time-to-metastasis. Five non-coding genes were associated with both prognostic signatures: miR-210, miR-21, miR-106b*, miR-197 and let-7i; with miR-210 the only one also involved in the invasive transition. To pinpoint critical cellular functions affected in the invasive transition, identification was made of the protein coding genes with inversely related profiles to miR-210: BRCA1, FANCD, FANCF, PARP1, E-cadherin, Rb1, which were all activated in in situ and down-regulated in invasive carcinoma.

Additionally, described herein are differential splicing isoforms with special features, such as a truncated EGFR lacking the kinase domain and over-expressed only in ductal carcinoma in situ.

MicroRNA data from deep sequencing was investigated in order to discover highly informative miRNA profiles for breast cancer, which included normal breast, in situ and invasive ductal carcinomas. Embodiments of the invention, as described herein, extends substantially the knowledge and methods of applying miRNA in BC progression, performing diagnosis, predicting progression, estimating survival time, and predicting metastasis.

Described herein is the role of miR-210 and other key miRNAs involved in the normal breast/DCIS and DCIS/IDC transitions.

Also described herein are differentially regulated microRNAs in histological and molecular BC types. This is especially useful and has particular clinical relevance because it now identifies microRNA associated with time-to-metastasis and overall-survival. All non-coding genes that were identified in the prognostic signatures were associated with poor outcome, with the exception of miR-21. The expression of miR-21, highly increased in DCIS, was maintained or even lowered in IDC.

As noted in the Examples herein, in the trimmed dataset, miR-423-3p was still significant, by multivariate Cox regression and by univariate analysis, in overall-survival. The number of miRNAs associated with prognosis was extended, and miR-210 was confirmed.

In the Examples herein, miR-126 and −335 were among the 5 miRNAs down-regulated in the DCIS/IDC transition. Nevertheless, they were not associated with time-to-metastasis or overall-survival. Another miRNA down-regulated in the DCIS/IDC transition was miR-10b; however, there was no association of miR-10b to metastasis.

Figure 5:
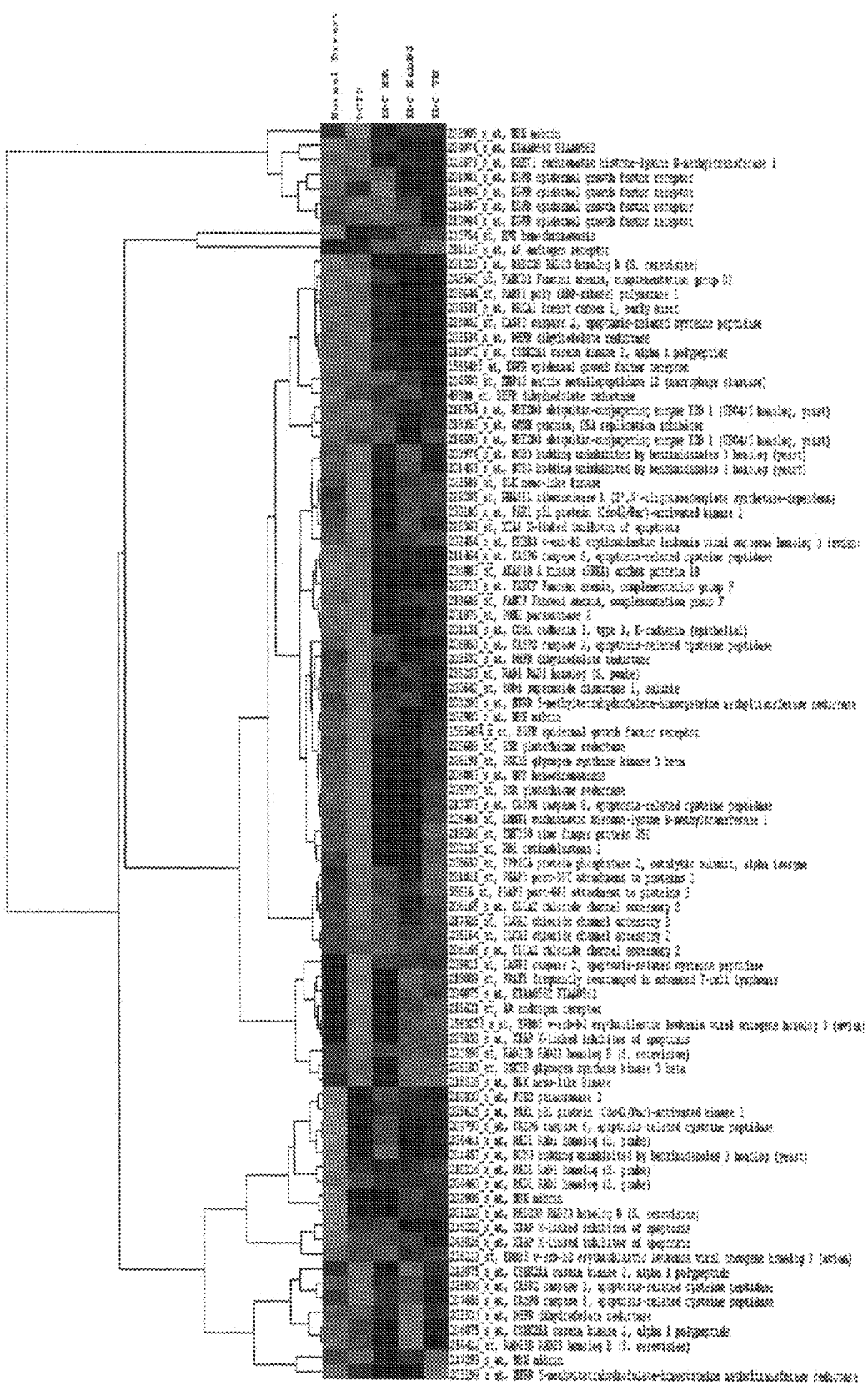
FIG. 5. The genes associated with breast cancer pathways and inversely related to miR-210. Breast cancer was the only significant disease identified (25 genes; Enrichment p<0.001). Breast cancer genes regulated in an antagonistic fashion to miR-210, along the DCIS/IDC progression axis, included RB1, BRCA1, FANCD, FANCF, PP2CA, PARP1, NLK, CDH1 and EHMT1. Pathways inversely related to miR-210 in BC were: caspase cascade in apoptosis, HER2 receptor recycling, TNFR1 signaling, FAS signaling (CD95) and BRCA1, BRCA2 and ATR in cancer susceptibility. Some of the genes in the pathways had differential regulation of their splicing isoforms. For example, EGFR classical isoforms were expressed in normal breast and down regulated in DCIS. A shorter EGFR variant (uc003tqi.2), lacking the tyrosine kinase domain, was specifically over-expressed in DCIS.
Figure 6:
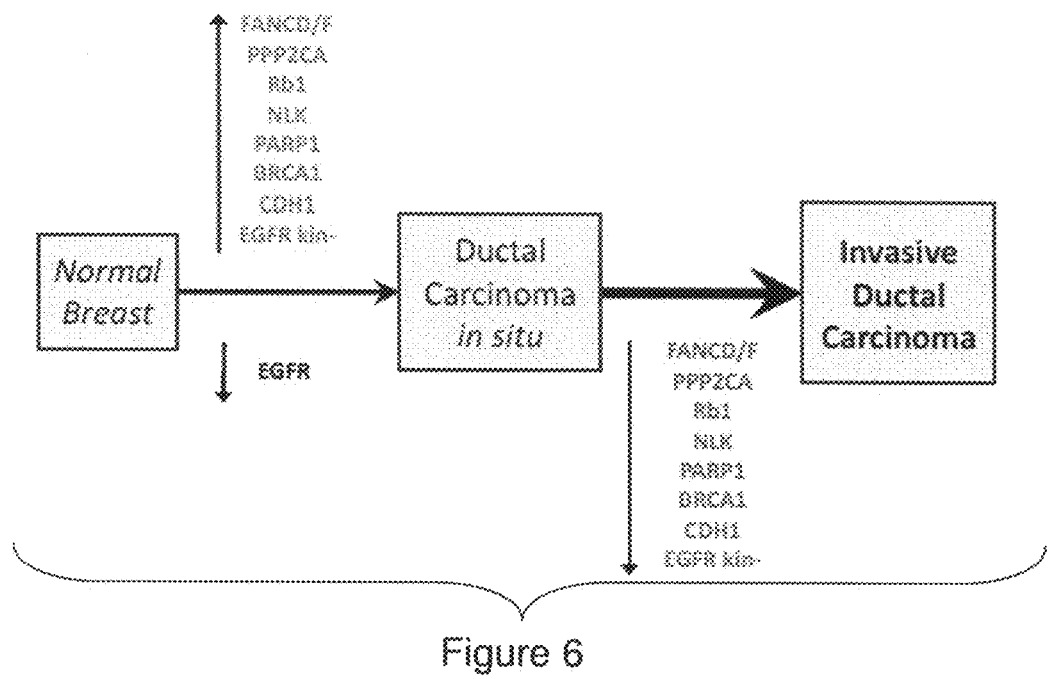
FIG. 6. Certain breast cancer genes were inversely related to miR-210 and displayed expression reversal along the breast cancer progression path.

Using the invasive microRNA signature described herein, further analysis was performed to identify genes and functions associated to BC progression. Among the 9 miRNAs in the invasiveness signature, miR-210 was the only one associated to prognosis and showing expression reversal. Thus, the inventors then determined the protein-coding genes that behaved antagonistically to miR-210 during BC progression. For these genes, the inventors identified the deregulated pathways, which in turn, corresponded to a small group of key breast cancer genes. These genes, activated in DCIS, and down-regulated in IDC, included BRCA1, RB1, FANCD, FANCF, PP2CA, EGFR, PARP1, NLK, CDH1 and EHMT1 (FIG. 5 and FIG. 6).

Thus, in one broad aspect, there is described herein a 9 miRNA micro-signature specific for invasiveness and 5 miRNAs associated to time-to-metastasis and overall-survival in IDC patients.

In a particular aspect, there is described herein the discovery that miR-210 is regulated during BC progression, and is also a component of the two prognostic signatures.

In another particular aspect, there is described herein a set of highly prominent BC genes expressed in a miR-210 antagonistic fashion.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

The value of the present invention can thus be seen by reference to the Examples herein.

EXAMPLES

Example 1

Materials and Methods

Figure 7:
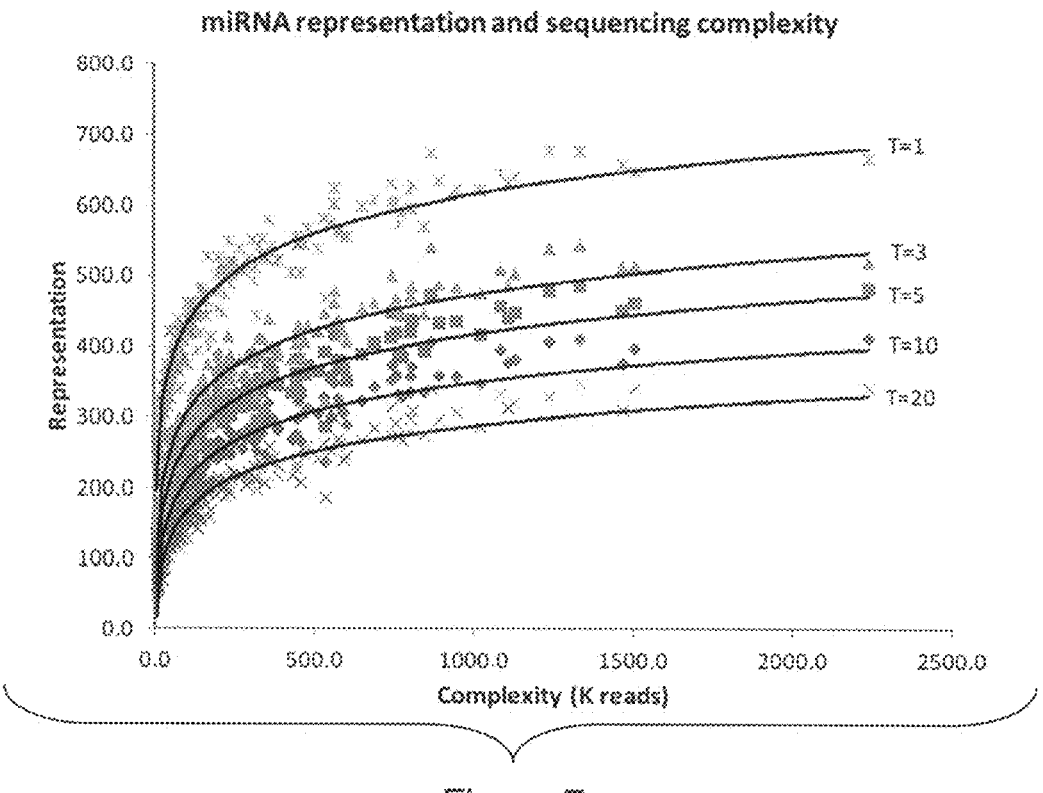
FIG. 7. Determination of Complexity$_{50}$, i.e., the minimal complexity that can be used to generate representative miRNA profiles from sequencing runs. Complexity$_{50}$ corresponds to the complexity of run, which has Representation$_{50}$ number of miRNAs species. Representation is defined as the number of different mRNA species that are present at, or above, a certain count threshold. Representation$_{50}$ is half of Representation$_{Max}$, the maximum number of miRNAs species identified in a single run of a dataset. Complexity is the total number of miRNA reads in a run (or sequenced sample). The scatter plots indicate the maximal Representation among the runs, at increasing complexity within the dataset. Different counts thresholds were used to define the presence of miRNA species: purple cross>=20 reads, blue>=10 reads, red square>=5 reads, green triangle>=3, cyan asterisk>=1. The complexity (X axis) is in thousands of reads (K reads).
Figure 8:
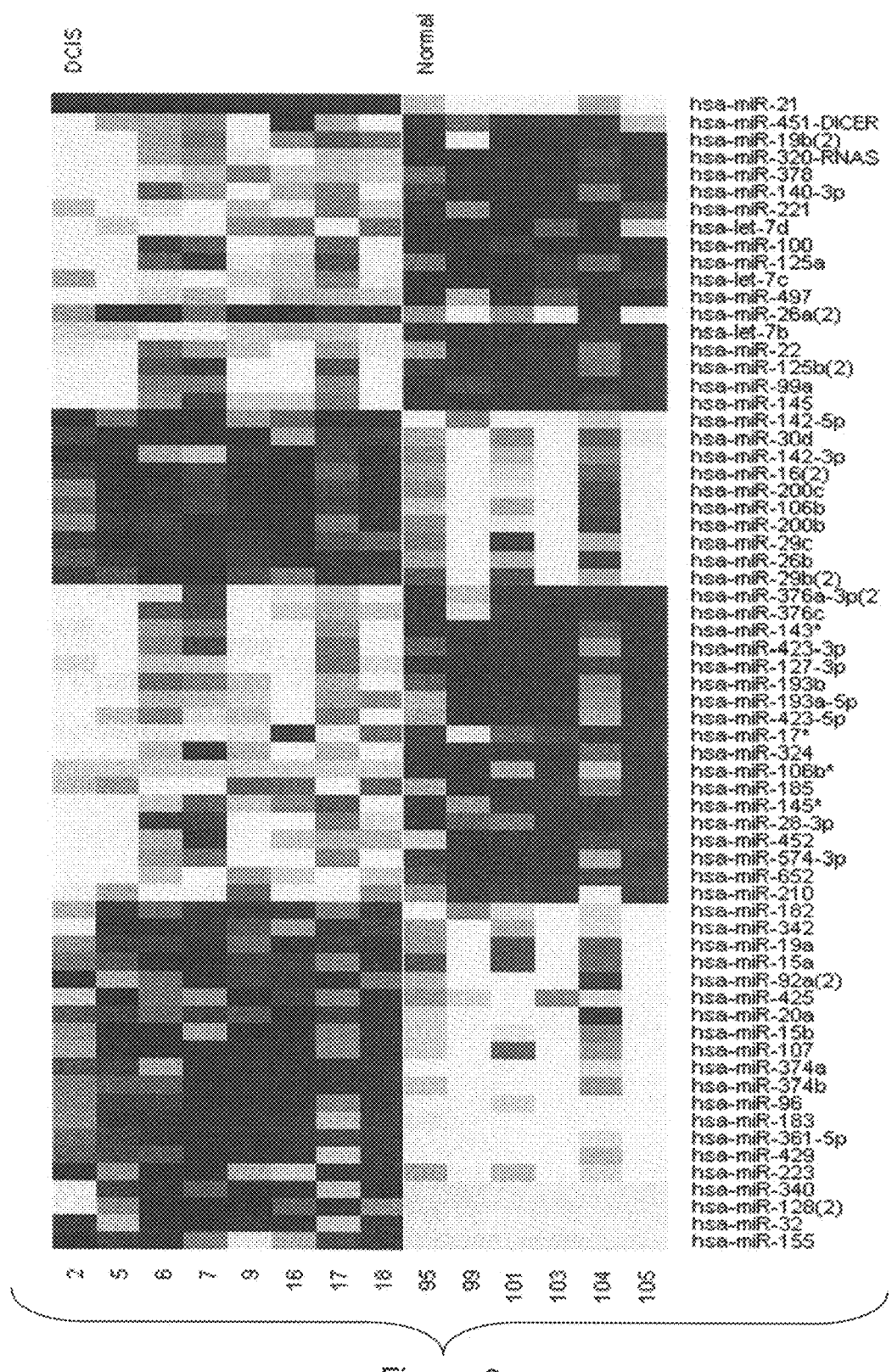
FIG. 8. Clustering tree of DCIS vs. Normal Breast Samples.

The minimal run complexity of 98,000 reads for optimal representation of breast miRNA profiles were determined, by using Complexity$_{50}$. The Complexity$_{50}$ as the median complexity of the nearest-neighbors centered on Representation$_{50}$ was computed (FIG. 7). Thus, included in this study were only those runs that had complexity larger than Complexity$_{50}$ (107 samples were retained out of 185). The normalization of the different runs was performed using a modification of RPKM (Mortazavi A, Williams B A, McCue K, Schaeffer L, & Wold B (2008) Mapping and quantifying mammalian transcriptomes by RNA-Seq. *Nat. Methods* 5(7):621-628). The raw data for some short RNA sequences were obtained from Farazi et al. (2011) MicroRNA Sequence and Expression Analysis in Breast Tumors by Deep Sequencing," Cancer Res. 71(13):4443-4453.

Since the lengths of the different miRNA species are almost constant, the miRNA length were not included in the normalization, which thus was simply computed as reads per million (RPM). The expression data was threshold at 200 RPM and excluded miRNAs for which less than 20% of expression values had less than 1.5 fold change in either direction from the miRNA median value. The final expression matrix contained measures for 159 miRNAs in 107 samples. The two-sample T-test was used for 2-class comparisons (i.e., IDC vs. DCIS). A multivariate permutations test was computed based on 1000 random permutations. The false detection rate was used to assess the multiple testing errors. The confidence level of false discovery rate assessment was of 80% and the maximum allowed proportion of false positive genes was of 5%. The inventor discovered which miRNA whose expression was significantly related to time-to-metastasis and overall-survival, by using Cox proportional hazards models. Permutation tests were performed in which the times and censoring indicators were randomly permuted among samples. Permutation p-values for significant genes were computed based on 10000 random permutations. Hazard ratios were computed for a two-fold change in the miRNA expression level. For each significant miRNA based upon the Cox regression, Kaplan-Meier survival curves were plotted, where the patients were split into two groups at the median expression and the difference between the curves was assessed with the log-rank test. Whole transcriptome profiles for human normal breast, DCIS and IDC were derived from Affymetrix human genome U133 Plus 2.0 arrays. Forty two normal breast, 17 DCIS, 51 ER+/HER2− IDC, 17 HER2+/ER−IDC, 17 HER2+/ER+ IDC and 33 Triple negative IDC samples (25, 29). CEL files or RMA data were obtained from GEO database (GSE3893, GSE2109, GSE21422 and GSE21444). RMA was used alongside quantiles normalization. Database for Annotation, Visualization and Integrated Discovery Expression Analysis Systematic Explorer (DAVID EASE) was used for gene ontology, disease association and Biocarta pathways analysis.

miRNAs Define the In Situ to Invasive Ductal Carcinoma Transition

The miRNA profiles for invasive ductal carcinoma (IDC), ductal carcinoma in situ (DCIS) and normal breast were discovered. Using an unbiased approach to the complexity selection of sequencing runs, robust and highly informative miRNA profiles for breast cancer were obtained.

Described herein is a procedure to determine the minimum number of reads necessary to yield miRNA profiles representative of the human repertoire (FIG. 7). For this BC dataset the minimal required complexity was of 98,000 reads. Applying this threshold, 78 low complexity breast cancer runs were excluded (43%) and 107 (57%) where retained for further statistical analysis. Using this trimmed dataset, an expression matrix representative of high, medium and low abundance miRNA species was generated. Sixty-six miRNAs were differentially regulated in DCIS in comparison to normal breast (FIG. 9-*Table* 1 and FIG. 1).

To identify the miRNAs specifically altered in tumor invasion, the DCIS and IDC samples were compared. Nine miRNAs were differentially modulated in the DCIS to IDC transition (FIG. 10—Table 2 and FIG. 11—Table 3). This differential modulation is generally referred to herein as the "invasiveness micro-signature" where: miR-210, let-7d, miR-181a and miR-221 were activated, while miR-10b, miR-126, miR-218, miR-335-5p and miR-143 were repressed (FIG. 1).

Among these 9 miRNAs, let-7d, miR-210 and miR-221 were those with the most extreme changes in expression, being first down regulated in DCIS, relative to normal, and then up-regulated in IDC. None of the miRNAs involved in the DCIS/IDC transition was involved, with a similar trend, in the early normal/DCIS transition. No miRNA correlated with tumor grade.

Expression was analyzed and differentially expressed miRNA was identified in the IDC subtypes, as shown in FIG. 12—Table 4, FIG. 13—Table 5, FIG. 14—Table 6 and FIG. 15—Table 7). Examples are: miR-190 was over-expressed in ER+/HER2− IDC; Triple negative IDC was characterized by activation of the Myc-regulated miR17/92 oncomir cluster, miR-200c and miR-128; miR-200c was among the most repressed miRNAs in ER+/HER2+ double positive BC, together with miR-148a and miR-96.

Figure 2:
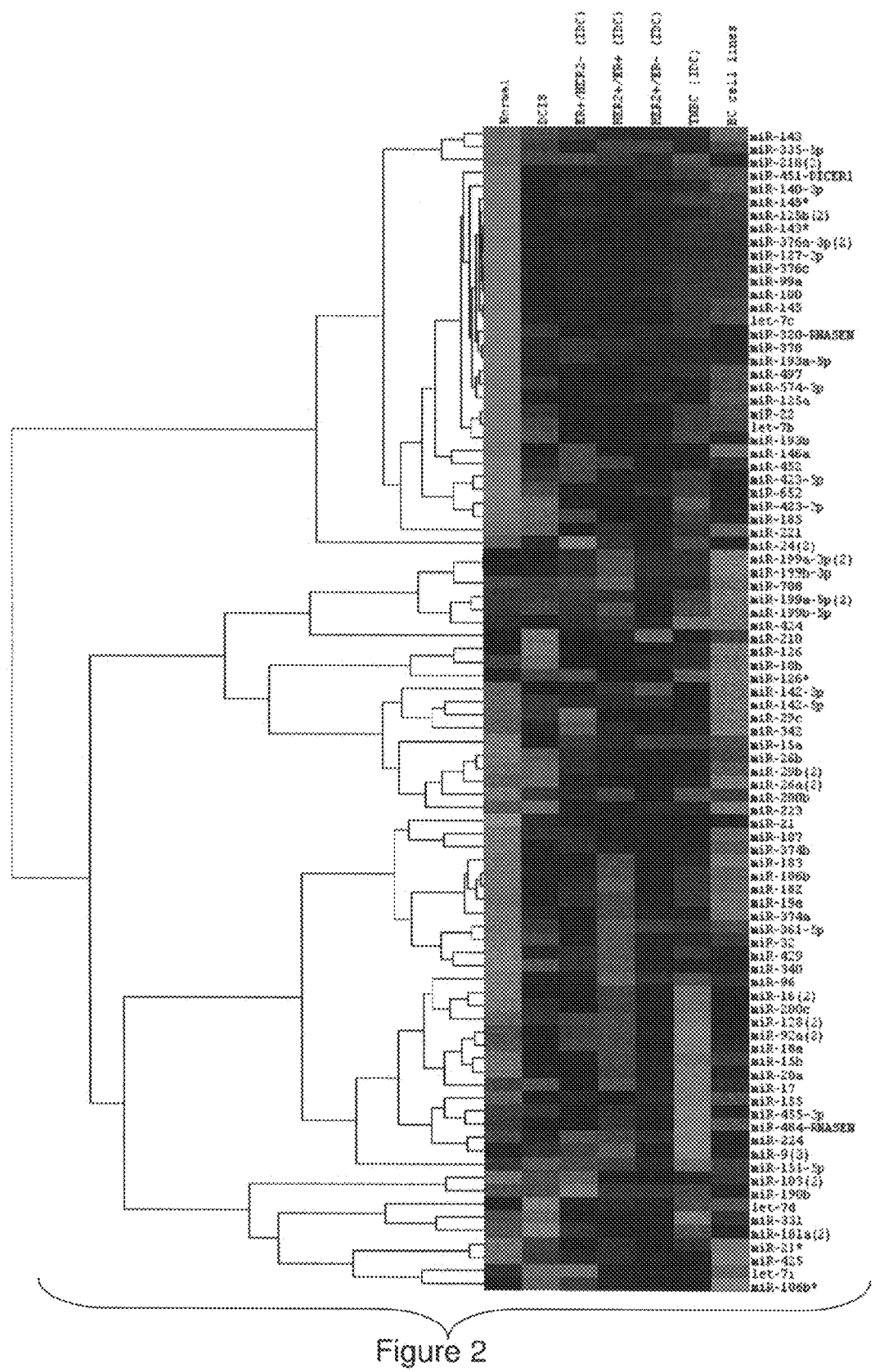
FIG. 2. The three miRNAs with bold typeface were those with expression reversal, as indicated by the colors (red, up-regulation; green, down-regulation). Sixty-six miRNAs were deregulated in the first transition, Normal breast to DCIS (only the most significant miRNAs are listed). Nine miRNAs were deregulated in the invasion transition, DCIS to IDC, and are listed. This second signature is identified as the invasiveness micro-signature. None of the miRNAs involved in the invasion transition was differentially regulated, with the same trend, in the first carcinoma transition.

The deregulated miRNAs in four IDC clinical subgroups (ER+/HER2−, HER2+/ER−, ER+/HER2+ and Triple Negative) are shown in FIG. 2, along with those prominent in DCIS and normal breast. Breast cancer cell lines were included in the analysis. The examined the miRNA profiles of the BC molecular subtypes were also examined. Luminal B and Basal were the subtypes best characterized by miRNAs. miR-190 and miR-425 were associated with Luminal B. miR-452, miR-224, miR-155, miR-9 and the miR-17/92 cluster were associated with the Basal (FIG. 16—Table 8).

The miRNAs present in the tumors, but not in normal breast, and not in the BC cell lines, were likely the results of contaminating cell types; miR-142 and miR-223 were two such miRNAs (FIG. 2). It is noted that miR-142 and miR-223 are both highly specific for the hemopoietic system, like miR-342, another miRNA in the same expression cluster (FIG. 2). Other hemopoietic miRNAs in this non-breast gene cluster included miR-29 and miR-26.

Example 2

Prognostic miRNA Signature for Time-to-Metastasis and Overall-Survival in Breast Carcinoma The association between miRNAs and prognosis were discovered using two clinical parameters: time-to-metastasis and overall-survival. The differentially expressed miRNAs in the Normal/DCIS, DCIS/IDC transitions and the different IDC subtypes (FIG. 2) were identified.

miR-127-3p, miR-210, miR-185, miR-143* and let-7b were among the miRNAs significantly associated with time-to-metastasis, as determined by univariate and multivariate analysis (FIG. 17—Table 9).

miR-210, miR-21, miR-221 and miR-652 were among those correlated with overall-survival (FIG. 18—Table 10), with miR-210, miR-21, miR-106b*, miR-197 and let-7i common to both prognostic signatures. Among these five common miRNAs, miR-210 was the only one present in the invasiveness micro-signature.

Figure 3A:
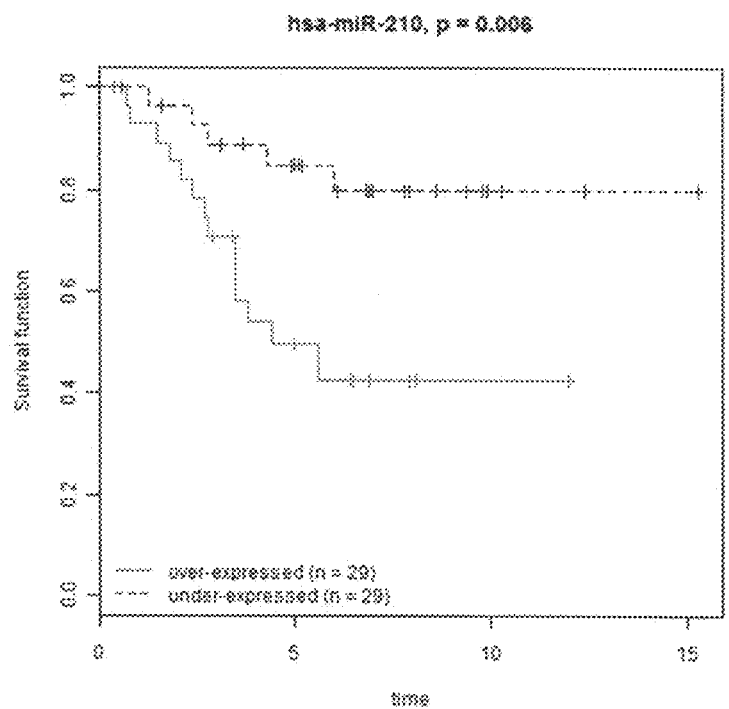
FIG. 3A-3B. The Kaplan Meier curves for miR-210 in time-to-metastasis (FIG. 3B) and overall-survival (FIG. 3A) of patients with invasive ductal carcinoma. This data shows that miR-210 was the only miRNA associated to prognosis and present in the invasiveness micro-signature.
Figure 3B:
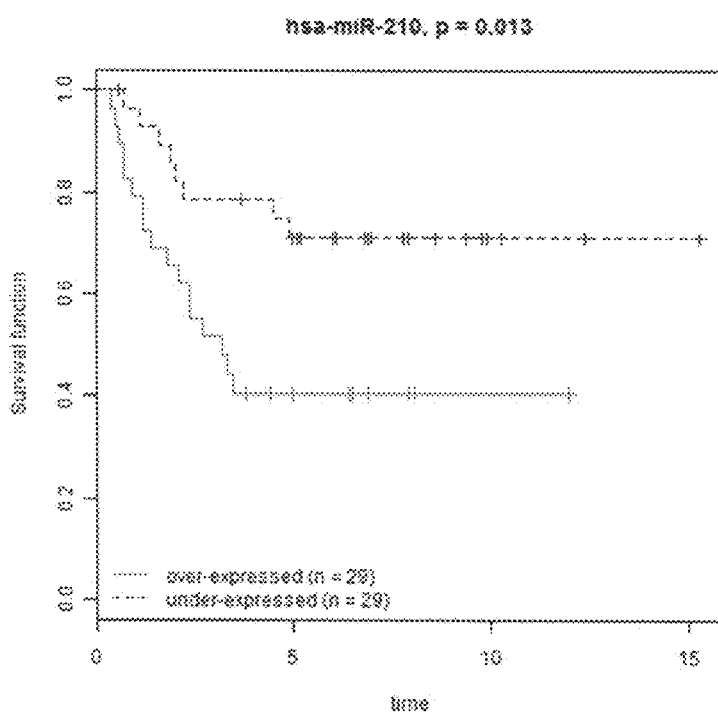

The Kaplan Meier curves for miR-210 in time-to-metastasis is shown in FIG. 3B, and overall-survival of IDC patients is shown in FIG. 3A.

Figure 3C:
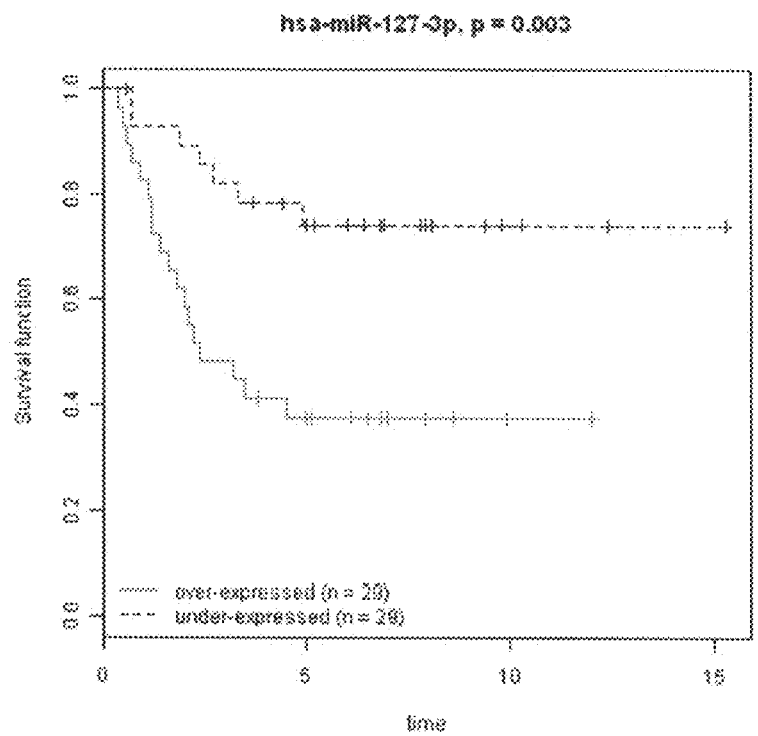
FIGS. 3C-3K. The Kaplan Meier curves for the other miRNAs in the prognostic signatures of IDC for time-to-metastasis (log rank, p<0.05).
Figure 3D:
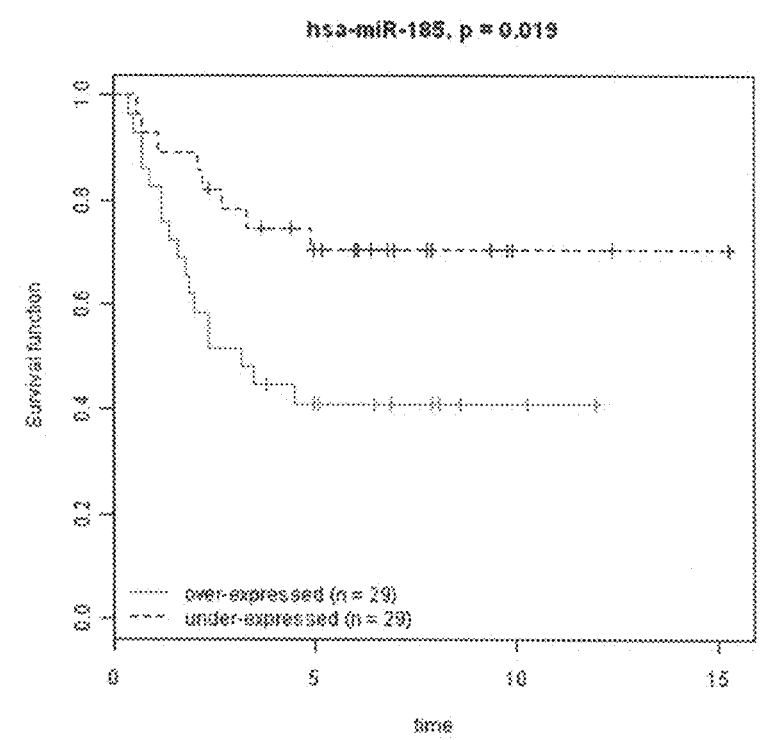
Figure 3E:
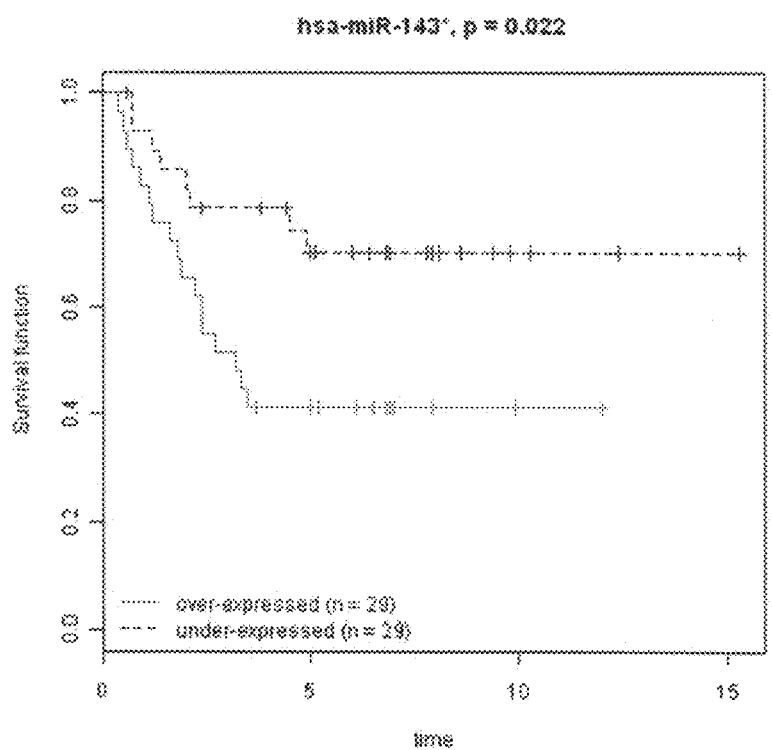
Figure 3F:
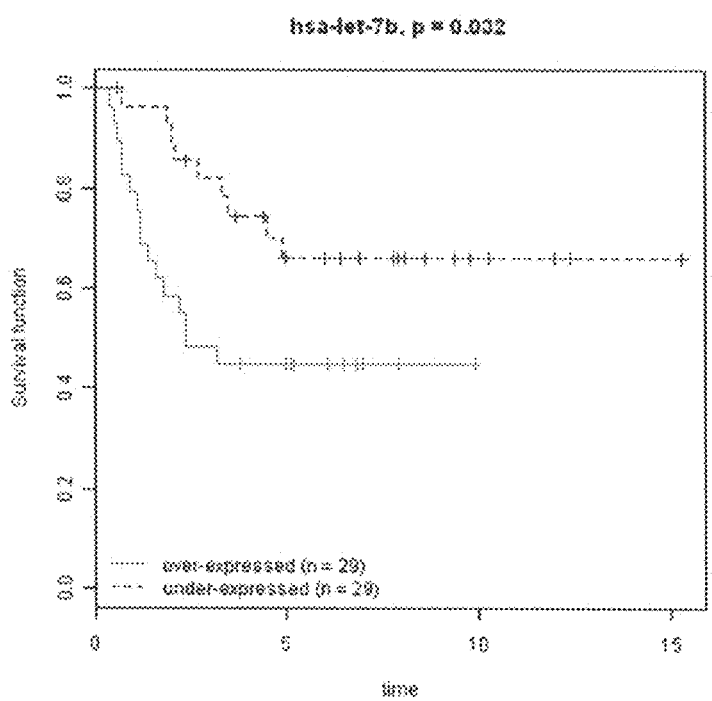
Figure 3G:
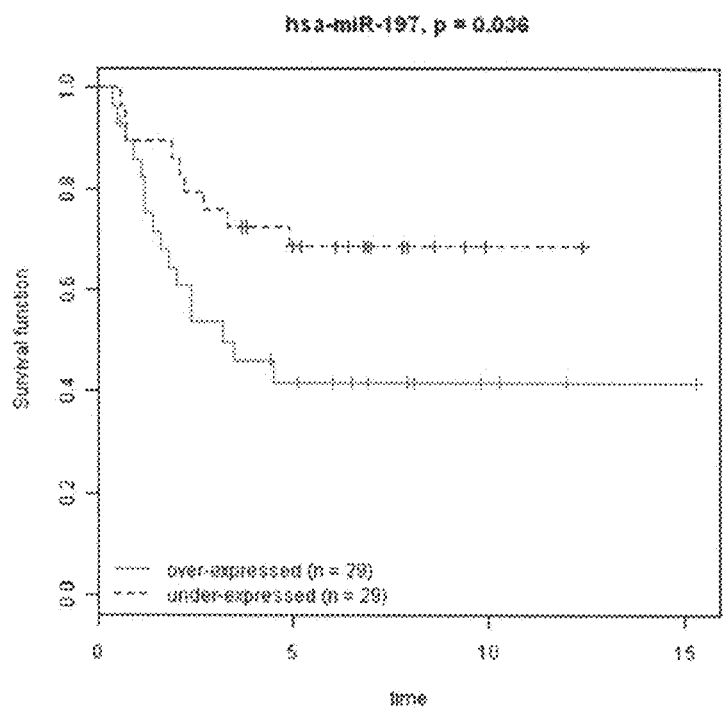
Figure 3H:
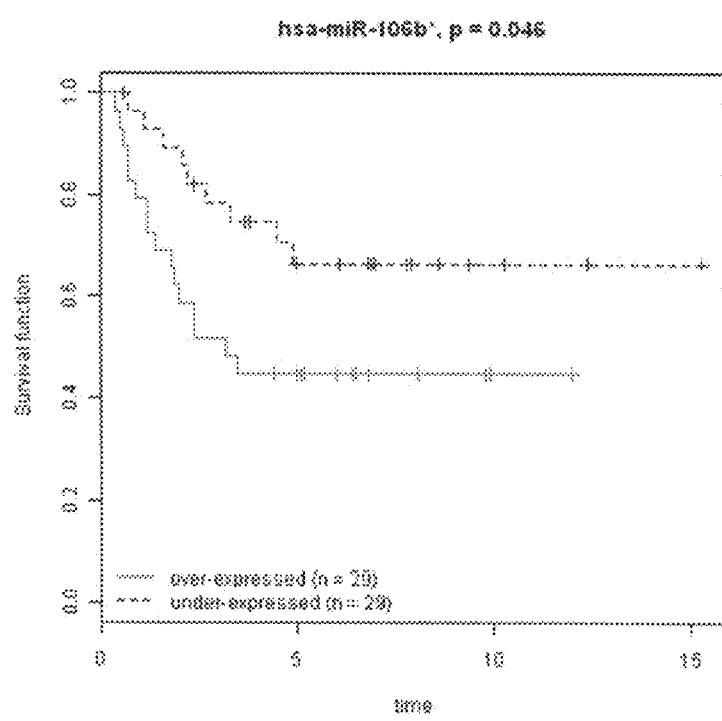
Figure 3I:
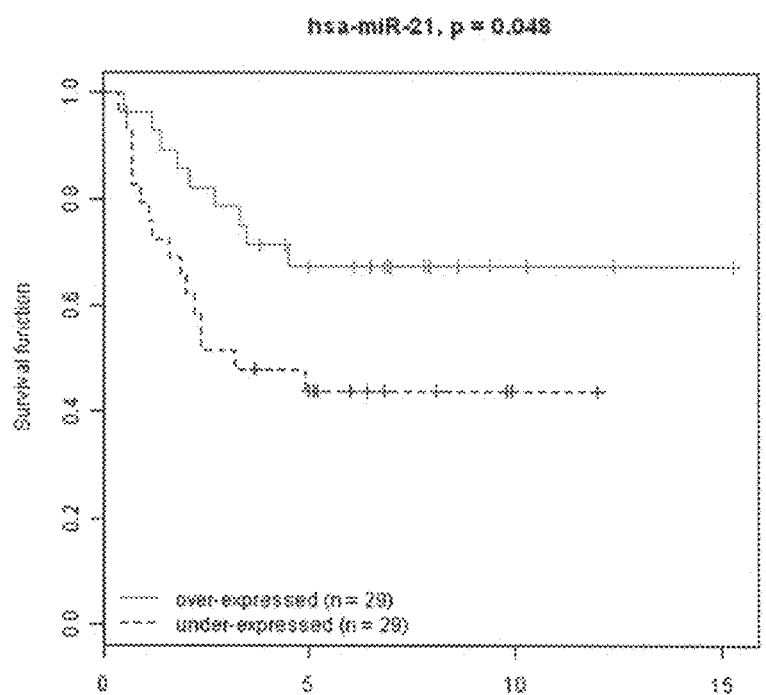
Figure 3J:
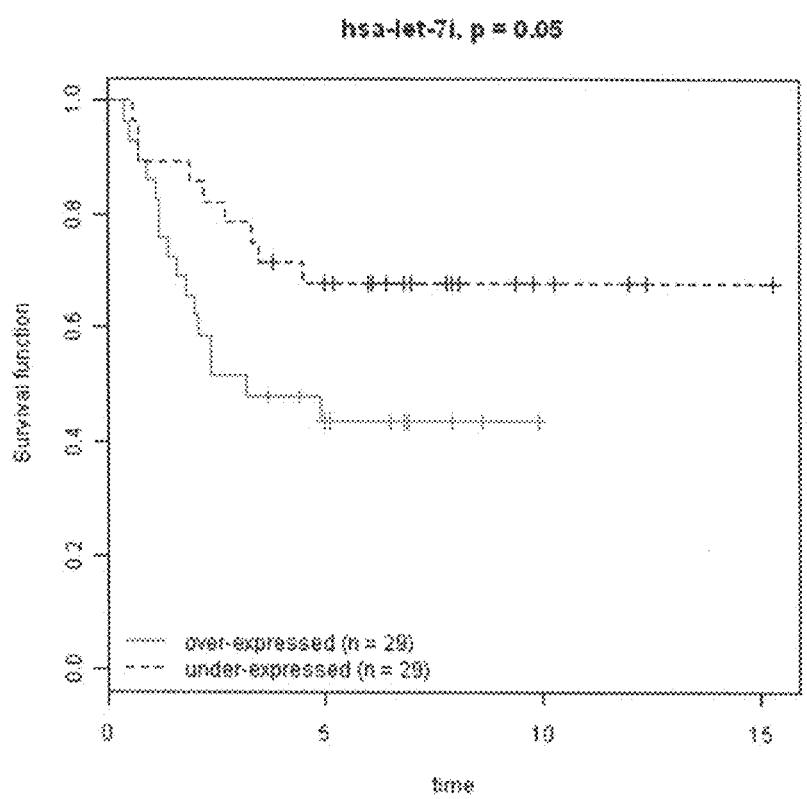

The Kaplan Meier curves for the miRNAs associated with time-to-metastasis in IDC are shown in FIGS. 3C-3J, where FIG. 3C shows miR-127; FIG. 3D shows miR-185; FIG. 3E shows miR-145*; FIG. 3F shows let-7b; FIG. 3G shows miR-197; FIG. 3H shows miR-106*; FIG. 3I shows miR-21; and, FIG. 3J shows let-7i.

Figure 3K:
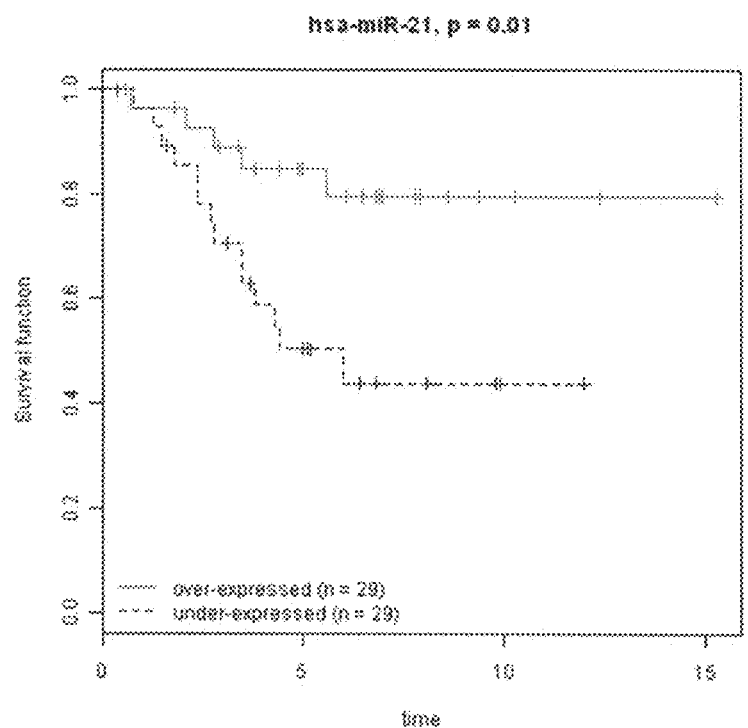
Figure 3L:
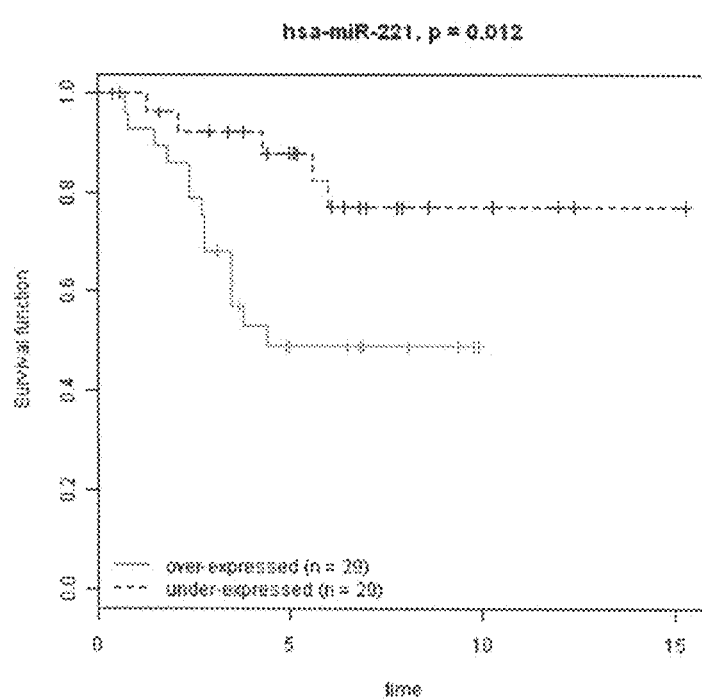
FIGS. 3L-3S. The Kaplan Meier curves for the other miRNAs in the prognostic signatures of IDC for overall-survival (log rank, p<0.05).
Figure 3M:
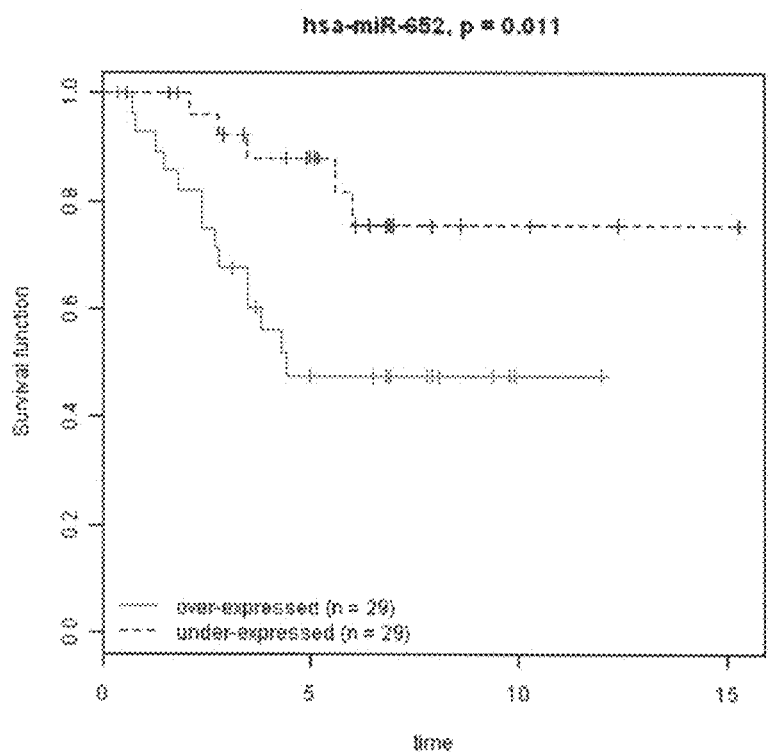
Figure 3N:
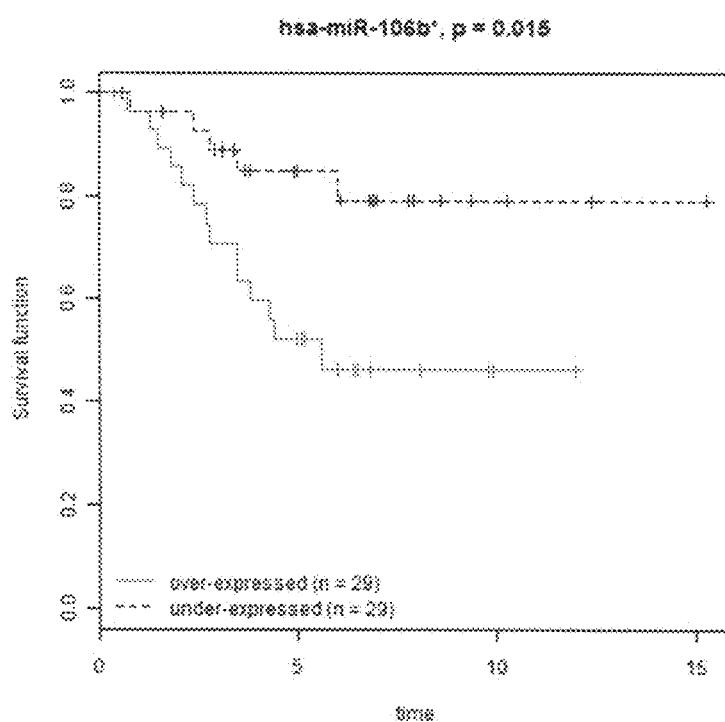
Figure 3O:
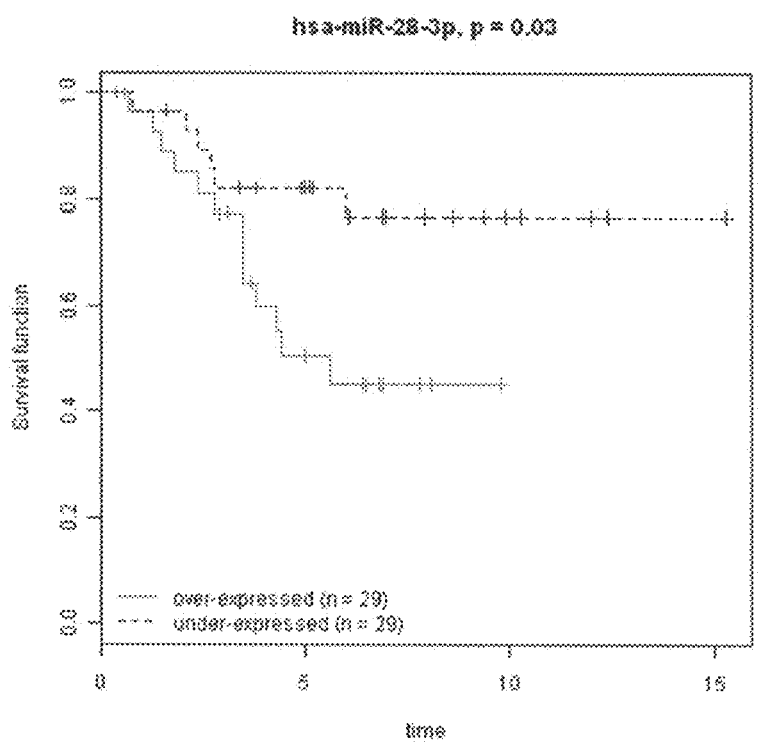
Figure 3P:
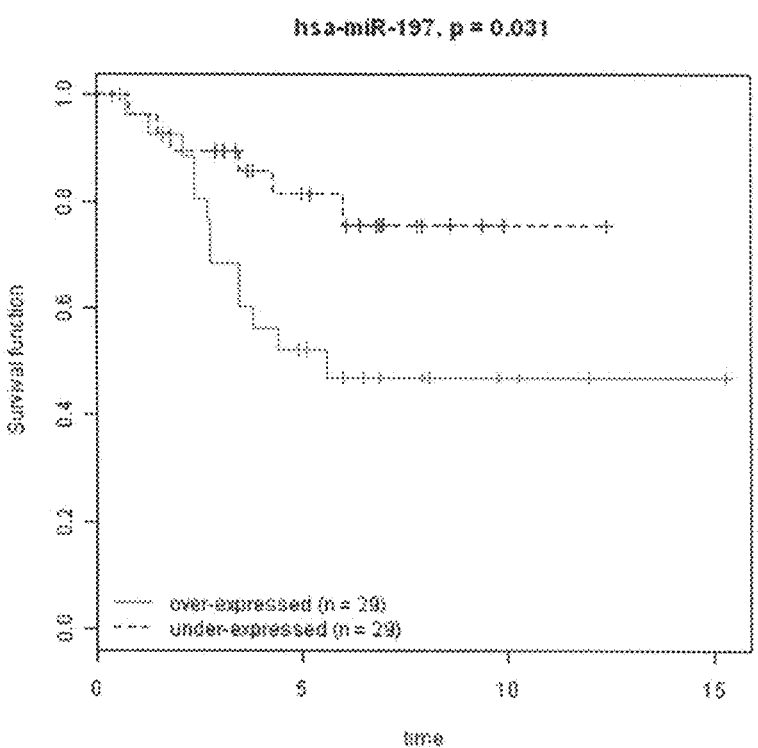
Figure 3Q:
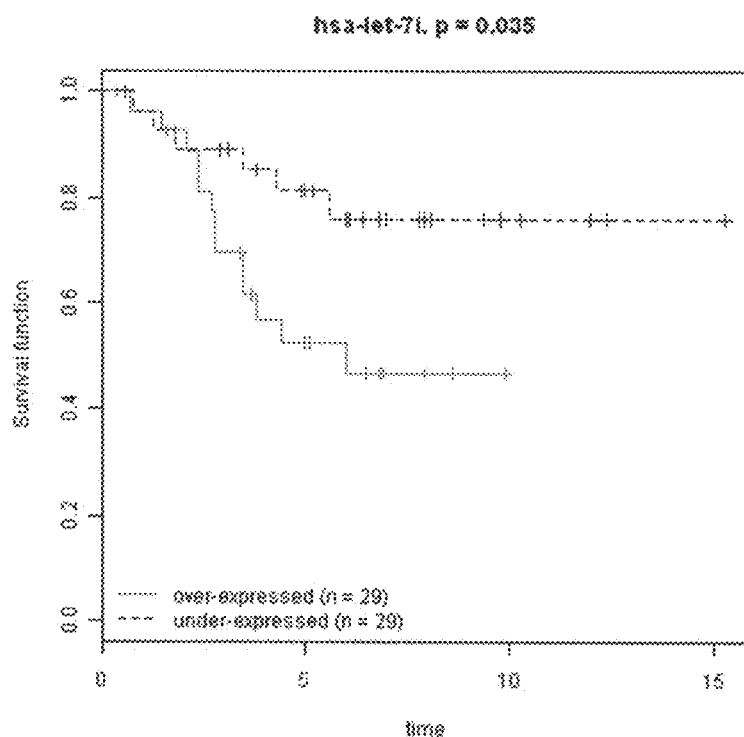
Figure 3R:
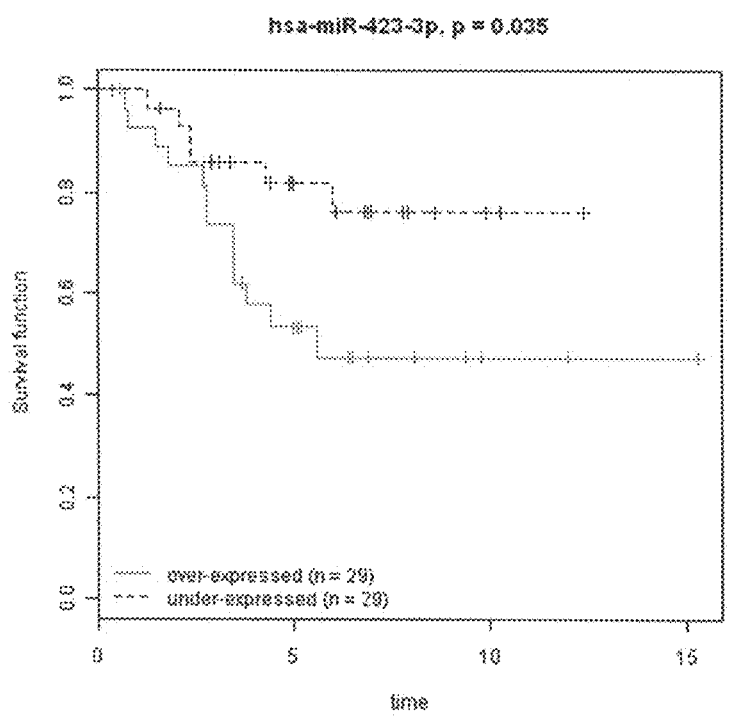
Figure 3S:
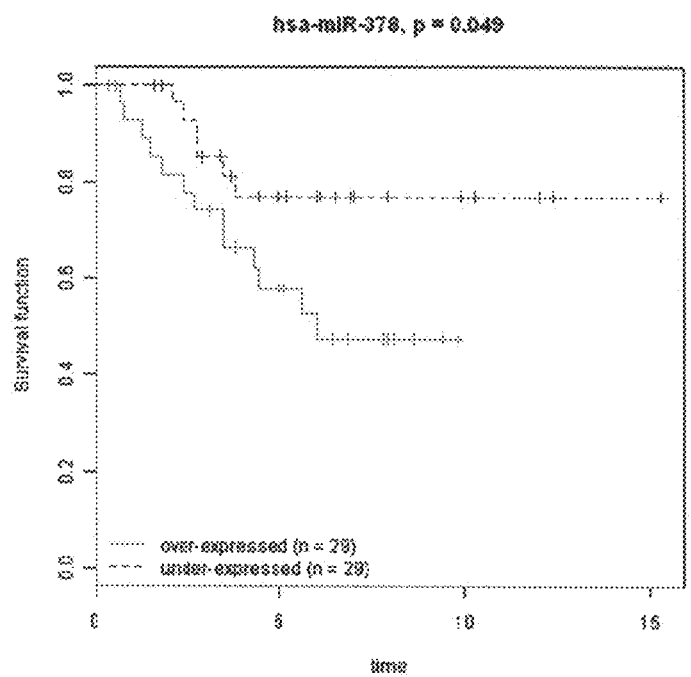

The Kaplan Meier curves for the miRNAs associated with overall-survival in IDV are shown in FIGS. 3K-3S, where FIG. 3K shows miR-21; FIG. 3L shows miR-221; FIG. 3M shows miR-652; FIG. 3N shows miR-106b*; FIG. 3O shows miR-28-3p; FIG. 3P shows miR-197; FIG. 3Q shows let-7i; FIG. 3R shows miR-423-3p; and, FIG. 3S shows miR-278.

Example 3 miR-210 and HIF1A Coupling in Breast Cancer Progression

Since miR-210 is inducible by hypoxia and to regulate genes involved in tumor initiation, analysis was made of HIF1A and the primary RNA for miR-210 (pri-mir-210) in breast cancer progression, using Affymetrix microarray data. The data show a very good correlation between HIF1A and pri-mir-210 RNA ($p<0.001$).

Figure 4:
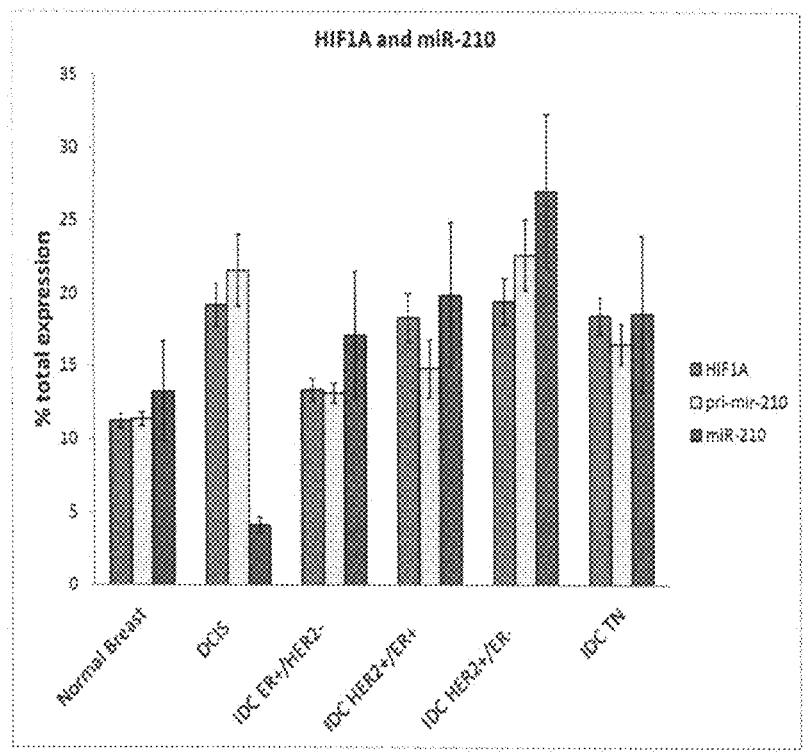
FIG. 4. The expression of mature miR-210, its primary RNA (pri-mir-210) and HIF1A, for each BC subtype and for normal breast. The average was computed within each group and reported as percentage of the total for that RNA among the different groups.

Each BC subtype for the relative amounts of mature miR-210, pri-mir-210 and HIF1A was compared (FIG. 4). The mature miR-210 expression is shown alongside that of pri-mir-210 and HIF1A RNA, for each BC subtype and for normal breast. The RNA measures are indicated as percent of the total, for each RNA, within the groups. The levels of HIF1A, pri-mir-210, and mature miR-210 were always maximal in the HER2+/ER− tumors, while the lowest levels of HIF1A and pri-mir-210 were in normal breast. Levels of HIF1A are believed to indicate hypoxia, and the low level of HIF1A in normal breast tissue was in agreement with normoxia. HIF1A mRNA was strongly induced in DCIS, where hypoxia is thus likely to occur. The pri-mir-210 transcription, which is driven by a hypoxia sensitive promoter, was accordingly activated in DCIS. The HIF1A/pri-mir-210 ratio was maintained across the diverse IDC subgroups. There was a single exception to coupling of mature miR-210 and pri-mir-210 RNA in DCIS. DCIS expressed high levels of HIF1A and pri-mir-210, suggesting hypoxia, but by far the lowest level of mature miR-210 in the series indicating strong pressure for strict down-regulation.

Example 4

A Restricted Set of Breast Cancer Genes Defines the In Situ and Invasive Transitions In view of results described herein and the unique role of miR-210 in invasion and prognosis, the proteins and functions controlled by its expression in BC were further investigated. The whole transcriptomes from Affymetrix profiles of 42 normal breast, 17 DCIS and 118 IDC samples (51 ER+/HER2−, 17 HER2+/ER−, 17 HER2+/ER+ and 33 TNBC) were examined. Genes compatible with being direct or indirect targets of miR-210 were searched, i.e., those with antagonist behavior to that of miR-210, up-regulated in DCIS and down-regulated in IDC. DCIS cases had 4524 up-regulated probe sets (out of 8930, FDR<0.05); among them, 1761 probe sets (corresponding to 1353 genes) were down-regulated in IDC, thus representing miR-210 targets or its downstream effects. Breast cancer was the only disease significantly associated with these genes (25 genes; Enrichment p<0.001; FIG. 19—Table 11).

Breast cancer genes regulated in an antagonistic fashion to miR-210, along the DCIS/IDC progression axis, included RB1, BRCA1, FANCD, FANCF, PP2CA, PARP1, NLK, E-cadherin (CDH1) and EHMT1 (FIG. 5 and FIG. 6). Pathways regulated by genes inversely related to miR-210 in BC were: caspase cascade in apoptosis, HER2 receptor recycling, TNFR1 signaling, FAS signaling (CD95) and BRCA1, BRCA2 and ATR in cancer susceptibility. Some of these genes were also differentially regulated according to their splicing isoforms. EGFR classical isoforms were expressed in normal breast and down regulated in DCIS. Intriguingly, a truncated EGFR variant (uc003tqi.2), lacking the whole tyrosine kinase domain, was not expressed in normal breast or in IDC, but specifically over-expressed in DCIS. Splicing variants of other genes exhibiting differential tumor subgroup expression were nibrin and ErbB3.

Example 5

Patient Characteristics and Integrated Profiles in the TCGA IDC Cohort

Integrated miRNA/mRNA tumor profiles (19262 mRNAs and 581 miRNAs) were studied in 466 primary IDCs from female patients with no pre-treatment (TCGA IDC cohort). Only patients with fully characterized (mRNA and miRNA profiles) tumors and with at least one month of overall survival (OS) were included in the study. Extended demographics for these patients, characterized by the TCGA consortium, are provided in FIG. 20. Raw RNA, DNA methylation (meDNA), somatic mutations and clinical data were obtained from the TCGA data portal. To establish the integrated mRNA/miRNA expression profile we normalized mRNAs as RPKM and miRNAs as reads per million of total aligned miRNA reads. The variance of the $\log_2$ normalized reads for each gene was compared to the median of all the variances. The genes more variable than the median gene were retained in the integrated profile (p<0.05). After this intensity variation filter was used, 7735 mRNAs and 247 miRNAs were present in the integrated RNA profile. DNA methylation (meDNA) was studied using the Infinium 450K platform on 296 patients from the same IDC cohort. The M value, i.e., the $\log_2$ ratio of the intensities of a methylated probe versus its corresponding un-methylated probe, was used to measure CpG methylation. The Catalogue Of Somatic Mutations In Cancer database (ver. 60) was used to identify the genes which are known to harbor functional somatic mutations in cancer. The breast cancer dataset was incremented with the highly related ovarian cancer dataset in order to evaluate a large tumors sample size. The genes with at least two validated somatic mutations resulting in alteration of the primary protein structure were identified.

Survival Analysis

Clinical covariates for the IDC tumors and patients are summarized in FIG. 20. To compute the Kaplan Meier distribution, the group with gene over-expression was assigned to samples with expression larger than median expression. The test of equality for survival distributions was performed using the Log-Rank method (Mantel-Cox), except when explicitly stated. Hazard ratios (HRs) and Kaplan-Meier curves were calculated for the RNAs in each independent subclass. RNAs which had significant both HRs and Log-Rank tests (p<0.05) in at least two subclasses (within the same clinical or molecular class) were selected. Additional criteria, required for the selection of coding genes, were the association of DNA methylation with OS and the presence of somatic mutations in the COSMIC database. The association between DNA methylation and OS was carried out using univariate Cox regression (FIG. 26.-FIG. 27). A majority rule voting procedure was applied to all significant hazard ratios of the CpG sites for each prognostic gene (FDR<0.001); e.g., the DNA methylation of a gene with most significant CpG HRs lower than 1 would be defined as negatively correlated to outcome, or vice-versa. For the multivariable analysis, the Cox proportional hazard model was applied to all covariates that had shown statistical significance (p<0.05) at the univariate level. The Wald test was used in a backward stepwise selection procedure to identify genes or covariates with significant independent predictive value and to estimate hazard ratio (HR) and 95% confidence interval (CI). All reported p values were two-sided. All analyses were performed using SPSS (version 21) or R/BioConductor (version 2.10).

Definition of Risk Predictor and ROC Curve

The gene weights for the linear RNA risk predictor were computed using the supervised principal component method. The Kaplan-Meier survival curves for the cases predicted to have low or high risks (median cut) were generated using ten-fold cross-validation. Multivariate models incorporating covariates such as N stage, disease stage, intrinsic subtypes, age, ER status, PR status, TP53 mutation, and PIK3CA mutation were built similarly. The statistical significance of the cross-validated Kaplan-Meier curves and Log-Rank statistics was determined by repeating the process 1000 times on random permutations of the survival data. For the RNA model, the p value tested the null hypothesis that there was no association between expression data and survival. For the combined RNA and clinical covariates model, the p value addressed whether the expression data for a gene adds significantly to risk prediction when compared to the covariates.

The ability of the models to predict outcome was assessed by comparing the AUC of the respective ROC curves. Analysis of area under curve (AUC) for the Receiver Operating Characteristic (ROC) curve was conducted using the survivalROC package in R, allowing for time dependent ROC curve estimation with censored data. Since in all of the survival analyses, fewer events occurred after 60 months (see Kaplan-Meier curves), the ability of models to predict outcome at, and around, this time point were compared. The ROC curve plots the true-positive vs. false-positive predictions, thus higher AUC indicates better model performance (with AUC=0.5 indicating random performance). RNA risk scores and groups (risk-high or -low defined above) were based on weightings in the linear risk predictor.

Independent Cohorts for the Validation of the 34-Gene Prognostic Signature

To validate the prognostic signature obtained from the TCGA IDC cohort, seven retrospective series of primary breast cancer patients who had complete 10-years follow-up, for a total of 2104 patients were used. In the UK cohort (n=207) seventy-four percent of the patients had IDC, while the remaining breast cancers were mostly lobular (12%) or mixed (7%). The clinical endpoints for the UK cohort towards distant relapse-free survival (DRFS) were distant metastasis detection or death, or the date of last assessment without any such event (censored observation). The expression of miRNA (GSE22216) was measured using Illumina miRNA v.1 beadchip and that of mRNA (GSE22219) using Illumina Human RefSeq-8 beadchip. The assays measured 24332 mRNAs and 488 miRNAs. Quantiles normalization was used for both arrays, and for the integrated profile. Validation of the mRNA prognostic component was performed on six additional Affymetrix breast cancer profiles. The Wang cohort was composed by 180 lymph-node negative relapse free patients and 106 lymph-node negative patients that developed a distant metastasis (GSE2034, n=286). The Hatzis cohort was used to study response and survival following neoadjuvant taxane-anthracycline chemotherapy (GSE25066, n=508). The Kao cohort was used to identify molecular subtypes of breast cancer through gene expression profiles of 327 breast cancer samples and determine molecular and clinical characteristics of different breast cancer subtypes (GSE20685, n=327). The Bos cohort was used to study brain metastasis, one of the most feared complications of cancer and the most common intracranial malignancy in adults (GSE12276, n=195). The TNBC cohort was assembled from German patients to characterize triple negative breast cancer (GSE31519, n=383). The TRANSBIG cohort was composed of Belgian patients and applied to the validation of a 76-gene prognostic signature for the prediction of distant metastases in lymph node-negative patients (GSE7390, n=198). DRFS was the clinical endpoint for all the validation cohorts, with the exceptions of Kao and TRANSBIG, where OS used. The seven validation cohorts were also used for the comparison of the 34-gene integrated signature to other prognostic BC signatures.

Biological Processes Associated to Common Risk Genes

To investigate the cellular functions associated with a single gene, even a microRNA, a GO analysis was performed on the mRNAs with whom the gene had positive, or negative, Spearman correlation (FDR<0.001). The BiNGO plugin in Cytoscape was used to retrieve the relevant GO annotations and propagate them upwards through the GO hierarchy. The hypergeometric test, in which sampling occurs without replacement, was used to assess the enrichment of gene ontology (GO) terms in the survival gene-set in the form of a P-value. The GO P-values were corrected using Benjamini and Hochberg method.

The biological processes activated or repressed in association with the common risk genes were examined. With the exception of lipid modification and phosphoinositide phosphorylation (PIK3CA, SMG1 and CPT1) there was not functional enrichment when all the coding genes in the risk predictor were considered together. This finding was in agreement with the risk genes impacting on independent pathways. Each single gene was investigated, whether an mRNA or a miRNA, by performing GO analysis on the mRNAs with whom it correlated in the integrated RNA profile. Genes involved in mitotic cell cycle and nuclear division were positively associated with miR-484. miR-328 was correlated with genes of the M phase and of DNA repair, miR-874 with genes involved in cell adhesion. miR-484 was negatively correlated with genes in morphogenesis and angiogenesis, and also in the development of epidermis and the assembly of hemidesmosomes, which anchor epithelial cells to extracellular matrix components such as the basal laminae. CPT1A was associated with the mammary gland branching involved in thelarche, the onset of postnatal breast development, usually occurring at the beginning of puberty, as well as Ral GTPase regulation. C2CD2 was associated with the repression of genes involved in the development of gonadal mesoderm and in the regression of the mullerian duct, including NME1 and NME2 (members of the anti metastatic NM23 family). The expression of PIK3CA was associated with activation of protein phosphorylation and transcription initiation and with the repression of mitochondrial ATP synthesis coupled proton transport.

Results

Figure 35:
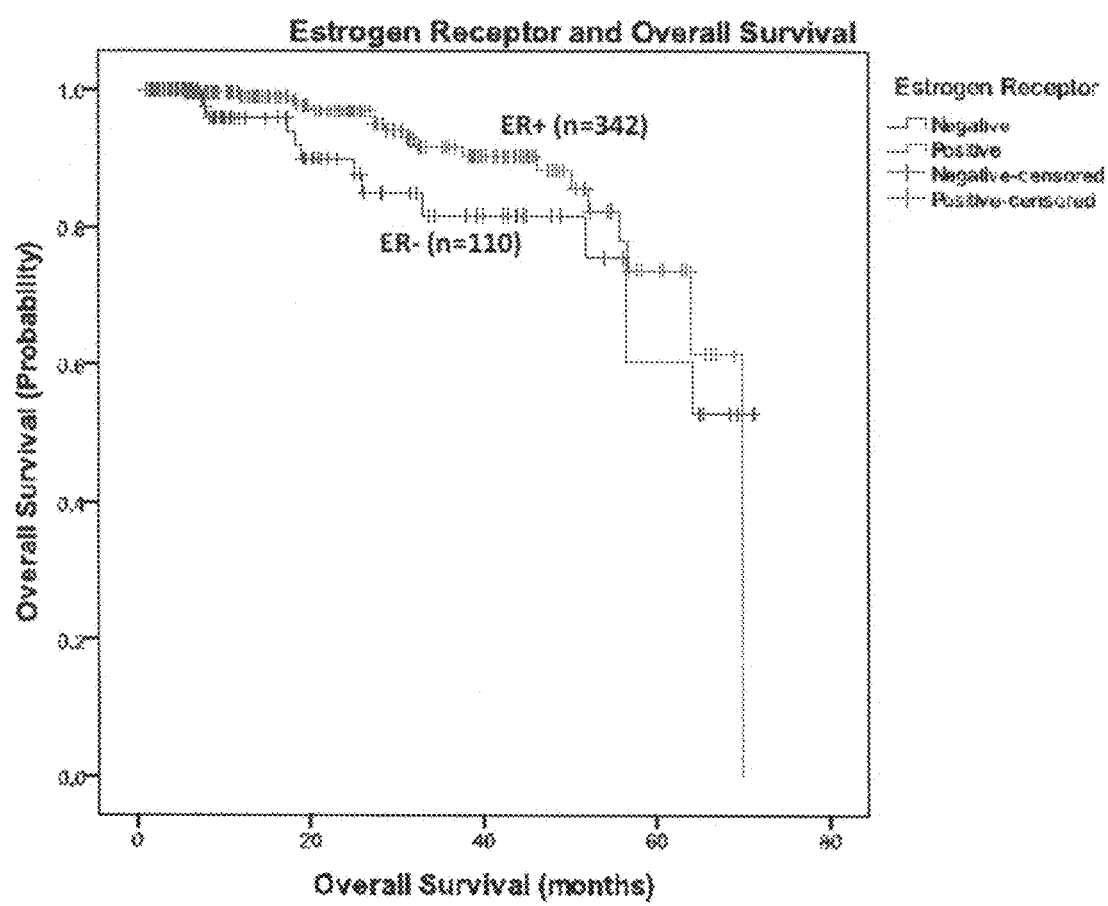
FIG. 35. Kaplan Meier survival estimates by the Estrogen Receptor (ER) status in invasive ductal carcinoma (Breslow test, P-value=0.016).
Figure 36:
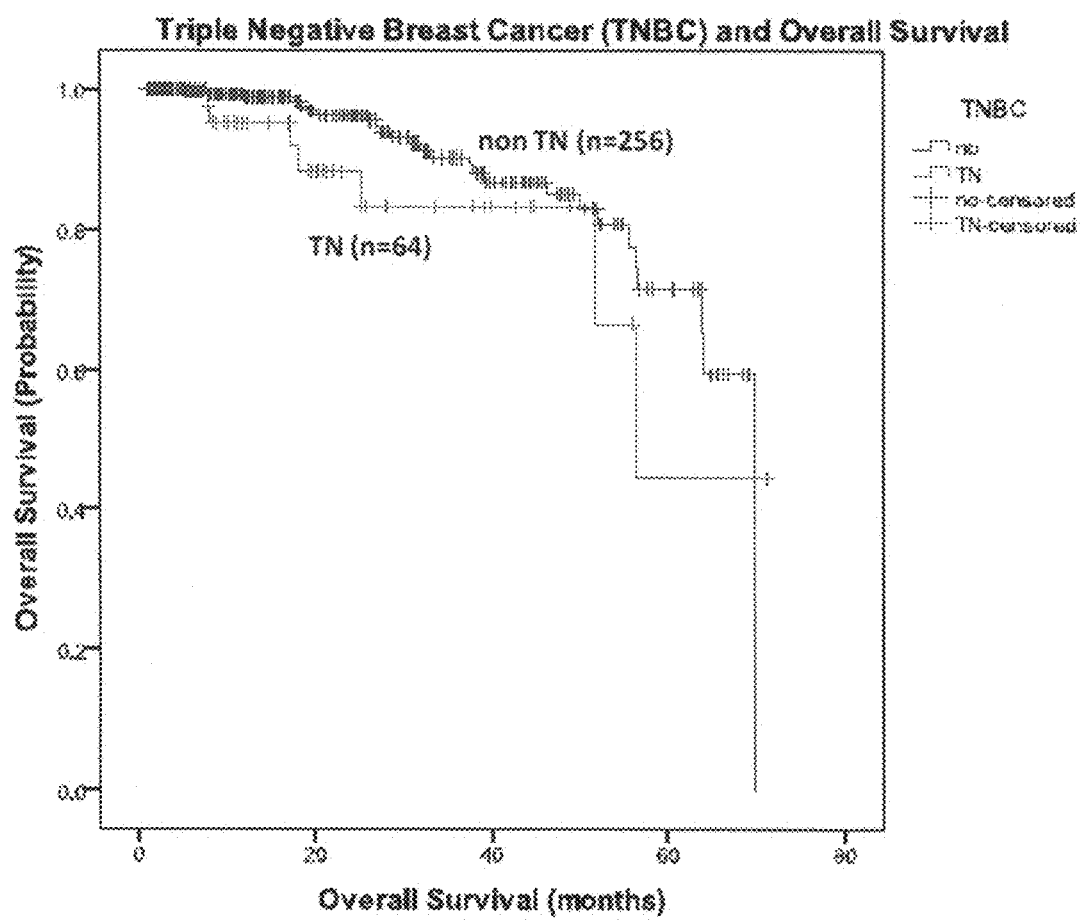
FIG. 36. Kaplan Meier survival estimates by the Triple Negative (TNBC) status in invasive ductal carcinoma (Breslow test, P-value=0.041).
Figure 37:
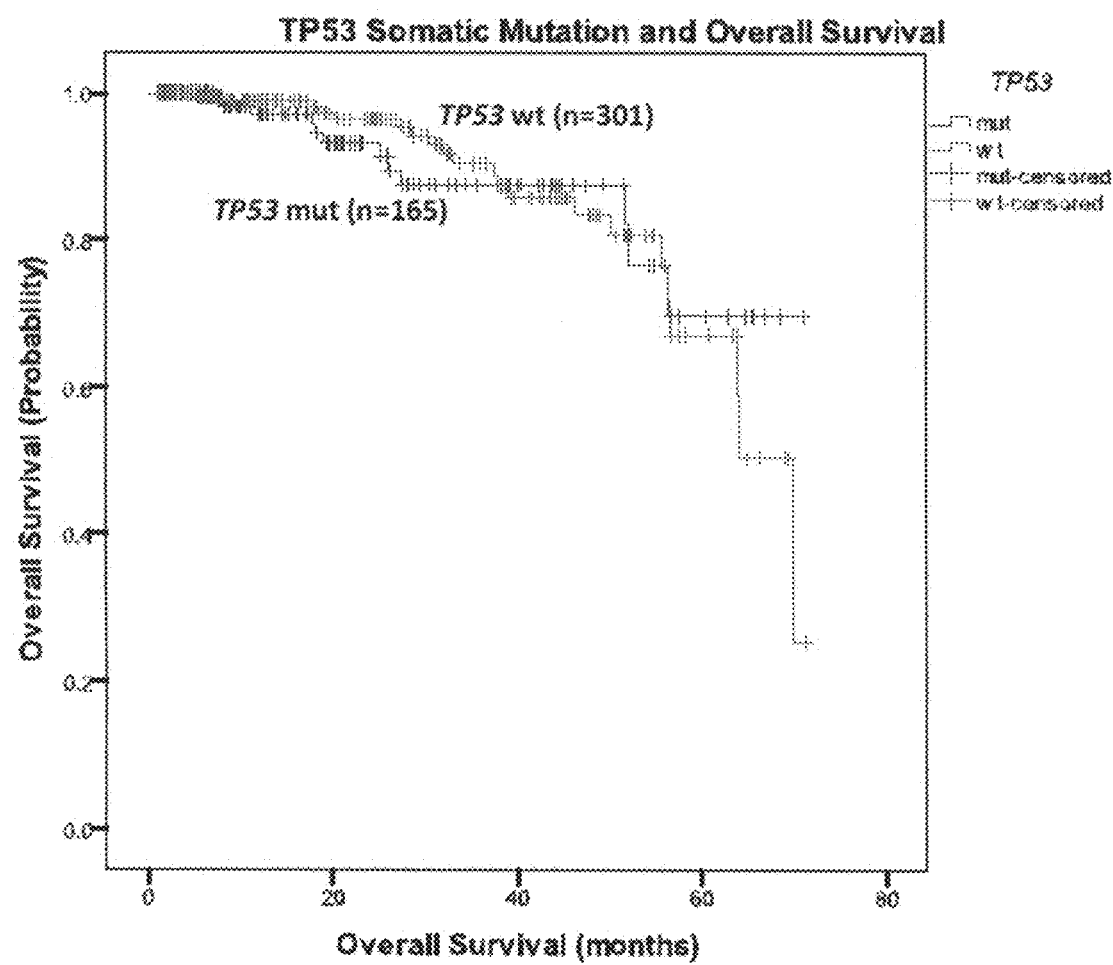
FIG. 37. Kaplan Meier survival estimates by the TP53 somatic mutation status in invasive ductal carcinoma (Log-rank test, non significant).
Figure 38:
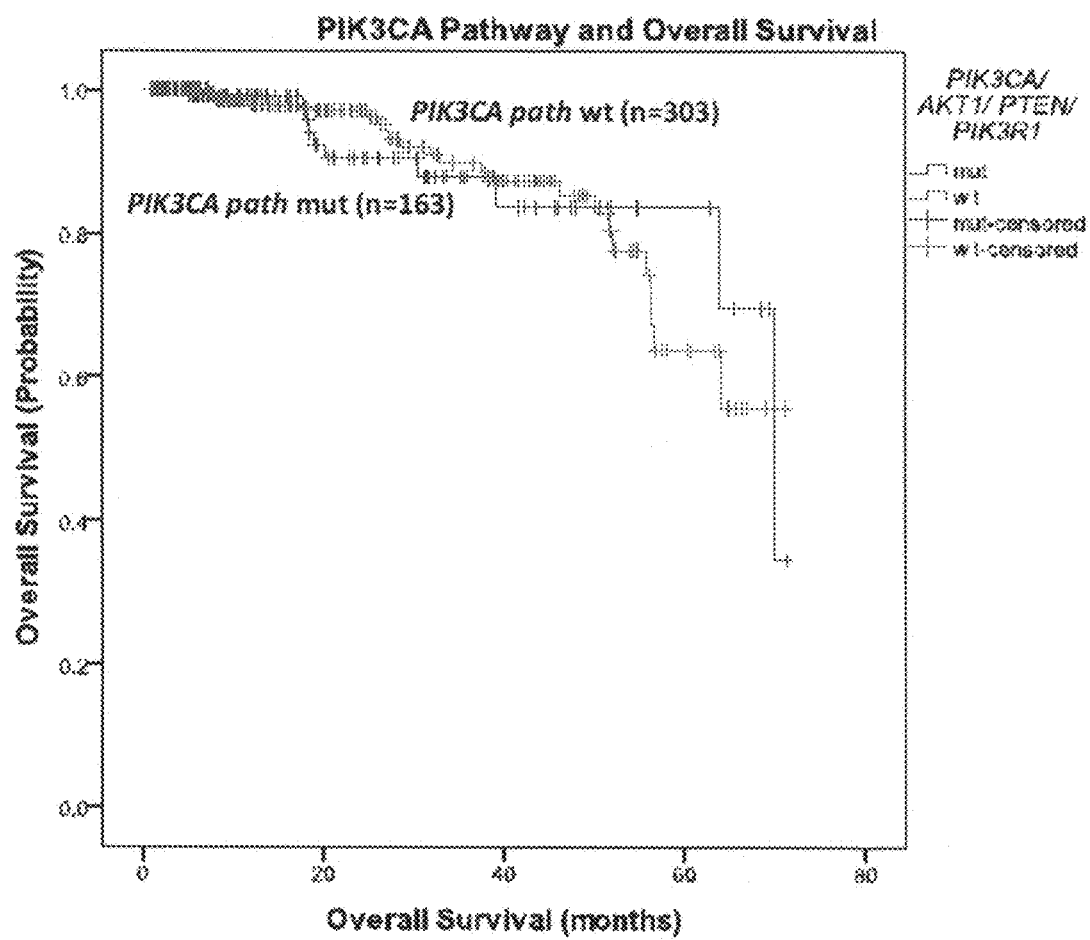
FIG. 38. Kaplan Meier survival estimates by the PIK3CA pathway somatic mutation status in invasive ductal carcinoma (Log-rank test, non significant).

Integrated molecular profile and clinical parameters in the TCGA IDC cohort Integrated miRNA/mRNA tumor profiles (7735 mRNAs and 247 miRNAs) were studied for 466 primary IDCs in the TCGA IDC cohort (FIG. 20). miR-210, is associated with the transition from ductal carcinoma in situ (DCIS) to IDC, and with poor prognosis, was the most upregulated miRNA in primary tumors which had distant metastasis (p=0.02). Before studying the prognostic values of RNA expression and DNA methylation, univariate survival tests were conducted to assess the relationship between clinical parameters and outcome in the TCGA IDC cohort. N stage, M stage, disease stage, T stage, and intrinsic subtype (FIG. 30-FIG. 34) were significantly associated with OS. ER positive patients showed a more favorable outcome and patients with triple negative breast cancer a worse prognosis (FIG. 35-FIG. 36). Menopausal status and age were not associated with OS. Although somatic mutations in IDC were associated with specific intrinsic subtypes (TP53 with Basal-like and HER2-enriched, whilst PIK3CA with Luminal A), they were not associated with OS (FIG. 37-FIG. 38). The results of this assessment shows that the survival data for the TCGA IDC cohort, although containing a majority of censored data, were informative and appropriate for use in further molecular studies.

Association of OS with miRNA/mRNA/meDNA in the TCGA IDC Cohort

The association of OS with the miRNA, mRNA, and DNA methylation profiles was then studied in detail for the TCGA IDC cohort. The goal was the identification of a set of common genes, if existing, consistently driving the outcome of the disease across the different clinical or molecular subtypes. The strategy and the underlying rationale are schematically shown in FIG. 22.

Univariate survival analyses for OS were conducted using the integrated mRNA/miRNA profile within each of the following independent classes: disease stage, lymph node involvement, surgical margin, pre or post-menopause, intrinsic subtype, somatic mutations (TP53, PIK3CA pathway, TP53/PIK3CA double mutants, GATA3, MAPKs, and remaining less frequently altered genes). The patient subclasses with different clinical or molecular characteristics represented disjoint sets within each class. An mRNA, or a miRNA, was selected only if significant in at least two independent subclasses from the same class. Since DNA methylation is a key mechanism in transcriptional control, the DNA methylation of coding genes was used an additional criterion for association with OS. The first focus was on the relation between CpG methylation and mRNA expression using the PIK3CA prognostic gene as a model. The methylated CpG sites, which correlated with PIK3CA expression, were all located in a 2.2 Kb region surrounding its first exon (FIG. 26), a region with strong acetylation of lysine 27 in histone H3 and high density binding of transcription factors. The majority (5 out of 6) of the significant CpG sites in this region had the expected negative correlation between DNA methylation and PIK3CA expression. Based on this finding, a majority rule was used to determine the type of association between a gene's methylation and OS. When most of the significant methylation sites for a gene (FIG. 27) had HR lower than 1, than the correlation between the gene's methylation and outcome was defined as "negative". This procedure allowed for the discovery of the genes that had paired associations of poor outcome with both RNA over-expression and DNA hypomethylation, or vice-versa. The DNA methylation test was not applied to miRNAs, because of the limited number of CpG sites assayed in those very small genes. Nevertheless most miRNAs passed the methylation test (data not shown). As a final step to refine the risk gene-set, only mRNAs with known protein mutations in cancer (according to the Catalogue Of Somatic Mutations In Cancer) were retained.

Figure 22:
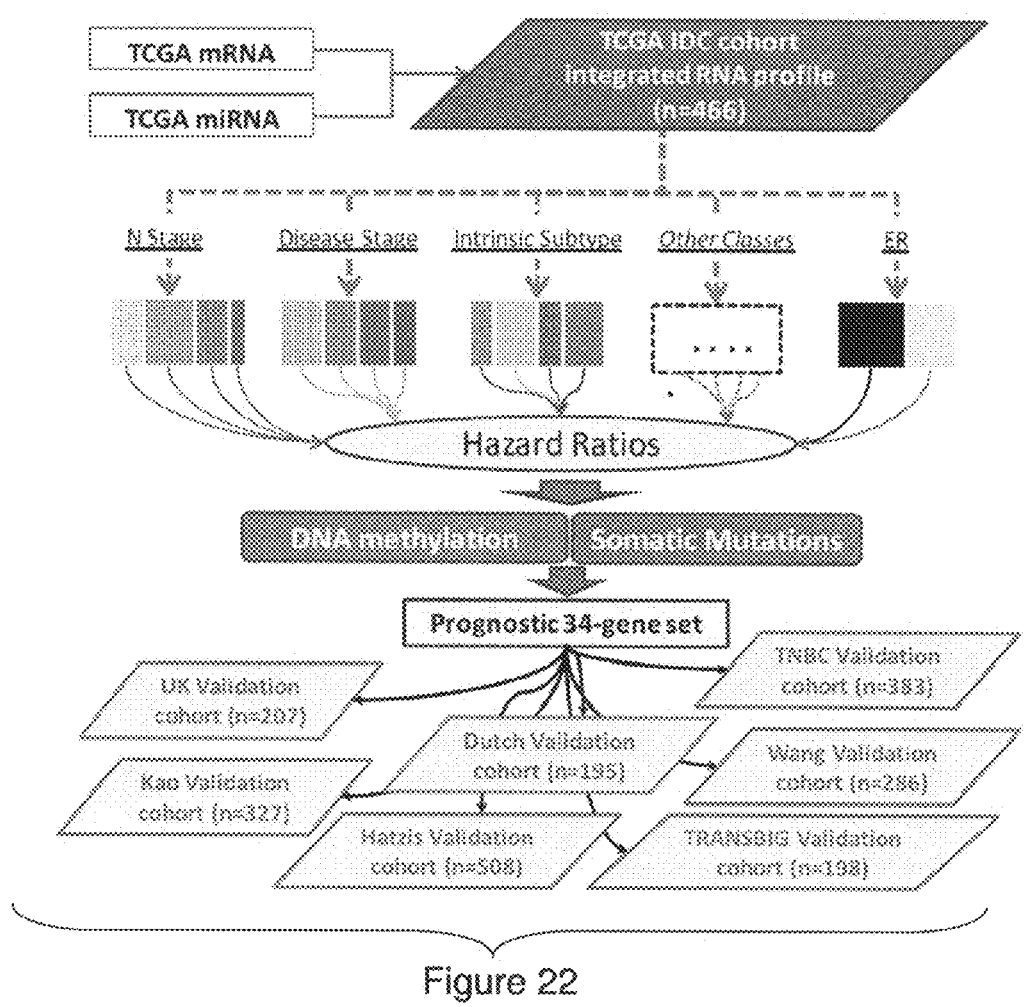
FIG. 22. The strategy used to derive and validate common prognostic mRNA and miRNAs (34-gene set) across different subclasses of breast cancer. mRNAs and miRNAs were integrated in a single RNA profile for IDC (TCGA cohort, n=466). Survival analysis was performed within the various subgroups of the following clinical and molecular classes: disease stage, lymph node involvement (N stage), surgical margin, pre or post-menopause, intrinsic subtype, somatic mutations (TP53, PIK3CA pathway, TP53/PIK3CA double mutants, GATA3, and remaining less frequently altered genes). The subclasses within a class represented disjoint patient sets, thus enabling immediate validation of the prognostic RNAs for that class. Hazard ratios (HRs) and Kaplan-Meier curves were calculated for the RNAs in each independent subclass of the TCGA cohort. RNAs which had significant both HRs and Log-Rank tests (p<0.05) in at least two subclasses were selected. Additional criteria required for the selection of coding genes were the association of DNA methylation with OS and the presence of somatic mutations in the COSMIC database. Seven independent validation cohorts (total n=2104 patients) were used to re-assess the prognostic 34-gene set generated on the TCGA cohort.

The stringent multistep selection applied, and shown in FIG. 22, lead to the discovery of: i) the identification of the common RNAs related to clinical outcome across IDC patients, not restricted to specific tumor subclasses, ii) the validation of the prognostic genes in non-overlapping patient subclasses, iii) the use of DNA methylation as an independent molecular parameter to confirm RNA expression, and iv) the identification of prognostic genes with bona fide cancer activity (FIG. 28).

Figure 23:
FIG. 23. The mRNAs and miRNAs associated with OS in different clinical and molecular subclasses of invasive ductal carcinoma (TCGA cohort). The matrix visualizes the significant hazard ratios (HRs) for the 34 prognostic coding genes and miRNAs in the TCGA IDC cohort (according to the procedure in FIG. 22 and listed in FIG. 28). The HR for mRNAs or miRNAs with significant univariate Cox regression (p<0.05) are displayed on a log$_2$ scale, irrespective of the Log-Rank test. Red squares indicate HRs>1 and blue squares indicate HRs<1. The classes for which at least a gene or miRNA was significant are shown.

The prognostic matrix (FIG. 23) visualizes all significant hazard ratios (p<0.05) for the 24 mRNAs and the ten miRNAs that satisfied the proposed criteria. The genes in the matrix are referred to herein as "the prognostic 34-gene set." Some known BC genes (for example, NME3, an isoform of the NM23 family) were associated with outcome only within a single subclass and therefore did not satisfy the selection requirements. Essentially, all selected mRNAs and miRNAs had hazard ratios larger than 1 and thus their over-expression correlated with poor outcome. DAAM1, thought to function as a scaffolding protein for the Wnt-induced assembly of a disheveled (Dvl)-Rho complex, was the prognostic gene harboring the highest correlation with lymph node involvement (Spearman correlation test, p<0.001, FDR=0.001).

Integrated IDC Risk Predictor in the TCGA IDC Cohort

The prognostic 34-gene set was used to develop two multivariable models and predict OS in patients with IDC:
a) an "RNA model", using only mRNA and miRNA expression data, was composed only of genes; and,
b) a "combined model", which in addition included molecular and clinical covariates.

Figure 24A:
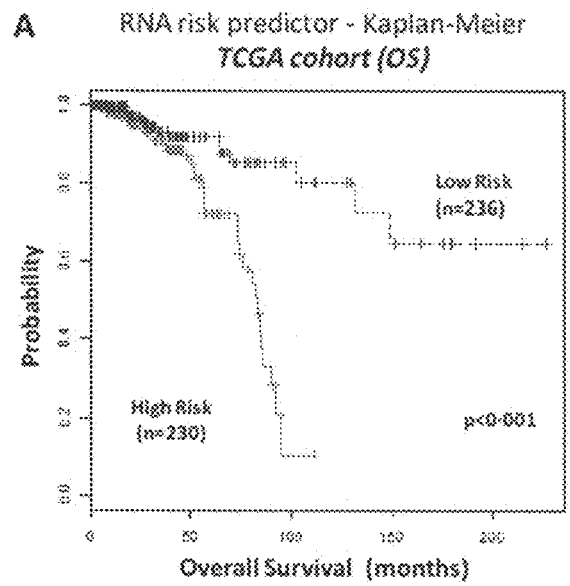
FIGS. 24A-24B. Kaplan-Meier and ROC curves for the prognostic 34-gene set in IDC (TCGA cohort)

The survival high and low risk groups were constructed using the supervised principal component method. A linear risk predictor for OS in IDC (FIG. 29 and FIG. 24A) was then discovered.

Figure 24B:
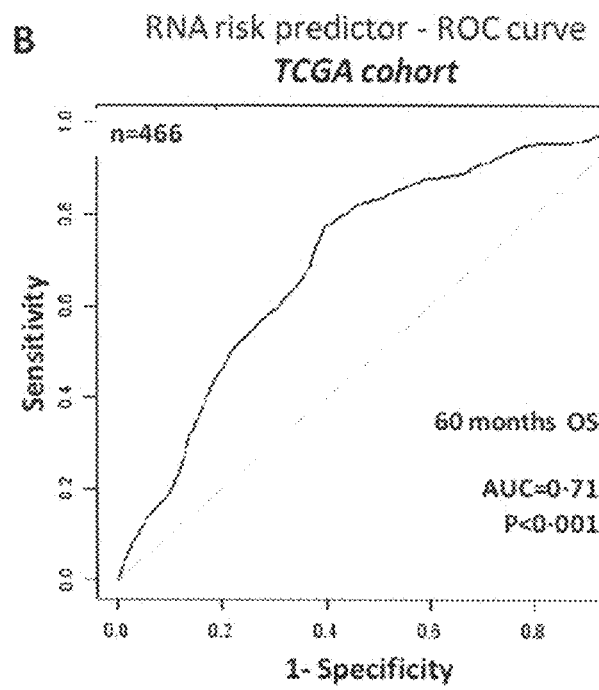

The analysis of area under curve (AUC) for the Receiver Operating Characteristic (ROC) was conducted allowing for time dependent ROC curve estimation with censored data (FIG. 24B). The AUC for the integrated IDC risk predictor was 0.71 at 60 months of OS (p<0.001). To evaluate the independent prognostic values of the integrated RNA predictor, a combined model was developed, including also lymph node involvement (N stage), disease stage, T stage, molecular subtype, age at diagnosis, TP53 mutation status, PIK3CA pathway mutation status, ER status, and PR status. The final combined model included the linear risk predictor and the N stage as the only remaining clinical or molecular covariate. The ROC curve for the combined model had a significant AUC, but not larger than that of the RNA model. Thus, the RNA levels in the IDC risk predictor had independent prognostic values, while the other clinical and molecular covariates, with the exception of N stage, did not.

Validation of the 34-Gene Prognostic Signature in Independent BC Cohorts

Figure 25A:
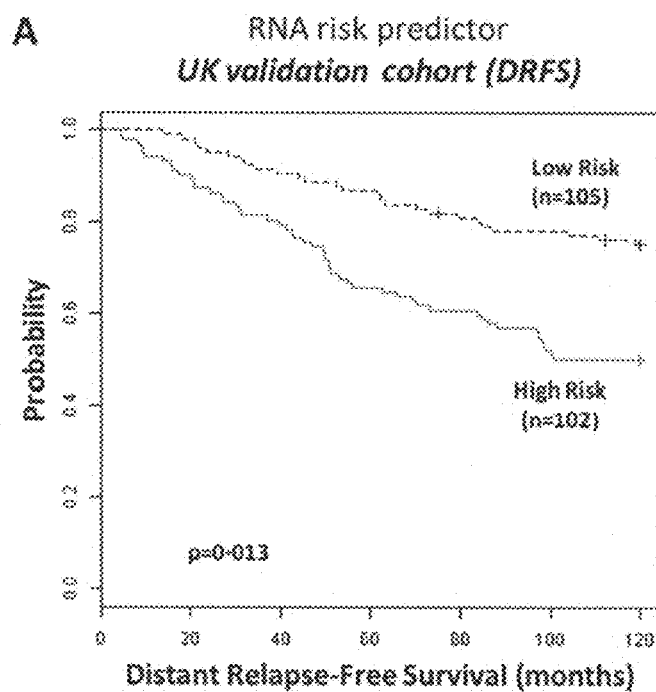
FIGS. 25A-25B. Kaplan-Meier and ROC curves for the prognostic 34-gene set in the UK validation cohort.
Figure 25B:
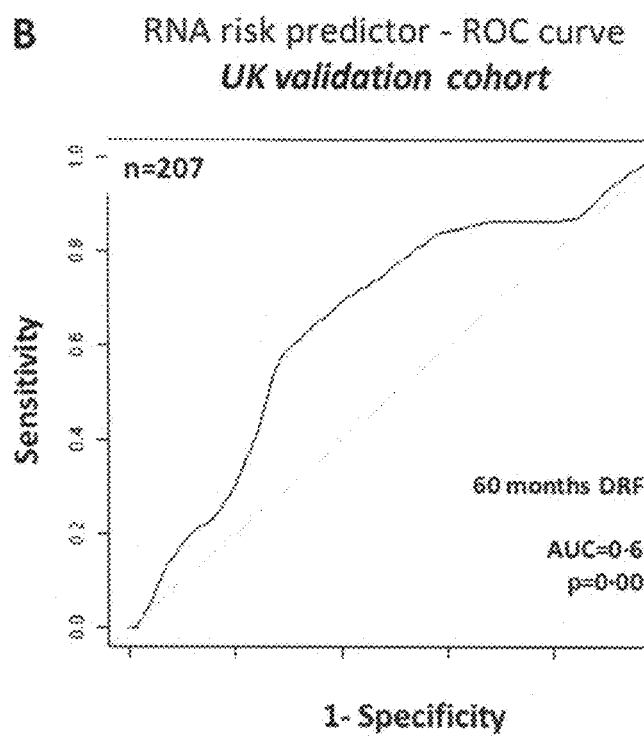
Figure 30:
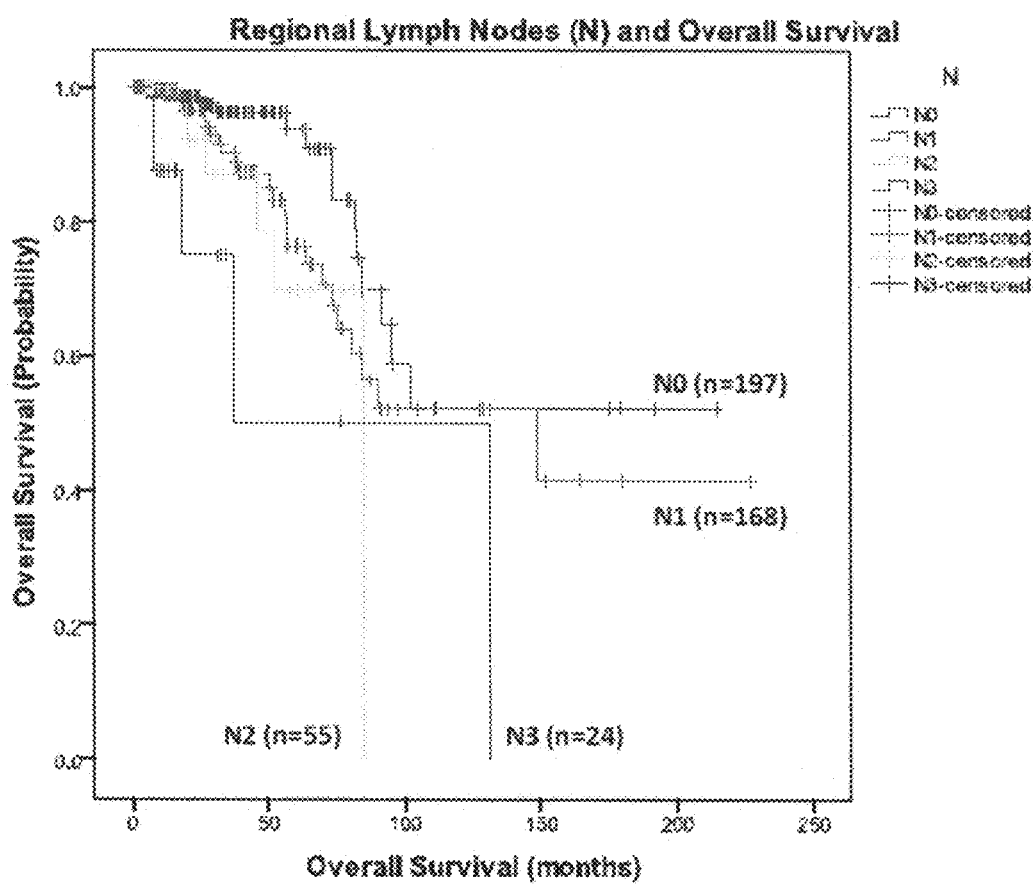
FIG. 30. Kaplan Meier survival estimates by Regional Lymph Node involvement (N) in invasive ductal carcinoma (Overall Log-rank test, P-value=0.005).
Figure 31:
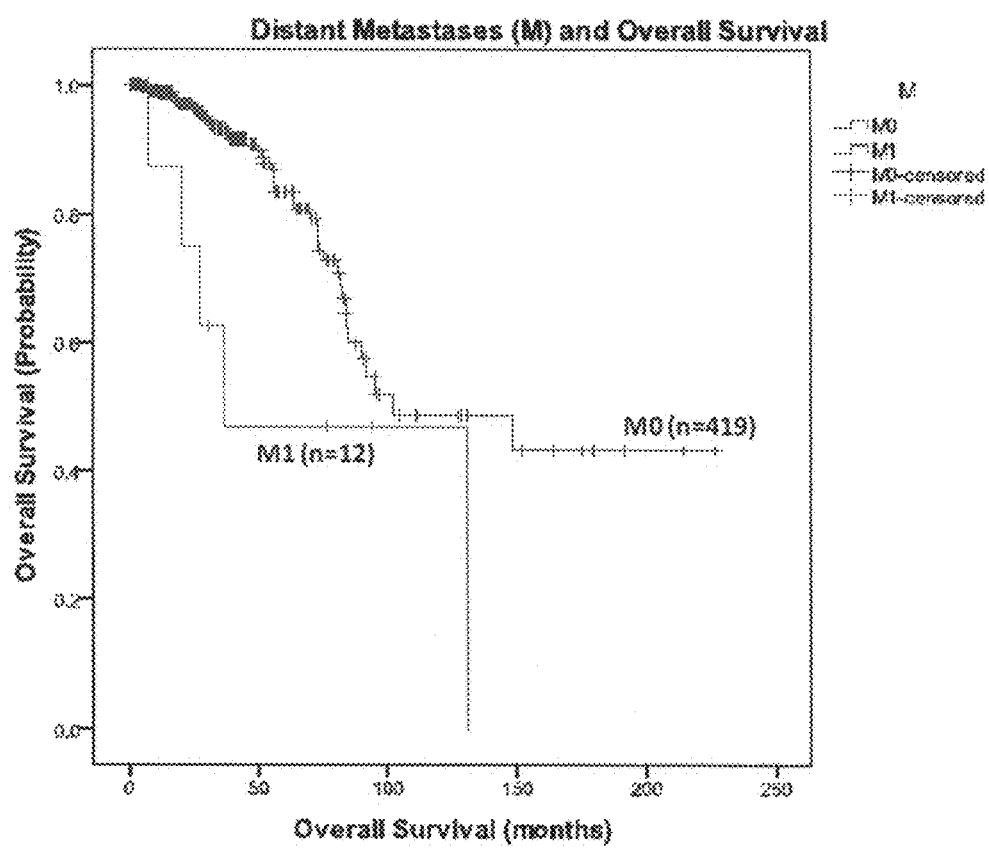
FIG. 31. Kaplan Meier survival estimates by Distant Metastases (M) in invasive ductal carcinoma (Overall Log-rank test, P-value=0.026).
Figure 32:
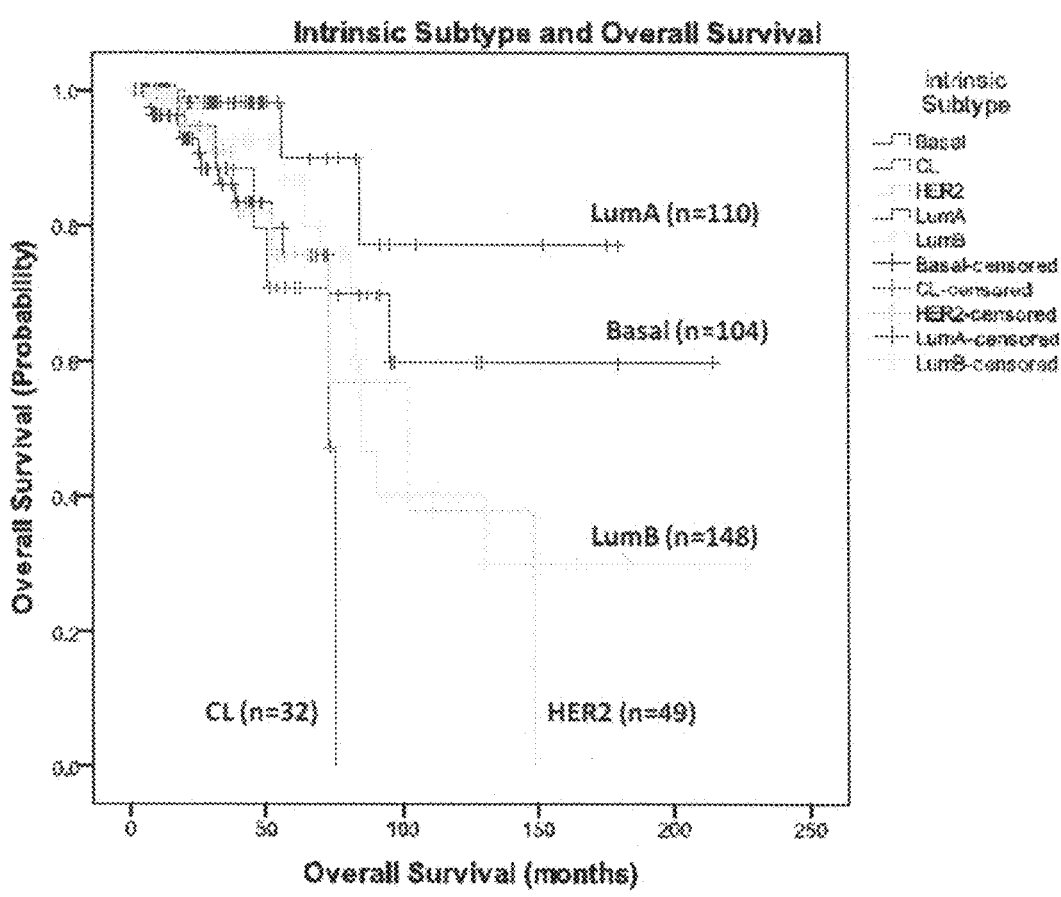
FIG. 32. Kaplan Meier survival estimates by intrinsic subtypes in invasive ductal carcinoma (Overall Log-rank test, P-value=0.042).
Figure 33:
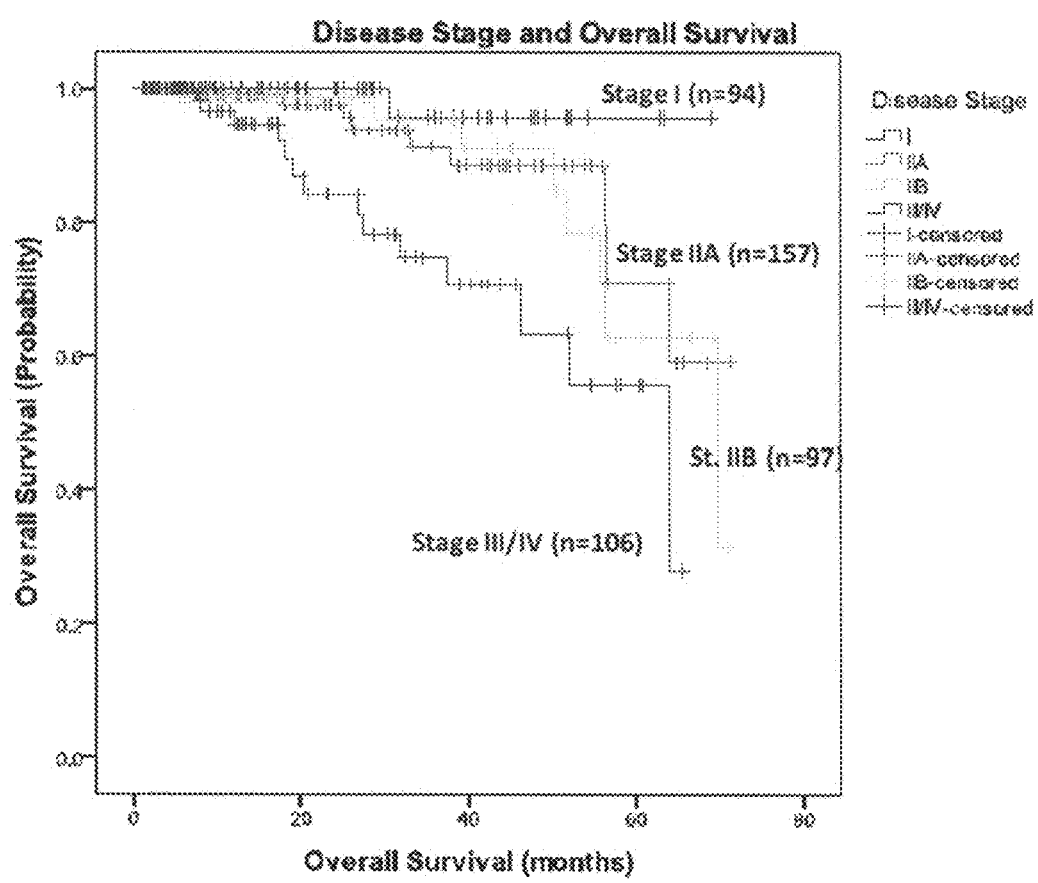
FIG. 33. Kaplan Meier survival estimates by the AJCC Disease Stage in invasive ductal carcinoma (Overall Log-rank test, P-value=0.002).
Figure 34:
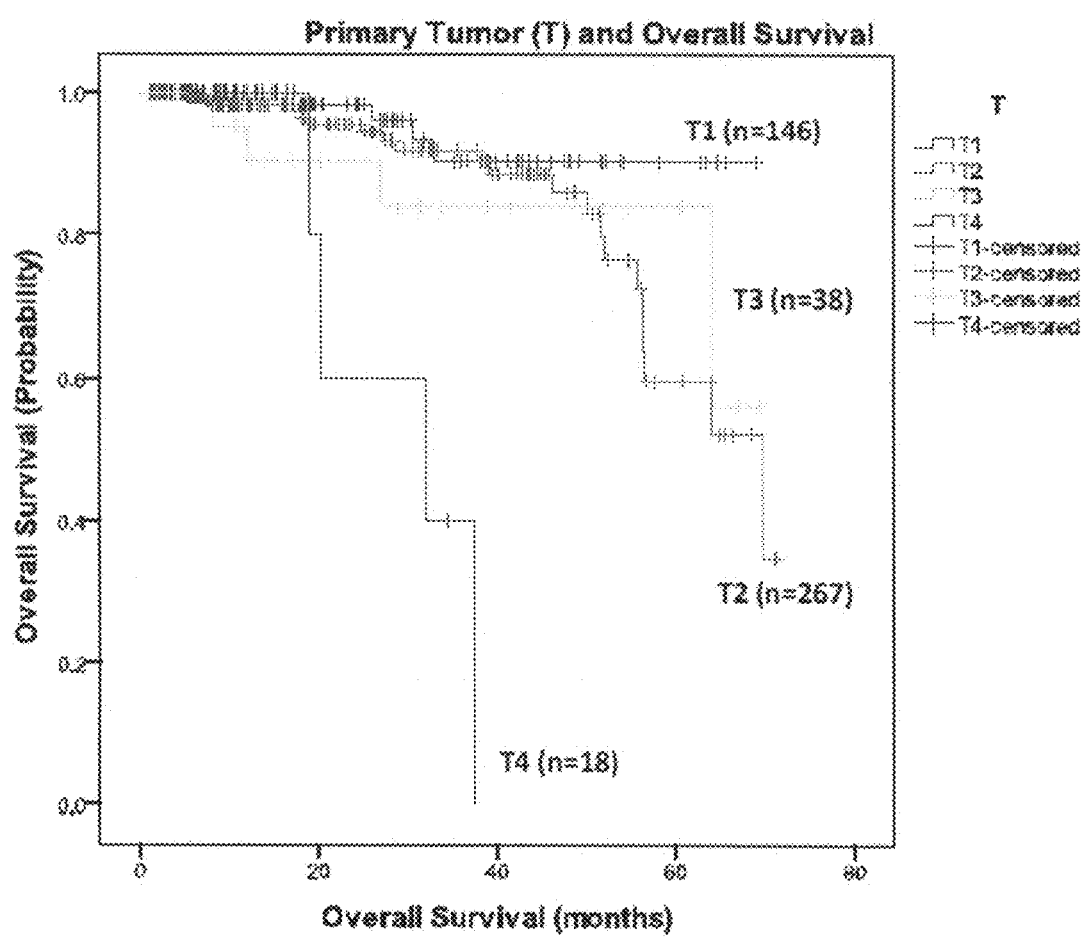
FIG. 34. Kaplan Meier survival estimates by the T stage in invasive ductal carcinoma (Overall Log-rank test, P-value <0.001).

The validation of the 34-gene prognostic signature was performed on three independent BC cohorts. First used was an UK cohort of 207 breast cancer patients. The miRNA/mRNA prognostic gene set was here re-assessed for prediction of distant relapse-free survival (DRFS). Nine miRNAs and 11 mRNAs, less than ⅔ of the 34 prognostic genes, were measured in the UK cohort. Nevertheless, the KM curve (p=0.013) and the ROC curve for the prognostic signature (AUC=0.65, p=0.001) were both significant (FIGS. 25a-25B). As there were no other available mRNA and miRNA combined expression data for large cohorts, the mRNA component of the prognostic signature on the Hatzis (n=508), Kao (n=327), TNBC (n=383), Bos (n=195), Wang (n=286), and the TRANSBIG (n=198) cohorts were also evaluated. The prognostic signature was predictive for these BC cohorts, characterized by Affymetrix profiles (FIG. 21).

Comparison of the 34-Gene Signature with Other Prognostic BC Signatures

The prognostic value of the 34-gene integrated signature was compared to that of five different signatures for the risk stratification of BC: the 21-gene, the 97-gene used for the Genomic Grade Index, the 70-gene, the 76-gene, and the 10-miRNA signatures. Each one of the six prognostic signatures was applied to eight different BC cohorts, for a total of 2570 patients (FIG. 21). The AUC of the ROC curves was calculated for each signature/cohort combination, thus generating a matrix of prognostic values (FIG. 21).

The 10-miRNA signature was predictive of DRFS, in the UK dataset where it was determined (AUC=0.75, p<0.001), but not in the TCGA cohort. In the TNBC cohort, all signatures tested were successful with similar performance (p<0.001). The 21-gene signature performed very well in all the cohorts, with the notable exception of the TCGA IDC cohort, where it was not significant (AUC=0.58, p=0.12). In the Bos cohort only the integrated 34-gene, the 21-gene and the 70-gene signatures had good prognostic value. The 34-gene (p<0.001) and the 97-gene (although with a borderline p=0.053) signatures were the only two with significant prognostic value in the large and heterogeneous TCGA IDC cohort.

Discussion of Example 5

IDC is characterized by different molecular subtypes which impact on the cellular pathways related to clinical outcome. The inventors herein determined whether common mechanisms are associated with overall survival (OS) across the IDC molecular and clinical classes. microRNAs (miRNAs) are modulators of cellular processes responsible for cancer that are encoded by mRNAs which in turn are regulated by DNA methylation. Because of these multiple relations, an integrated survival analysis was performed on a large breast cancer cohort of 466 patients, using genome-wide data for mRNA/miRNA expression and DNA methylation. The 34-gene prognostic signature discovered was successfully validated on seven breast cancer cohorts for a total of 2104 additional patients.

The 34-Gene Signature

As these cohorts were not treatment-naive, the identified RNAs could be not only prognostic but also predictive of response to treatment. However, the patients received different treatments, and thus the RNAs are independent of treatment. In addition, the integration of miRNA and mRNA profiles augmented the prognostic strength of the risk predictor. Also, DNA methylation was used as a criterion to confirm the association between mRNA expression and OS. The biomarkers that were discovered were consistent across eight different and heterogeneous breast cancer cohorts, for a total of over 2500 patients.

Notably, most of the 34 prognostic genes were not previously described in BC. Among the few known cancer genes in the prognostic signature, PIK3CA was one of the most prominent. PIK3CA is an example of oncogene addiction, also when it is not mutated, and thus is as a primary target for therapy. On the contrary, TP53, another frequently mutated cancer gene in BC, did not display such relevance. Finally, the genotype of either TP53 or PIK3CA did not add prognostic value to the RNA based risk predictor.

The validity of a marker is strengthened when it is applied to a set of data independent from the one that generated the association. The prognostic 34-gene set proved to be such a valid marker, as it was prognostic in all the cohorts studied.

Example 6

Methods, Reagents and Kits for Diagnosing, Staging, Prognosing, Monitoring and Treating Cancer-Related Diseases It is to be understood that all examples herein are to be considered non-limiting in their scope. Various aspects are described in further detail in the following subsections.

Diagnostic Methods

In one embodiment, there is provided a diagnostic method of assessing whether a patient has a cancer-related disease or has higher than normal risk for developing a cancer-related disease, comprising the steps of comparing the level of expression of a marker in a patient sample and the normal level of expression of the marker in a control, e.g., a sample from a patient without a cancer-related disease.

A significantly altered level of expression of the marker in the patient sample as compared to the normal level is an indication that the patient is afflicted with a cancer-related disease or has higher than normal risk for developing a cancer-related disease.

In certain embodiments, the markers are selected such that the positive predictive value of the methods is at least about 10%, and in certain non-limiting embodiments, about 25%, about 50% or about 90%. Also preferred for use in the methods are markers that are differentially expressed, as compared to normal cells, by at least two-fold in at least about 20%, and in certain non-limiting embodiments, about 50% or about 75%.

In one diagnostic method of assessing whether a patient is afflicted with a cancer-related disease (e.g., new detection ("screening"), detection of recurrence, reflex testing), the method comprises comparing: a) the level of expression of a marker in a patient sample, and b) the normal level of expression of the marker in a control non-cancer-related disease sample. A significantly altered level of expression of the marker in the patient sample as compared to the normal level is an indication that the patient is afflicted with a cancer-related disease.

There is also provided diagnostic methods for assessing the efficacy of a therapy for inhibiting a cancer-related disease in a patient. Such methods comprise comparing: a) expression of a marker in a first sample obtained from the patient prior to providing at least a portion of the therapy to the patient, and b) expression of the marker in a second sample obtained from the patient following provision of the portion of the therapy. A significantly altered level of expression of the marker in the second sample relative to that in the first sample is an indication that the therapy is efficacious for inhibiting a cancer-related disease in the patient.

It will be appreciated that in these methods the "therapy" may be any therapy for treating a cancer-related disease including, but not limited to, pharmaceutical compositions, gene therapy and biologic therapy such as the administering of antibodies and chemokines. Thus, the methods described herein may be used to evaluate a patient before, during and after therapy, for example, to evaluate the reduction in disease state.

In certain aspects, the diagnostic methods are directed to therapy using a chemical or biologic agent. These methods comprise comparing: a) expression of a marker in a first sample obtained from the patient and maintained in the presence of the chemical or biologic agent, and b) expression of the marker in a second sample obtained from the patient and maintained in the absence of the agent. A significantly altered level of expression of the marker in the second sample relative to that in the first sample is an indication that the agent is efficacious for inhibiting a cancer-related disease in the patient. In one embodiment, the first and second samples can be portions of a single sample obtained from the patient or portions of pooled samples obtained from the patient.

Methods for Assessing Prognosis

There is also provided a monitoring method for assessing the progression of a cancer-related disease in a patient, the method comprising: a) detecting in a patient sample at a first time point, the expression of a marker; b) repeating step a) at a subsequent time point in time; and c) comparing the level of expression detected in steps a) and b), and therefrom monitoring the progression of a cancer-related disease in the patient. A significantly altered level of expression of the marker in the sample at the subsequent time point from that of the sample at the first time point is an indication that the cancer-related disease has progressed, whereas a significantly altered level of expression in the opposite direction is an indication that the cancer-related disease has regressed.

There is further provided a diagnostic method for determining whether a cancer-related disease has worsened or is likely to worsen in the future, the method comprising comparing: a) the level of expression of a marker in a patient sample, and b) the normal level of expression of the marker in a control sample. A significantly altered level of expression in the patient sample as compared to the normal level is an indication that the cancer-related disease has worsened or is likely to worsen in the future.

Methods for Assessing Inhibitory, Therapeutic and/or Harmful Compositions

There is also provided a test method for selecting a composition for inhibiting a cancer-related disease in a patient. This method comprises the steps of: a) obtaining a sample comprising cells from the patient; b) separately maintaining aliquots of the sample in the presence of a plurality of test compositions; c) comparing expression of a marker in each of the aliquots; and d) selecting one of the test compositions which significantly alters the level of expression of the marker in the aliquot containing that test composition, relative to the levels of expression of the marker in the presence of the other test compositions.

There is additionally provided a test method of assessing the harmful potential of a compound in causing a cancer-related disease. This method comprises the steps of: a) maintaining separate aliquots of cells in the presence and absence of the compound; and b) comparing expression of a marker in each of the aliquots. A significantly altered level of expression of the marker in the aliquot maintained in the presence of the compound, relative to that of the aliquot maintained in the absence of the compound, is an indication that the compound possesses such harmful potential.

In addition, there is further provided a method of inhibiting a cancer-related disease in a patient. This method comprises the steps of: a) obtaining a sample comprising cells from the patient; b) separately maintaining aliquots of the sample in the presence of a plurality of compositions; c) comparing expression of a marker in each of the aliquots; and d) administering to the patient at least one of the compositions which significantly alters the level of expression of the marker in the aliquot containing that composition, relative to the levels of expression of the marker in the presence of the other compositions.

The level of expression of a marker in a sample can be assessed, for example, by detecting the presence in the sample of: the corresponding marker protein or a fragment of the protein (e.g., by using a reagent, such as an antibody, an antibody derivative, an antibody fragment or single-chain antibody, which binds specifically with the protein or protein fragment) the corresponding marker nucleic acid (e.g., a nucleotide transcript, or a complement thereof), or a fragment of the nucleic acid (e.g., by contacting transcribed polynucleotides obtained from the sample with a substrate having affixed thereto one or more nucleic acids having the entire or a segment of the nucleic acid sequence or a complement thereof) a metabolite which is produced directly (i.e., catalyzed) or indirectly by the corresponding marker protein.

Any of the aforementioned methods may be performed using at least one (1) or a plurality (e.g., 2, 3, 5, or 10 or more) of cancer-related disease markers. In such methods, the level of expression of each of a plurality of markers, at least one of which is a marker, is compared with the normal level of expression of each of the plurality of markers in samples of the same type obtained from control humans not afflicted with a cancer-related disease. A significantly altered (i.e., increased or decreased as specified in the above-described methods using a single marker) level of expression in the sample of one or more markers, or some combination thereof, relative to that marker's corresponding normal or control level, is an indication that the patient is afflicted with a cancer-related disease. For all of the aforementioned methods, the marker(s) are selected such that the positive predictive value of the method is at least about 10%.

Examples of Candidate Agents

The candidate agents may be pharmacologic agents already known in the art or may be agents previously unknown to have any pharmacological activity. The agents may be naturally arising or designed in the laboratory. They may be isolated from microorganisms, animals or plants, or may be produced recombinantly, or synthesized by any suitable chemical method. They may be small molecules, nucleic acids, proteins, peptides or peptidomimetics. In certain embodiments, candidate agents are small organic compounds having a molecular weight of more than 50 and less than about 2,500 daltons. Candidate agents comprise functional groups necessary for structural interaction with proteins. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. There are, for example, numerous means available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. In certain embodiments, the candidate agents can be obtained using any of the numerous approaches in combinatorial library methods art, including, by non-limiting example: biological libraries; spatially addressable parallel solid phase or solution phase libraries; synthetic library methods requiring deconvolution; the "one-bead one-compound" library method; and synthetic library methods using affinity chromatography selection.

In certain further embodiments, certain pharmacological agents may be subjected to directed or random chemical modifications, such as acylation, alkylation, esterification, amidification, etc. to produce structural analogs.

The same methods for identifying therapeutic agents for treating a cancer-related disease can also be used to validate lead compounds/agents generated from in vitro studies.

The candidate agent may be an agent that up- or down-regulates one or more cancer-related disease response pathways. In certain embodiments, the candidate agent may be an antagonist that affects such pathway.

Methods for Treating a Cancer-Related Disease

There is provided herein methods for treating, inhibiting, relieving or reversing a cancer-related disease response. In the methods described herein, an agent that interferes with a signaling cascade is administered to an individual in need thereof, such as, but not limited to, cancer-related disease patients in whom such complications are not yet evident and those who already have at least one cancer-related disease response.

In the former instance, such treatment is useful to prevent the occurrence of such cancer-related disease response and/or reduce the extent to which they occur. In the latter instance, such treatment is useful to reduce the extent to which such cancer-related disease response occurs, prevent their further development or reverse the cancer-related disease response.

In certain embodiments, the agent that interferes with the cancer-related disease response cascade may be an antibody specific for such response.

Expression and/or Detection of Markers

Expression of a marker can be inhibited/enhanced in a number of ways, including, by way of a non-limiting example, an antisense oligonucleotide can be provided to the cancer-related disease cells in order to inhibit/enhance transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit/enhance the function or activity of the protein. The expression and/or function of a marker may also be inhibited/enhanced by treating the cancer-related disease cell with an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit/enhance expression of a marker or inhibit the function of a marker protein. The compound so identified can be provided to the patient in order to inhibit cancer-related disease cells of the patient.

Any marker or combination of markers, as well as any certain markers in combination with the markers, may be used in the compositions, kits and methods described herein. In general, it is desirable to use markers for which the difference between the level of expression of the marker in cancer-related disease cells and the level of expression of the same marker in normal cells is as great as possible. Although this difference can be as small as the limit of detection of the method for assessing expression of the marker, it is desirable that the difference be at least greater than the standard error of the assessment method, and, in certain embodiments, a difference of at least 0.5-, 1-, 2-, 3-, 4-, 5-, 6-, 7-, 8-, 9-, 10-, 15-, 20-, 100-, 500-, 1000-fold or greater than the level of expression of the same marker in normal tissue.

It is recognized that certain marker proteins are secreted to the extracellular space surrounding the cells. These markers are used in certain embodiments of the compositions, kits and methods, owing to the fact that such marker proteins can be detected in a cancer-associated body fluid sample, which may be more easily collected from a human patient than a tissue biopsy sample. In addition, in vivo techniques for detection of a marker protein include introducing into a subject a labeled antibody directed against the protein. For example, the antibody can be labeled with a radioactive marker whose presence and location in a subject can be detected by standard imaging techniques.

In order to determine whether any particular marker protein is a secreted protein, the marker protein is expressed in, for example, a mammalian cell, such as a human cell line, extracellular fluid is collected, and the presence or absence of the protein in the extracellular fluid is assessed (e.g. using a labeled antibody which binds specifically with the protein).

It will be appreciated that patient samples containing cells may be used in the methods described herein. In these embodiments, the level of expression of the marker can be assessed by assessing the amount (e.g., absolute amount or concentration) of the marker in a sample. The cell sample can, of course, be subjected to a variety of post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

The compositions, kits and methods can be used to detect expression of marker proteins having at least one portion which is displayed on the surface of cells which express it. For example, immunological methods may be used to detect such proteins on whole cells, or computer-based sequence analysis methods may be used to predict the presence of at least one extracellular domain (i.e., including both secreted proteins and proteins having at least one cell-surface domain). Expression of a marker protein having at least one portion which is displayed on the surface of a cell which expresses it may be detected without necessarily lysing the cell (e.g., using a labeled antibody which binds specifically with a cell-surface domain of the protein).

Expression of a marker may be assessed by any of a wide variety of methods for detecting expression of a transcribed nucleic acid or protein. Non-limiting examples of such methods include immunological methods for detection of secreted, cell-surface, cytoplasmic or nuclear proteins, protein purification methods, protein function or activity assays, nucleic acid hybridization methods, nucleic acid reverse transcription methods and nucleic acid amplification methods.

In a particular embodiment, expression of a marker is assessed using an antibody (e.g., a radio-labeled, chromophore-labeled, fluorophore-labeled or enzyme-labeled antibody), an antibody derivative (e.g., an antibody conjugated with a substrate or with the protein or ligand of a protein-ligand pair), or an antibody fragment (e.g., a single-chain antibody, an isolated antibody hypervariable domain, etc.) which binds specifically with a marker protein or fragment thereof, including a marker protein which has undergone all or a portion of its normal post-translational modification.

In another particular embodiment, expression of a marker is assessed by preparing mRNA/cDNA (i.e., a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many methods of detecting mutations or variants (e.g., single nucleotide polymorphisms, deletions, etc.) of a marker may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g., at least 7, 10, 15, 20, 25, 30, 40, 50, 100, 500, or more nucleotide residues) of a marker nucleic acid. If polynucleotides complementary to or homologous with are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). When a method of assessing marker expression is used which involves hybridization of one nucleic acid with another, it is desired that the hybridization be performed under stringent hybridization conditions.

Biomarker Assays

In certain embodiments, the biomarker assays can be performed using mass spectrometry or surface plasmon resonance. In various embodiment, the method of identifying an agent active against a cancer-related disease can include a) providing a sample of cells containing one or more markers or derivative thereof; b) preparing an extract from the cells; c) mixing the extract with a labeled nucleic acid probe containing a marker binding site; and, d) determining the formation of a complex between the marker and the nucleic acid probe in the presence or absence of the test agent. The determining step can include subjecting the extract/nucleic acid probe mixture to an electrophoretic mobility shift assay.

In certain embodiments, the determining step comprises an assay selected from an enzyme linked immunoabsorption assay (ELISA), fluorescence based assays and ultra high throughput assays, for example surface plasmon resonance (SPR) or fluorescence correlation spectroscopy (FCS) assays. In such embodiments, the SPR sensor is useful for direct real-time observation of biomolecular interactions since SPR is sensitive to minute refractive index changes at a metal-dielectric surface. SPR is a surface technique that is sensitive to changes of $10^5$ to $10^{-6}$ refractive index (RI) units within approximately 200 nm of the SPR sensor/sample interface. Thus, SPR spectroscopy is useful for monitoring the growth of thin organic films deposited on the sensing layer.

Because the compositions, kits, and methods rely on detection of a difference in expression levels of one or more markers, it is desired that the level of expression of the marker is significantly greater than the minimum detection limit of the method used to assess expression in at least one of normal cells and cancer-affected cells.

It is understood that by routine screening of additional patient samples using one or more of the markers, it will be realized that certain of the markers are under- or over-expressed in cells of various types, including specific cancer-related diseases.

In addition, as a greater number of patient samples are assessed for expression of the markers and the outcomes of the individual patients from whom the samples were obtained are correlated, it will also be confirmed that altered expression of certain of the markers are strongly correlated with a cancer-related disease and that altered expression of other markers are strongly correlated with other diseases. The compositions, kits, and methods are thus useful for characterizing one or more of the stage, grade, histological type, and nature of a cancer-related disease in patients.

When the compositions, kits, and methods are used for characterizing one or more of the stage, grade, histological type, and nature of a cancer-related disease in a patient, it is desired that the marker or panel of markers is selected such that a positive result is obtained in at least about 20%, and in certain embodiments, at least about 40%, 60%, or 80%, and in substantially all patients afflicted with a cancer-related disease of the corresponding stage, grade, histological type, or nature. The marker or panel of markers can be selected such that a positive predictive value of greater than about 10% is obtained for the general population (in a non-limiting example, coupled with an assay specificity greater than 80%).

When a plurality of markers are used in the compositions, kits, and methods, the level of expression of each marker in a patient sample can be compared with the normal level of expression of each of the plurality of markers in non-cancer samples of the same type, either in a single reaction mixture (i.e. using reagents, such as different fluorescent probes, for each marker) or in individual reaction mixtures corresponding to one or more of the markers. In one embodiment, a significantly altered level of expression of more than one of the plurality of markers in the sample, relative to the corresponding normal levels, is an indication that the patient is afflicted with a cancer-related disease. When a plurality of markers is used, 2, 3, 4, 5, 8, 10, 12, 15, 20, 30, or 50 or more individual markers can be used; in certain embodiments, the use of fewer markers may be desired.

In order to maximize the sensitivity of the compositions, kits, and methods (i.e., by interference attributable to cells of non-tissue and/or fluid origin in a patient sample), it is desirable that the marker used therein be a marker which has a restricted tissue distribution, e.g., normally not expressed in a non-tissue cells.

It is recognized that the compositions, kits, and methods will be of particular utility to patients having an enhanced risk of developing a cancer-related disease and their medical advisors. Patients recognized as having an enhanced risk of developing a cancer-related disease include, for example, patients having a familial history of a cancer-related disease.

The level of expression of a marker in normal human cells can be assessed in a variety of ways. In one embodiment, this normal level of expression is assessed by assessing the level of expression of the marker in a portion of cells which appear to be normal and by comparing this normal level of expression with the level of expression in a portion of the cells which is suspected of being abnormal. Alternately, and particularly as further information becomes available as a result of routine performance of the methods described herein, population-average values for normal expression of the markers may be used. In other embodiments, the "normal" level of expression of a marker may be determined by assessing expression of the marker in a patient sample obtained from a non-cancer-afflicted patient, from a patient sample obtained from a patient before the suspected onset of a cancer-related disease in the patient, from archived patient samples, and the like.

There is also provided herein compositions, kits, and methods for assessing the presence of cancer-related disease cells in a sample (e.g., an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions, in the kits, or the methods used to assess levels of marker expression in the sample.

Methods of Producing Antibodies

There is also provided herein a method of making an isolated hybridoma which produces an antibody useful for assessing whether a patient is afflicted with a cancer-related disease. In this method, a protein or peptide comprising the entirety or a segment of a marker protein is synthesized or isolated (e.g., by purification from a cell in which it is expressed or by transcription and translation of a nucleic acid encoding the protein or peptide in vivo or in vitro). A vertebrate, for example, a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods. Hybridomas formed in this manner are then screened using standard methods to identify one or more hybridomas which produce an antibody which specifically binds with the marker protein or a fragment thereof. There is also provided herein hybridomas made by this method and antibodies made using such hybridomas.

Methods of Assessing Efficacy

There is also provided herein a method of assessing the efficacy of a test compound for inhibiting cancer-related disease cells. As described herein, differences in the level of expression of the markers correlate with the abnormal state of the cells. Although it is recognized that changes in the levels of expression of certain of the markers likely result from the abnormal state of the cells, it is likewise recognized that changes in the levels of expression of other of the markers induce, maintain, and promote the abnormal state of those cells. Thus, compounds which inhibit a cancer-related disease in a patient will cause the level of expression of one or more of the markers to change to a level nearer the normal level of expression for that marker (i.e., the level of expression for the marker in normal cells).

This method thus comprises comparing expression of a marker in a first cell sample and maintained in the presence of the test compound and expression of the marker in a second cell sample and maintained in the absence of the test compound. A significantly altered expression of a marker in the presence of the test compound is an indication that the test compound inhibits a cancer-related disease. The cell samples may, for example, be aliquots of a single sample of normal cells obtained from a patient, pooled samples of normal cells obtained from a patient, cells of a normal cell line, aliquots of a single sample of cancer-related disease cells obtained from a patient, pooled samples of cancer-related disease cells obtained from a patient, cells of a cancer-related disease cell line, or the like.

In one embodiment, the samples are cancer-related disease cells obtained from a patient and a plurality of compounds believed to be effective for inhibiting various cancer-related diseases are tested in order to identify the compound which is likely to best inhibit the cancer-related disease in the patient.

This method may likewise be used to assess the efficacy of a therapy for inhibiting a cancer-related disease in a patient. In this method, the level of expression of one or more markers in a pair of samples (one subjected to the therapy, the other not subjected to the therapy) is assessed. As with the method of assessing the efficacy of test compounds, if the therapy induces a significantly altered level of expression of a marker then the therapy is efficacious for inhibiting a cancer-related disease. As above, if samples from a selected patient are used in this method, then alternative therapies can be assessed in vitro in order to select a therapy most likely to be efficacious for inhibiting a cancer-related disease in the patient.

Methods for Assessing Harmful Potentials

As described herein, the abnormal state of human cells is correlated with changes in the levels of expression of the markers. There is also provided a method for assessing the harmful potential of a test compound. This method comprises maintaining separate aliquots of human cells in the presence and absence of the test compound. Expression of a marker in each of the aliquots is compared. A significantly altered level of expression of a marker in the aliquot maintained in the presence of the test compound (relative to the aliquot maintained in the absence of the test compound) is an indication that the test compound possesses a harmful potential. The relative harmful potential of various test compounds can be assessed by comparing the degree of enhancement or inhibition of the level of expression of the relevant markers, by comparing the number of markers for which the level of expression is enhanced or inhibited, or by comparing both.

Isolated Proteins and Antibodies

One aspect pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein").

When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein. In certain embodiments, useful proteins are substantially identical (e.g., at least about 40%, and in certain embodiments, 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

In addition, libraries of segments of a marker protein can be used to generate a variegated population of polypeptides for screening and subsequent selection of variant marker proteins or segments thereof.

Predictive Medicine

There is also provided herein uses of the animal models and markers in the field of predictive medicine in which diagnostic assays, prognostic assays, pharmacogenomics, and monitoring clinical trials are used for prognostic (predictive) purposes to thereby treat an individual prophylactically. Accordingly, there is also provided herein diagnostic assays for determining the level of expression of one or more marker proteins or nucleic acids, in order to determine whether an individual is at risk of developing a cancer-related disease. Such assays can be used for prognostic or predictive purposes to thereby prophylactically treat an individual prior to the onset of the cancer-related disease.

In another aspect, the methods are useful for at least periodic screening of the same individual to see if that individual has been exposed to chemicals or toxins that change his/her expression patterns.

Yet another aspect pertains to monitoring the influence of agents (e.g., drugs or other compounds administered either to inhibit a cancer-related disease or to treat or prevent any other disorder (e.g., in order to understand any system effects that such treatment may have) on the expression or activity of a marker in clinical trials.

Pharmacogenomics

The markers are also useful as pharmacogenomic markers. As used herein, a "pharmacogenomic marker" is an objective biochemical marker whose expression level correlates with a specific clinical drug response or susceptibility in a patient. The presence or quantity of the pharmacogenomic marker expression is related to the predicted response of the patient and more particularly the patient's tumor to therapy with a specific drug or class of drugs. By assessing the presence or quantity of the expression of one or more pharmacogenomic markers in a patient, a drug therapy which is most appropriate for the patient, or which is predicted to have a greater degree of success, may be selected.

Monitoring Clinical Trials

Monitoring the influence of agents (e.g., drug compounds) on the level of expression of a marker can be applied not only in basic drug screening, but also in clinical trials. For example, the effectiveness of an agent to affect marker expression can be monitored in clinical trials of subjects receiving treatment for a cancer-related disease.

In one non-limiting embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly.

For example, increased expression of the marker gene(s) during the course of treatment may indicate ineffective dosage and the desirability of increasing the dosage. Conversely, decreased expression of the marker gene(s) may indicate efficacious treatment and no need to change dosage.

Electronic Apparatus Readable Media, Systems, Arrays and Methods of Using Same

As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; and general hard disks and hybrids of these categories such as magnetic/optical storage media. The medium is adapted or configured for having recorded thereon a marker as described herein.

As used herein, the term "electronic apparatus" is intended to include any suitable computing or processing apparatus or other device configured or adapted for storing data or information. Examples of electronic apparatus suitable for use with embodiments of the present invention include stand-alone computing apparatus; networks, including a local area network (LAN), a wide area network (WAN) Internet, Intranet, and Extranet; electronic appliances such as personal digital assistants (PDAs), cellular phone, pager and the like; and local and distributed processing systems.

As used herein, "recorded" refers to a process for storing or encoding information on the electronic apparatus readable medium. Those skilled in the art can readily adopt any method for recording information on media to generate materials comprising the markers described herein.

A variety of software programs and formats can be used to store the marker information of embodiments of the present invention on the electronic apparatus readable medium. Any number of data processor structuring formats (e.g., text file or database) may be employed in order to obtain or create a medium having recorded thereon the markers. By providing the markers in readable form, one can routinely access the marker sequence information for a variety of purposes. For example, one skilled in the art can use the nucleotide or amino acid sequences in readable form to compare a target sequence or target structural motif with the sequence information stored within the data storage means. Search means are used to identify fragments or regions of the sequences which match a particular target sequence or target motif.

Thus, there is also provided herein a medium for holding instructions for performing a method for determining whether a subject has a cancer-related disease or a pre-disposition to a cancer-related disease, wherein the method comprises the steps of determining the presence or absence of a marker and based on the presence or absence of the marker, determining whether the subject has a cancer-related disease or a pre-disposition to a cancer-related disease and/or recommending a particular treatment for a cancer-related disease or pre-cancer-related disease condition. It is contemplated that different entities may perform steps of the contemplated methods and that one or more means for electronic communication may be employed to store and transmit the data. It is contemplated that raw data, processed data, diagnosis, and/or prognosis would be communicated between entities which may include one or more of: a primary care physician, patient, specialist, insurance provider, foundation, hospital, database, counselor, therapist, pharmacist, and government.

There is also provided herein an electronic system and/or in a network, a method for determining whether a subject has a cancer-related disease or a pre-disposition to a cancer-related disease associated with a marker wherein the method comprises the steps of determining the presence or absence of the marker, and based on the presence or absence of the marker, determining whether the subject has a cancer-related disease or a pre-disposition to a cancer-related disease, and/or recommending a particular treatment for the cancer-related disease or pre-cancer-related disease condition. The method may further comprise the step of receiving phenotypic information associated with the subject and/or acquiring from a network phenotypic information associated with the subject.

Also provided herein is a network, a method for determining whether a subject has a cancer-related disease or a pre-disposition to a cancer-related disease associated with a marker, the method comprising the steps of receiving information associated with the marker, receiving phenotypic information associated with the subject, acquiring information from the network corresponding to the marker and/or a cancer-related disease, and based on one or more of the phenotypic information, the marker, and the acquired information, determining whether the subject has a cancer-related disease or a pre-disposition to a cancer-related disease. The method may further comprise the step of recommending a particular treatment for the cancer-related disease or pre-cancer-related disease condition.

There is also provided herein a business method for determining whether a subject has a cancer-related disease or a pre-disposition to a cancer-related disease, the method comprising the steps of receiving information associated with the marker, receiving phenotypic information associated with the subject, acquiring information from the network corresponding to the marker and/or a cancer-related disease, and based on one or more of the phenotypic information, the marker, and the acquired information, determining whether the subject has a cancer-related disease or a pre-disposition to a cancer-related disease. The method may further comprise the step of recommending a particular treatment for the cancer-related disease or pre-cancer-related disease condition.

Arrays

There is also provided herein an array that can be used to assay expression of one or more genes in the array. In one embodiment, the array can be used to assay gene expression in a tissue to ascertain tissue specificity of genes in the array. In this manner, up to about 7000 or more genes can be simultaneously assayed for expression. This allows a profile to be developed showing a battery of genes specifically expressed in one or more tissues.

In addition to such qualitative determination, there is provided herein the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined.

Such a determination is useful, for example, to know the effect of cell-cell interaction at the level of gene expression. If an agent is administered therapeutically to treat one cell type but has an undesirable effect on another cell type, the method provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a cancer-related disease, progression of a cancer-related disease, and processes, such as cellular transformation associated with a cancer-related disease.

The array is also useful for ascertaining the effect of the expression of a gene or the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that can serve as a molecular target for diagnosis or therapeutic intervention.

Surrogate Markers

The markers may serve as surrogate markers for one or more disorders or disease states or for conditions leading up to a cancer-related disease state. As used herein, a "surrogate marker" is an objective biochemical marker which correlates with the absence or presence of a disease or disorder, or with the progression of a disease or disorder. The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies, or when an assessment of disease progression is desired before a potentially dangerous clinical endpoint is reached.

Pharmacodynamic Markers

The markers are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo.

Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations.

Protocols for Testing

The method of testing for cancer-related diseases comprises, for example measuring the expression level of each marker gene in a biological sample from a subject over time and comparing the level with that of the marker gene in a control biological sample.

When the marker gene is one of the genes described herein and the expression level is differentially expressed (for examples, higher or lower than that in the control), the subject is judged to be affected with a cancer-related disease. When the expression level of the marker gene falls within the permissible range, the subject is unlikely to be affected with a cancer-related disease.

The standard value for the control may be pre-determined by measuring the expression level of the marker gene in the control, in order to compare the expression levels. For example, the standard value can be determined based on the expression level of the above-mentioned marker gene in the control. For example, in certain embodiments, the permissible range is taken as ±2S.D. based on the standard value. Once the standard value is determined, the testing method may be performed by measuring only the expression level in a biological sample from a subject and comparing the value with the determined standard value for the control.

Expression levels of marker genes include transcription of the marker genes to mRNA, and translation into proteins. Therefore, one method of testing for a cancer-related disease is performed based on a comparison of the intensity of expression of mRNA corresponding to the marker genes, or the expression level of proteins encoded by the marker genes.

Probes

The measurement of the expression levels of marker genes in the testing for a cancer-related disease can be carried out according to various gene analysis methods. Specifically, one can use, for example, a hybridization technique using nucleic acids that hybridize to these genes as probes, or a gene amplification technique using DNA that hybridize to the marker genes as primers.

The probes or primers used for the testing can be designed based on the nucleotide sequences of the marker genes. The identification numbers for the nucleotide sequences of the respective marker genes are described herein.

Further, it is to be understood that genes of higher animals generally accompany polymorphism in a high frequency. There are also many molecules that produce isoforms comprising mutually different amino acid sequences during the splicing process. Any gene associated with a cancer-related disease that has an activity similar to that of a marker gene is included in the marker genes, even if it has nucleotide sequence differences due to polymorphism or being an isoform.

It is also to be understood that the marker genes can include homologs of other species in addition to humans. Thus, unless otherwise specified, the expression "marker gene" refers to a homolog of the marker gene unique to the species or a foreign marker gene which has been introduced into an individual.

Also, it is to be understood that a "homolog of a marker gene" refers to a gene derived from a species other than a human, which can hybridize to the human marker gene as a probe under stringent conditions. Such stringent conditions are known to one skilled in the art who can select an appropriate condition to produce an equal stringency experimentally or empirically.

A polynucleotide comprising the nucleotide sequence of a marker gene or a nucleotide sequence that is complementary to the complementary strand of the nucleotide sequence of a marker gene and has at least 15 nucleotides, can be used as a primer or probe. Thus, a "complementary strand" means one strand of a double stranded DNA with respect to the other strand and which is composed of A:T (U for RNA) and G:C base pairs.

In addition, "complementary" means not only those that are completely complementary to a region of at least 15 continuous nucleotides, but also those that have a nucleotide sequence homology of at least 40% in certain instances, 50% in certain instances, 60% in certain instances, 70% in certain instances, at least 80%, 90%, and 95% or higher. The degree of homology between nucleotide sequences can be determined by an algorithm, BLAST, etc.

Such polynucleotides are useful as a probe to detect a marker gene, or as a primer to amplify a marker gene. When used as a primer, the polynucleotide comprises usually 15 bp to 100 bp, and in certain embodiments 15 bp to 35 bp of nucleotides. When used as a probe, a DNA comprises the whole nucleotide sequence of the marker gene (or the complementary strand thereof), or a partial sequence thereof that has at least 15 bp nucleotides. When used as a primer, the 3' region must be complementary to the marker gene, while the 5' region can be linked to a restriction enzyme-recognition sequence or a tag.

"Polynucleotides" may be either DNA or RNA. These polynucleotides may be either synthetic or naturally-occurring. Also, DNA used as a probe for hybridization is usually labeled. Those skilled in the art readily understand such labeling methods. Herein, the term "oligonucleotide" means a polynucleotide with a relatively low degree of polymerization. Oligonucleotides are included in polynucleotides.

Tests for Cancer-Related Diseases

Tests for a cancer-related disease using hybridization techniques can be performed using, for example, Northern hybridization, dot blot hybridization, or the DNA microarray technique. Furthermore, gene amplification techniques, such as the RT-PCR method may be used. By using the PCR amplification monitoring method during the gene amplification step in RT-PCR, one can achieve a more quantitative analysis of the expression of a marker gene.

In the PCR gene amplification monitoring method, the detection target (DNA or reverse transcript of RNA) is hybridized to probes that are labeled with a fluorescent dye and a quencher which absorbs the fluorescence. When the PCR proceeds and Taq polymerase degrades the probe with its 5'-3' exonuclease activity, the fluorescent dye and the quencher draw away from each other and the fluorescence is detected. The fluorescence is detected in real time. By simultaneously measuring a standard sample in which the copy number of a target is known, it is possible to determine the copy number of the target in the subject sample with the cycle number where PCR amplification is linear. Also, one skilled in the art recognizes that the PCR amplification monitoring method can be carried out using any suitable method.

The method of testing for a cancer-related disease can be also carried out by detecting a protein encoded by a marker gene. Hereinafter, a protein encoded by a marker gene is described as a "marker protein." For such test methods, for example, the Western blotting method, the immunoprecipitation method, and the ELISA method may be employed using an antibody that binds to each marker protein.

Antibodies used in the detection that bind to the marker protein may be produced by any suitable technique. Also, in order to detect a marker protein, such an antibody may be appropriately labeled. Alternatively, instead of labeling the antibody, a substance that specifically binds to the antibody, for example, protein A or protein G, may be labeled to detect the marker protein indirectly. More specifically, such a detection method can include the ELISA method.

A protein or a partial peptide thereof used as an antigen may be obtained, for example, by inserting a marker gene or a portion thereof into an expression vector, introducing the construct into an appropriate host cell to produce a transformant, culturing the transformant to express the recombinant protein, and purifying the expressed recombinant protein from the culture or the culture supernatant. Alternatively, the amino acid sequence encoded by a gene or an oligopeptide comprising a portion of the amino acid sequence encoded by a full-length cDNA are chemically synthesized to be used as an immunogen.

Furthermore, a test for a cancer-related disease can be performed using as an index not only the expression level of a marker gene but also the activity of a marker protein in a biological sample. Activity of a marker protein means the biological activity intrinsic to the protein. Various methods can be used for measuring the activity of each protein.

Even if a patient is not diagnosed as being affected with a cancer-related disease in a routine test in spite of symptoms suggesting these diseases, whether or not such a patient is suffering from a cancer-related disease can be easily determined by performing a test according to the methods described herein.

More specifically, in certain embodiments, when the marker gene is one of the genes described herein, an increase or decrease in the expression level of the marker gene in a patient whose symptoms suggest at least a susceptibility to a cancer-related disease indicates that the symptoms are primarily caused by a cancer-related disease.

In addition, the tests are useful to determine whether a cancer-related disease is improving in a patient. In other words, the methods described herein can be used to judge the therapeutic effect of a treatment for a cancer-related disease. Furthermore, when the marker gene is one of the genes described herein, an increase or decrease in the expression level of the marker gene in a patient, who has been diagnosed as being affected by a cancer-related disease, implies that the disease has progressed more.

The severity and/or susceptibility to a cancer-related disease may also be determined based on the difference in expression levels. For example, when the marker gene is one of the genes described herein, the degree of increase in the expression level of the marker gene is correlated with the presence and/or severity of a cancer-related disease.

Control of Expression of Marker

In addition, the expression itself of a marker gene can be controlled by introducing a mutation(s) into the transcriptional regulatory region of the gene. Those skilled in the art understand such amino acid substitutions. Also, the number of amino acids that are mutated is not particularly restricted, as long as the activity is maintained. Normally, it is within 50 amino acids, in certain non-limiting embodiments, within 30 amino acids, within 10 amino acids, or within 3 amino acids. The site of mutation may be any site, as long as the activity is maintained.

Screening Methods

In yet another aspect, there is provided herein screening methods for candidate compounds for therapeutic agents to treat a cancer-related disease. One or more marker genes are selected from the group of genes described herein. A therapeutic agent for a cancer-related disease can be obtained by selecting a compound capable of increasing or decreasing the expression level of the marker gene(s).

It is to be understood that the expression "a compound that increases the expression level of a gene" refers to a compound that promotes any one of the steps of gene transcription, gene translation, or expression of a protein activity. On the other hand, the expression "a compound that decreases the expression level of a gene", as used herein, refers to a compound that inhibits any one of these steps.

In particular aspects, the method of screening for a therapeutic agent for a cancer-related disease can be carried out either in vivo or in vitro. This screening method can be performed, for example, by (1) administering a candidate compound to an animal subject; (2) measuring the expression level of a marker gene(s) in a biological sample from the animal subject; or (3) selecting a compound that increases or decreases the expression level of a marker gene(s) as compared to that in a control with which the candidate compound has not been contacted.

In still another aspect, there is provided herein a method to assess the efficacy of a candidate compound for a pharmaceutical agent on the expression level of a marker gene(s) by contacting an animal subject with the candidate compound and monitoring the effect of the compound on the expression level of the marker gene(s) in a biological sample derived from the animal subject. The variation in the expression level of the marker gene(s) in a biological sample derived from the animal subject can be monitored using the same technique as used in the testing method described above. Furthermore, based on the evaluation, a candidate compound for a pharmaceutical agent can be selected by screening.

Kits

Any of the compositions described herein may be comprised in a kit. In a non-limiting example, reagents for isolating miRNA, labeling miRNA, and/or evaluating an miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of the sequences herein.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being one preferred solution. Other solutions that may be included in a kit are those solutions involved in isolating and/or enriching miRNA from a mixed sample.

However, the components of the kit may be provided as dried powder(s). When reagents and/or components are provided as a dry powder, the powder can be reconstituted by the addition of a suitable solvent. It is envisioned that the solvent may also be provided in another container means. The kits may also include components that facilitate isolation of the labeled miRNA. It may also include components that preserve or maintain the miRNA or that protect against its degradation. The components may be RNAse-free or protect against RNAses.

Also, the kits can generally comprise, in suitable means, distinct containers for each individual reagent or solution. The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any embodiment discussed in the context of an miRNA array may be employed more generally in screening or profiling methods or kits of the invention. In other words, any embodiments describing what may be included in a particular array can be practiced in the context of miRNA profiling more generally and need not involve an array per se.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits for using miRNA arrays for therapeutic, prognostic, or diagnostic applications and such uses are contemplated. The kits can include a miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis.

In another aspect, there is provided various diagnostic and test kits. In one embodiment, a kit is useful for assessing whether a patient is afflicted with a cancer-related disease. The kit comprises a reagent for assessing expression of a marker. In another embodiment, a kit is useful for assessing the suitability of a chemical or biologic agent for inhibiting a cancer-related disease in a patient. Such a kit comprises a reagent for assessing expression of a marker, and may also comprise one or more of such agents.

In a further embodiment, the kits are useful for assessing the presence of cancer-related disease cells or treating cancer-related diseases. Such kits comprise an antibody, an antibody derivative or an antibody fragment, which binds specifically with a marker protein or a fragment of the protein. Such kits may also comprise a plurality of antibodies, antibody derivatives or antibody fragments wherein the plurality of such antibody agents binds specifically with a marker protein or a fragment of the protein.

In an additional embodiment, the kits are useful for assessing the presence of cancer-related disease cells, wherein the kit comprises a nucleic acid probe that binds specifically with a marker nucleic acid or a fragment of the nucleic acid. The kit may also comprise a plurality of probes, wherein each of the probes binds specifically with a marker nucleic acid, or a fragment of the nucleic acid.

The compositions, kits and methods described herein can have the following uses, among others: 1) assessing whether a patient is afflicted with a cancer-related disease; 2) assessing the stage of a cancer-related disease in a human patient; 3) assessing the grade of a cancer-related disease in a patient; 4) assessing the nature of a cancer-related disease in a patient; 5) assessing the potential to develop a cancer-related disease in a patient; 6) assessing the histological type of cells associated with a cancer-related disease in a patient; 7) making antibodies, antibody fragments or antibody derivatives that are useful for treating a cancer-related disease and/or assessing whether a patient is afflicted with a cancer-related disease; 8) assessing the presence of cancer-related disease cells; 9) assessing the efficacy of one or more test compounds for inhibiting a cancer-related disease in a patient; 10) assessing the efficacy of a therapy for inhibiting a cancer-related disease in a patient; 11) monitoring the progression of a cancer-related disease in a patient; 12) selecting a composition or therapy for inhibiting a cancer-related disease in a patient; 13) treating a patient afflicted with a cancer-related disease; 14) inhibiting a cancer-related disease in a patient; 15) assessing the harmful potential of a test compound; and 16) preventing the onset of a cancer-related disease in a patient at risk for developing a cancer-related disease.

The kits are useful for assessing the presence of cancer-related disease cells (e.g. in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an MRNA, a spliced MRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kits may optionally comprise additional components useful for performing the methods described herein. By way of example, the kit may comprise fluids (e.g. SSC buffer) suitable for annealing complementary nucleic acids or for binding an antibody with a protein with which it specifically binds, one or more sample compartments, an instructional material which describes performance of the method, a sample of normal cells, a sample of cancer-related disease cells, and the like.

The methods and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Animal Model

Non-human animal model can be produced for assessment of at least one cancer-related disease. The method includes exposing the animal to repeated doses of at least one chemical believed to cause the cancer if interest. In certain aspects, the method further includes collecting one or more selected samples from the animal; and comparing the collected sample to one or more indicia of potential cancer initiation or development.

A method of producing the animal model includes: maintaining the animal in a specific chemical-free environment and sensitizing the animal with at least one chemical believed to cause the cancer. In certain embodiments, at least a part of the animal is sensitized by multiple sequential exposures.

A method of screening for an agent for effectiveness against at least one cancer-related disease generally includes: administering at least one agent to a test animal, determining whether the agent reduces or aggravates one or more symptoms of the cancer-related disease; correlating a reduction in one or more symptoms with effectiveness of the agent against the cancer-related disease; or correlating a lack of reduction in one or more symptoms with ineffectiveness of the agent. The animal model is useful for assessing one or more metabolic pathways that contribute to at least one of initiation, progression, severity, pathology, aggressiveness, grade, activity, disability, mortality, morbidity, disease sub-classification or other underlying pathogenic or pathological feature of at least one cancer-related disease. The analysis can be by one or more of: hierarchical clustering, signature network construction, mass spectroscopy proteomic analysis, surface plasmon resonance, linear statistical modeling, partial least squares discriminant analysis, and multiple linear regression analysis.

The animal model can be assessed for at least one cancer-related disease, by examining an expression level of one or more markers, or a functional equivalent thereto.

The animal models can be used for the screening of therapeutic agents useful for treating or preventing a cancer-related disease. Accordingly, the methods are useful for identifying therapeutic agents for treating or preventing a cancer-related disease. The methods comprise administering a candidate agent to an animal model made by the methods described herein, assessing at least one cancer-related disease response in the animal model as compared to a control animal model to which the candidate agent has not been administered. If at least one cancer-related disease response is reduced in symptoms or delayed in onset, the candidate agent is an agent for treating or preventing the cancer-related disease.

The animal models for a cancer-related disease can include an animal where the expression level of one or more marker genes or a gene functionally equivalent to the marker gene has been elevated in the animal model. A "functionally equivalent gene" as used herein generally is a gene that encodes a protein having an activity similar to a known activity of a protein encoded by the marker gene. A representative example of a functionally equivalent gene includes a counterpart of a marker gene of a subject animal, which is intrinsic to the animal.

The animal model for a cancer-related disease is useful for detecting physiological changes due to a cancer-related disease. In certain embodiments, the animal model is useful to reveal additional functions of marker genes and to evaluate drugs whose targets are the marker genes.

In one embodiment, an animal model for a cancer-related disease can be created by controlling the expression level of a counterpart gene or administering a counterpart gene. The method can include creating an animal model for a cancer-related disease by controlling the expression level of a gene selected from the group of genes described herein. In another embodiment, the method can include creating an animal model for a cancer-related disease by administering the protein encoded by a gene described herein, or administering an antibody against the protein. It is to be also understood, that in certain other embodiments, the marker can be over-expressed such that the marker can then be measured using appropriate methods.

In another embodiment, an animal model for a cancer-related disease can be created by introducing a gene selected from such groups of genes, or by administering a protein encoded by such a gene.

In another embodiment, a cancer-related disease can be induced by suppressing the expression of a gene selected from such groups of genes or the activity of a protein encoded by such a gene. An antisense nucleic acid, a ribozyme, or an RNAi can be used to suppress the expression. The activity of a protein can be controlled effectively by administering a substance that inhibits the activity, such as an antibody.

The animal model is useful to elucidate the mechanism underlying a cancer-related disease and also to test the safety of compounds obtained by screening. For example, when an animal model develops the symptoms of a cancer-related disease, or when a measured value involved in a certain a cancer-related disease alters in the animal, a screening system can be constructed to explore compounds having activity to alleviate the disease.

As used herein, the expression "an increase in the expression level" refers to any one of the following: where a marker gene introduced as a foreign gene is expressed artificially; where the transcription of a marker gene intrinsic to the subject animal and the translation thereof into the protein are enhanced; or where the hydrolysis of the protein, which is the translation product, is suppressed. As used herein, the expression "a decrease in the expression level" refers to either the state in which the transcription of a marker gene of the subject animal and the translation thereof into the protein are inhibited, or the state in which the hydrolysis of the protein, which is the translation product, is enhanced. The expression level of a gene can be determined, for example, by a difference in signal intensity on a DNA chip. Furthermore, the activity of the translation product—the protein—can be determined by comparing with that in the normal state.

It is also within the contemplated scope that the animal model can include transgenic animals, including, for example animals where a marker gene has been introduced and expressed artificially; marker gene knockout animals; and knock-in animals in which another gene has been substituted for a marker gene. A transgenic animal, into which an antisense nucleic acid of a marker gene, a ribozyme, a polynucleotide having an RNAi effect, or a DNA functioning as a decoy nucleic acid or such has been introduced, can be used as the transgenic animal. Such transgenic animals also include, for example, animals in which the activity of a marker protein has been enhanced or suppressed by introducing a mutation(s) into the coding region of the gene, or the amino acid sequence has been modified to become resistant or susceptible to hydrolysis. Mutations in an amino acid sequence include substitutions, deletions, insertions, and additions.

In view of the many possible embodiments to which the principles of the inventors' invention may be applied, it should be recognized that the illustrated embodiments are only preferred examples of the invention and should not be taken as a limitation on the scope of the invention. Rather, the scope of the invention is defined by the following claims. The inventors therefore claim as the inventors' invention all that comes within the scope and spirit of these claims.

The publication and other material used herein to illuminate the invention or provide additional details respecting the practice of the invention, are incorporated by reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents

What is claimed is:

1. A method of determining whether a human subject has a poor survival prognosis for breast cancer (BC), comprising:
   extracting a test sample of tissue from a human subject, wherein the extracting is by hypodermic needle, microdissection, or laser capture;
   measuring by microarray analysis the level of a miRNA/mRNA signature in the test sample of tissue from the human subject, the miRNA/mRNA signature consisting of: i) miRNA gene products consisting of the group of: hsa-miR-103, hsa-miR-1307, hsa-miR-148b, hsa-miR-324, hsa-miR-326, hsa-miR-328, hsa-miR-365, hsa-miR-484, hsa-miR-874a, and hsa-miR-93; and, ii) mRNA gene products consisting of the group of: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7, and ZFC3H1; and,
   determining the survival prognosis of the subject; wherein an alteration in the levels of the miRNA and mRNA gene products in the test sample, relative to the level of corresponding miRNA and mRNA gene products in a control sample of cancer-free tissue, is indicative of the human subject having a poor survival prognosis for BC.

2. A method for determining if a human subject having breast cancer (BC) has a poor survival outcome comprising:
   extracting breast cells from a human subject, wherein the extracting is by hypodermic needle, microdissection, or laser capture;
   assaying by microarray analysis a nucleic acid sample obtained from the breast cells of the human subject to determine the expression level of a miRNA/mRNA signature in the nucleic acid sample,
   the miRNA/mRNA signature consisting of: i) miRNA gene products consisting of the group of: hsa-miR-103, hsa-miR-1307, hsa-miR-148b, hsa-miR-324, hsa-miR-326, hsa-miR-328, hsa-miR-365, hsa-miR-484, hsa-miR-874a, and hsa-miR-93; and, ii) mRNA gene products consisting of the group of: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7, and ZFC3H1; and,
   determining that the human subject has a poor survival outcome, if there is an alteration in the expression levels of miRNA/mRNA signature in the nucleic acid sample, as compared to a control sample.

3. A method for predicting a prognosis in a breast cancer patient comprising:
   extracting a biological test sample from a subject having breast cancer, wherein the extracting is by hypodermic needle, microdissection, or laser capture;
   detecting by microarray analysis a test expression level of a signature in the biological test sample from the subject having breast cancer; assigning a risk score to the test expression level; and predicting a poor prognosis when the test expression level is assigned a high risk score; and predicting a good prognosis when the test expression level is assigned a low risk score, wherein the signature comprises a miRNA/mRNA signature consisting of: i) miRNA gene products consisting of the group of: hsa-miR-103, hsa-miR-1307, hsa-miR-148b, hsa-miR-324, hsa-miR-326, hsa-miR-328, hsa-miR-365, hsa-miR-484, hsa-miR-874a, and hsa-miR-93; and, ii) mRNA gene products consisting of the group of: ADAT1, ANKRD52, BIRC6, C10orf18, C2CD2, CHD9, CHM, CPT1A, DAAM1, DIP2B, DPY19L3, FAM91A1, GMCL1, ME1, NCOA2, OTUD6B, PDSS2, PIK3CA, SMG1, TRIM23, TTC3, UBR5, UBXN7, and ZFC3H1.

4. The method of claim 3, wherein the miRNAs and mRNAs in the miRNA/mRNA signature each hybridize to at least one probe that is specific for such miRNAs and mRNA, relative to the control sample.

5. The method of claim 3, wherein a level of expression of the miRNAs and mRNAs is assessed by detecting the presence of a transcribed polynucleotide or portion thereof, wherein the transcribed polynucleotide comprises a coding region of the miRNA or mRNA.

6. The method of claim 3, wherein the at least miRNA/mRNA signature includes isolated variants or biologically-active fragments or functional equivalents of each miRNA and mRNA, or antibodies that bind thereto.

7. The method of claim 3, wherein the sample is a breast cancer-associated body fluid, cell or tissue.

8. The method of claim 3, wherein the sample comprises cells obtained from the patient.

9. The method of claim 3, wherein the sample comprises cells obtained from the patient taken over time.

10. The method of claim 3, wherein the breast cancer disease is an invasive ducal carcinoma (IDC) breast cancer.

11. The method of claim 3, wherein the step of determining the survival prognosis of the subject predicts overall survival (OS).

12. The method of claim 3, further comprising designing a treatment plan based on the diagnosis.

13. The method of claim 3, further comprising administration of a treatment based on the diagnosis.

14. The method of claim 3, wherein the test expression level is determined by RT-PCR.

15. The method of claim 3, wherein the miRNA/mRNA signature comprises a statistically significant change in the expression of the miRNAs and mRNAs in a non-cancerous breast cell versus a breast cancer cell.

16. The method of claim 3, wherein control miRNA and/or mRNA expression levels are from a representative pool of individuals, and are a mean, median or other statistically manipulated or otherwise summarized or aggregated representative miRNA and/or mRNA expression levels for the miRNA and miRNA levels in the control samples.

* * * * *